(12) United States Patent
Kawashima et al.

(10) Patent No.: US 7,775,977 B2
(45) Date of Patent: Aug. 17, 2010

(54) ULTRASONIC TOMOGRAPHIC DIAGNOSTIC APPARATUS

(75) Inventors: Tomonao Kawashima, Hachioji (JP); Kenji Kishi, Yokohama (JP)

(73) Assignee: Olympus Corporation, Tokyo (JP)

( * ) Notice: Subject to any disclaimer, the term of this patent is extended or adjusted under 35 U.S.C. 154(b) by 709 days.

(21) Appl. No.: 10/516,700

(22) PCT Filed: Sep. 18, 2003

(86) PCT No.: PCT/JP03/11891

§ 371 (c)(1),
(2), (4) Date: Dec. 2, 2004

(87) PCT Pub. No.: WO2004/028375

PCT Pub. Date: Apr. 8, 2004

(65) Prior Publication Data

US 2005/0256402 A1 Nov. 17, 2005

(30) Foreign Application Priority Data

Sep. 27, 2002 (JP) .............................. 2002-283802
Oct. 1, 2002 (JP) .............................. 2002-288951

(51) Int. Cl.
*A61B 8/14* (2006.01)
*A61B 8/00* (2006.01)
(52) U.S. Cl. ........................ 600/437; 600/443; 600/462
(58) Field of Classification Search ................. 600/424, 600/3, 443, 426, 463
See application file for complete search history.

(56) References Cited

U.S. PATENT DOCUMENTS 5,680,865 A * 10/1997 Tanaka ...................... 600/441
5,724,978 A    3/1998 Tenhoff
5,817,019 A   10/1998 Kawashima (Continued)

FOREIGN PATENT DOCUMENTS

EP          0 802 424 A2   10/1997

(Continued)

OTHER PUBLICATIONS

Supplementary European Search Report corresponding to European Patent Application No. 03748538.0, dated Feb. 1, 2008 (5 pgs.).

(Continued)

*Primary Examiner*—Eric F Winakur
*Assistant Examiner*—Helene Bor
(74) *Attorney, Agent, or Firm*—Straub & Pokotylo; John C. Pokotylo

(57) ABSTRACT

This ultrasonic diagnostic apparatus includes an image constructing circuit (31) for creating plural ultrasonic tomographic images resulting from a process in which an ultrasonic endoscope moves within a body cavity, a position detecting portion (13) for detecting position information of the ultrasonic tomographic images, an image processing circuit (33) for constructing tomographic parallel images resulting from arrangement of plural ultrasonic tomographic images along a scanning path of the ultrasonic endoscope based on the position information, and a display circuit (34) causing a monitor (14) to display an ultrasonic tomographic image and tomographic parallel images so as to compare them. In this ultrasonic diagnostic apparatus, when an ultrasonic image is displayed on the monitor, a spread and depth of an invasion of an affected part are displayed based on ultrasonic image data within a body cavity.

11 Claims, 34 Drawing Sheets

U.S. PATENT DOCUMENTS

| | | | |
|---|---|---|---|
| 5,924,989 | A | 7/1999 | Polz |
| 6,108,439 | A * | 8/2000 | Ishiguro ..................... 382/131 |
| 6,248,074 | B1 | 6/2001 | Ohno et al. |
| 6,256,529 | B1 * | 7/2001 | Holupka et al. ............. 600/427 |
| 6,267,727 | B1 * | 7/2001 | Teo ............................ 600/468 |
| 2001/0035871 | A1 | 11/2001 | Bieger et al. |
| 2001/0051766 | A1 * | 12/2001 | Gazdzinski ................ 600/309 |
| 2002/0049375 | A1 | 4/2002 | Strommer et al. |
| 2003/0065260 | A1 * | 4/2003 | Cheng et al. ................ 600/427 |
| 2003/0114742 | A1 * | 6/2003 | Lewkowicz et al. ......... 600/407 |
| 2003/0125624 | A1 * | 7/2003 | Shiki .......................... 600/443 |
| 2003/0199756 | A1 * | 10/2003 | Kawashima ................ 600/424 |
| 2003/0212327 | A1 * | 11/2003 | Wang et al. ................. 600/437 |
| 2004/0049111 | A1 * | 3/2004 | Hirooka et al. ............. 600/437 |
| 2004/0054248 | A1 * | 3/2004 | Kimchy et al. ................ 600/3 |
| 2004/0059217 | A1 * | 3/2004 | Kessman et al. ............ 600/424 |
| 2004/0138555 | A1 * | 7/2004 | Krag et al. .................. 600/424 |
| 2005/0055174 | A1 * | 3/2005 | David et al. ................ 702/152 |

FOREIGN PATENT DOCUMENTS

| | | |
|---|---|---|
| JP | 05-269132 | 10/1993 |
| JP | 09-192128 | 7/1997 |
| JP | 3040306 | 8/1997 |
| JP | 10-000192 | 1/1998 |
| JP | 10-005228 | 1/1998 |
| JP | 10-216127 | 8/1998 |
| JP | 11-047133 | 2/1999 |
| JP | 11-113913 | 4/1999 |
| JP | 11-318904 | 11/1999 |
| JP | 2000-023979 | 1/2000 |
| JP | 2000-023980 | 1/2000 |
| JP | 2001-017433 | 1/2001 |
| JP | 2001-500762 | 2/2001 |
| WO | WO 98/11823 | 3/1998 |

OTHER PUBLICATIONS

Notice of Rejection Grounds for Japanese Patent Application No. 2002-288951, mailed Nov. 11, 2008 (2 pgs.).

"Communication" for EP 08021668.2, mailed Feb. 26, 2009 including coversheet (1 pg.), European Search Report (1 pg.), Annex to the European Search Report (1 pg.), and Form 2906 (3 pgs.).

* cited by examiner

ULTRASONIC TOMOGRAPHIC IMAGES

DIRECTION OF MOVING ULTRASONIC ENDOSCOPE BY HAND

ULTRASONIC TOMOGRAPHIC DIAGNOSTIC APPARATUS

TECHNICAL FIELD

The present invention relates to an ultrasonic diagnostic apparatus and in particular to an ultrasonic diagnostic apparatus, which allows the real observation of a spread and/or depth of an invasion of a lesion.

BACKGROUND ART

A conventional ultrasonic diagnostic apparatus is disclosed in Japanese Unexamined Patent Application Publication No. 11-113913, for example, in which a body cavity radial scan type ultrasonic probe (including an ultrasonic endoscope having an optical observation window) having an ultrasonic transducer and a position detector at the distal end of a long and narrow insert portion to be inserted to a body cavity is inserted or withdrawn through a curved or bent lumen. Thus, plural ultrasonic tomographic images are obtained, and ultrasonic image data of a space along a lumen path thereof is obtained. Also, a body cavity convex scanning type ultrasonic probe having an ultrasonic transducer and a position detector at the distal end of an insert portion thereof is known in which the ultrasonic probe is inserted into a lumen and is rotated about an insert axis. Thus, plural ultrasonic tomographic images are obtained, and ultrasonic image data of the lumen space is obtained.

Furthermore, another ultrasonic diagnostic apparatus is known in which an ultrasonic probe for external use provided with a position detector irradiates ultrasonic wave to a body to be examined from outside of the body and is moved or rotated at the same time. Thus, plural ultrasonic tomographic images are obtained, and ultrasonic image data of the space is obtained. The ultrasonic diagnostic apparatus is proposed in Japanese Unexamined Patent Application Publication No. 10-216127 and Registered Utility Model No. 3040306.

Various methods for expressing an ultrasonic image on a monitor screen based on ultrasonic image data obtained in these ultrasonic diagnostic apparatus are examined. Following first and second expressing methods are adopted in the first patent document and a following third expressing method is adopted in the second patent document and third patent document.

In the first expressing method, three-dimensional image data expressed by orthogonal coordinates is created by averaging parts in which plural ultrasonic tomographic images overlap and/or by interpolating between ultrasonic tomographic images. Then, based on the three-dimensional image data, a cross-sectional image cut at a plane is expressed.

In the second expressing method, three-dimensional image data expressed by orthogonal coordinates is created by averaging parts in which plural ultrasonic tomographic images overlap and/or by interpolating between ultrasonic tomographic images. Then, based on the three-dimensional image data, an ultrasonic three-dimensional image is expressed.

In the third expressing method, a change in coordinate positions of an ultrasonic probe is obtained from an output of a position detector. Plural two-dimensional ultrasonic tomographic images are moved by an amount corresponding to a change in position of scan planes and are stacked. Thus, a pseudo three-dimensional image is expressed.

In an application of this kind of ultrasonic diagnostic apparatus, an operator may diagnose by moving an ultrasonic probe within an organ of a lumen form such as the stomach, the esophagus and the bowels. In this case, performing three observations, which will be described below, is important for estimating the prognosis and for determining an operation/treatment range.

A first observation is performed for finding from where to where a lesion spreads and invades along a lumen.

A second observation is performed for finding how deep the lesion invades in a direction vertical to a surface of the lumen.

A third Observation is performed for finding how wide and how deep the lesion invades to an organ or a portal blood vessel and so on which are in a deeper part over the lumen such as the pancreas or the like.

In order to perform the first to third observations, the first to third expressing methods are used.

On the other hand, a so-called external ultrasonic diagnostic apparatus has been conventionally proposed for creating a tomographic image by transmitting and receiving ultrasonic wave from an ultrasonic probe to and from the outside of a body to be examined. For example, one disclosed in Japanese Unexamined Patent Application Publication No. 9-192128, Japanese Unexamined Patent Application Publication No. 11-47133 or Japanese Unexamined Patent Application Publication No. 2001-17433 detects a positional relationship between an observing portion and an ultrasonic probe and/or a scan plane thereof (therefore, a position and direction of an ultrasonic tomographic image) by means of a position and direction detecting portion of using a magnetic field and displays the positional relationship on a monitor. When this kind of ultrasonic diagnostic apparatus displays a tomographic image on a monitor, a picture expressing an ultrasonic probe called probe mark is superimposed over a human-shape image called body mark expressing a body to be examined, which is prepared by the apparatus in advance. With the construction and the operation, an operator can easily recognize how and which part of a body to be examined is observed to obtain a given tomographic image during a diagnosis using images during and after an examination.

In this kind of conventional internal ultrasonic diagnostic apparatus, an operator generally uses an ultrasonic endoscope having an ultrasonic transducer as an ultrasonic probe and a CCD camera at the distal end of the ultrasonic endoscope. Then, the operator inserts the distal end of the ultrasonic endoscope into the vicinity of an area of concern such as a tumor by observing an optical image from the CCD camera at the same time. Next, in accordance with a position of the organ appearing on an ultrasonic image, and based on anatomical knowledge of the operator, the operator determines the position and direction of the ultrasonic image obtained by the ultrasonic transducer. Next, the operator projects the area of concern in the ultrasonic image by moving the distal end of the ultrasonic endoscope.

DISCLOSURE OF INVENTION

One ultrasonic diagnostic apparatus of the invention is an ultrasonic diagnostic apparatus obtaining plural ultrasonic tomographic images at a process that an ultrasonic probe moves and scans within a body cavity of a body to be examined, the apparatus including position information detecting means for detecting position information of plural ultrasonic tomographic images obtained in a process that the ultrasonic probe moves within a body cavity of a body to be examined, and tomographic parallel-images constructing means for constructing plural tomographic parallel images arranged along a scan path of the ultrasonic probe based on the position information obtained by the position information detecting unit.

Another ultrasonic diagnostic apparatus of the invention is an ultrasonic diagnostic apparatus moving an ultrasonic transducer within a body cavity of a body to be examined and creating plural chronological tomographic images in accordance with the movement, the apparatus including position information detecting means for detecting position information of the ultrasonic transducer when the tomographic images are obtained, and auxiliary image creating means creating an auxiliary image illustrating position information of the tomographic images along a path of the movement of the ultrasonic transducer based on position information obtained by the position information detecting means and the tomographic images corresponding to the position information.

BEST MODE FOR CARRYING OUT THE INVENTION

Embodiments of the invention will be described below with reference to drawings.

Figure 1:
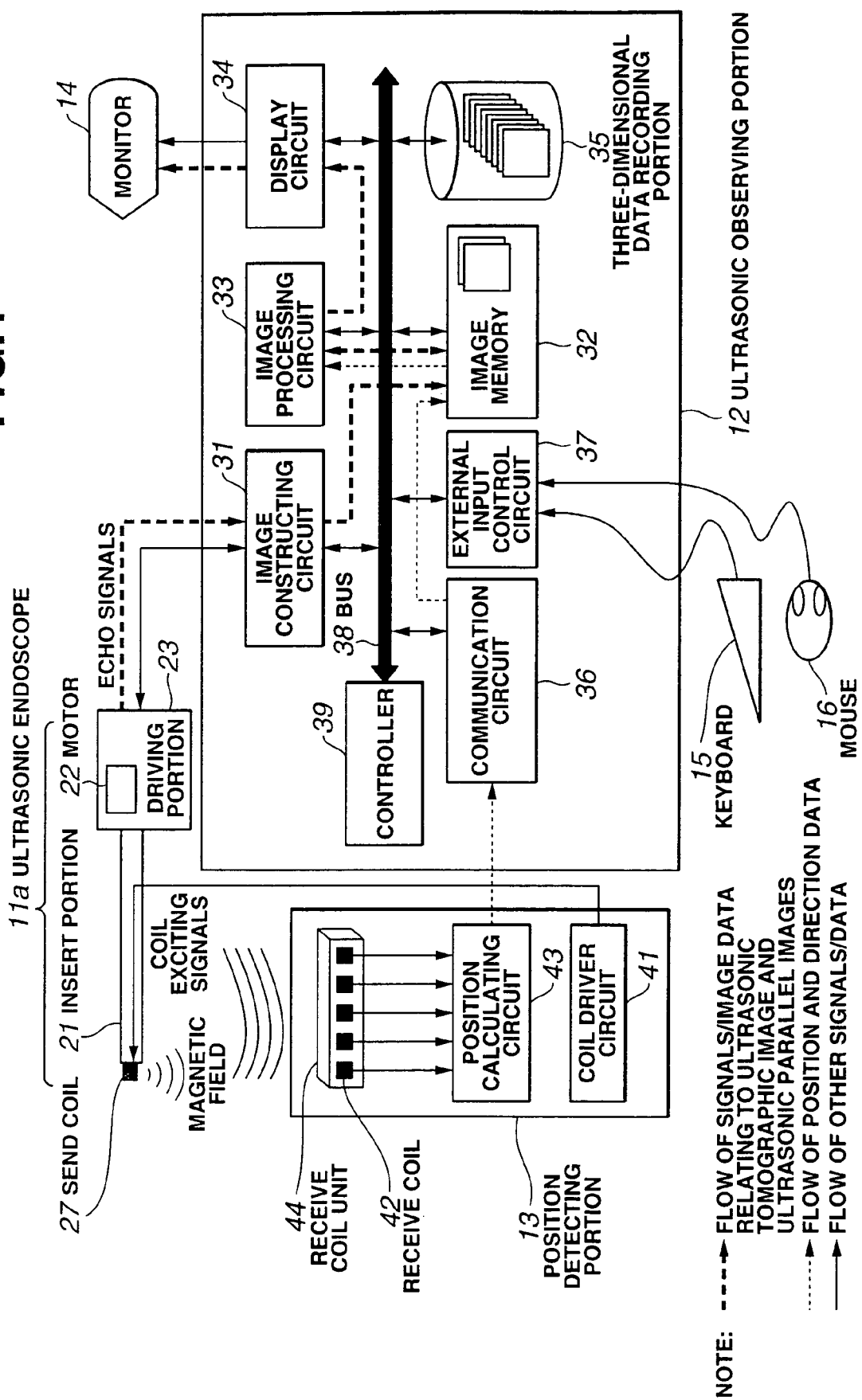
FIG. 1 is a block diagram showing an entire configuration of an ultrasonic diagnostic apparatus according to a first embodiment of the present invention.
Figure 2:
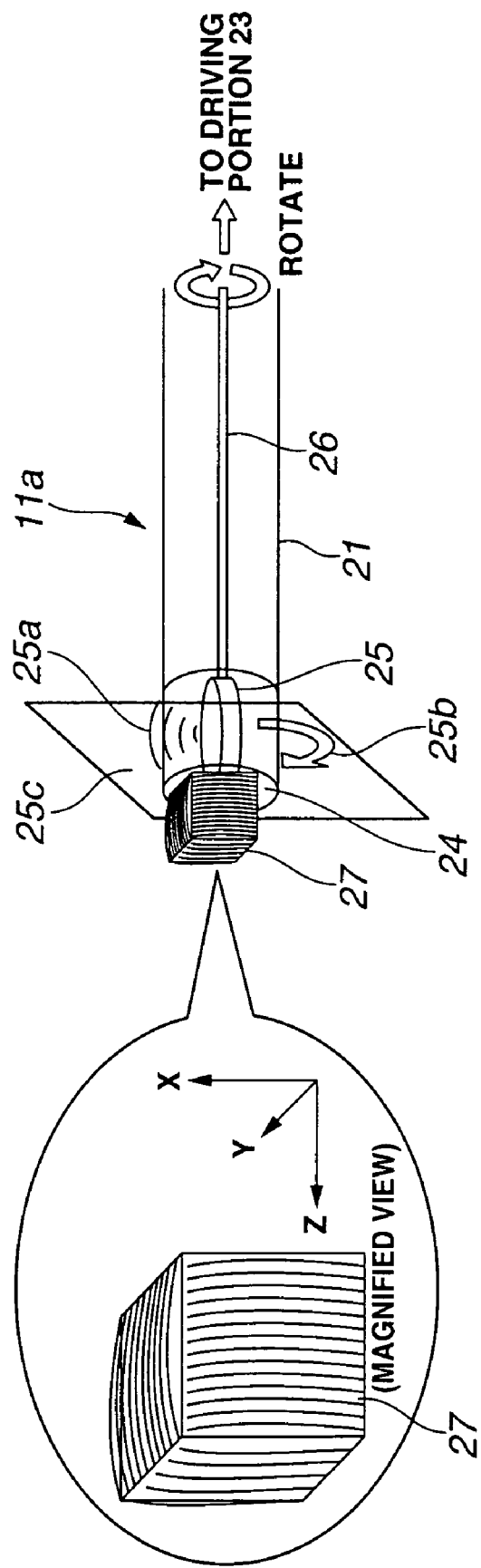
FIG. 2 is a block diagram showing a configuration of the distal end of an insert portion of an ultrasonic endoscope to be used in the ultrasonic diagnostic apparatus according to the first embodiment.
Figure 3:
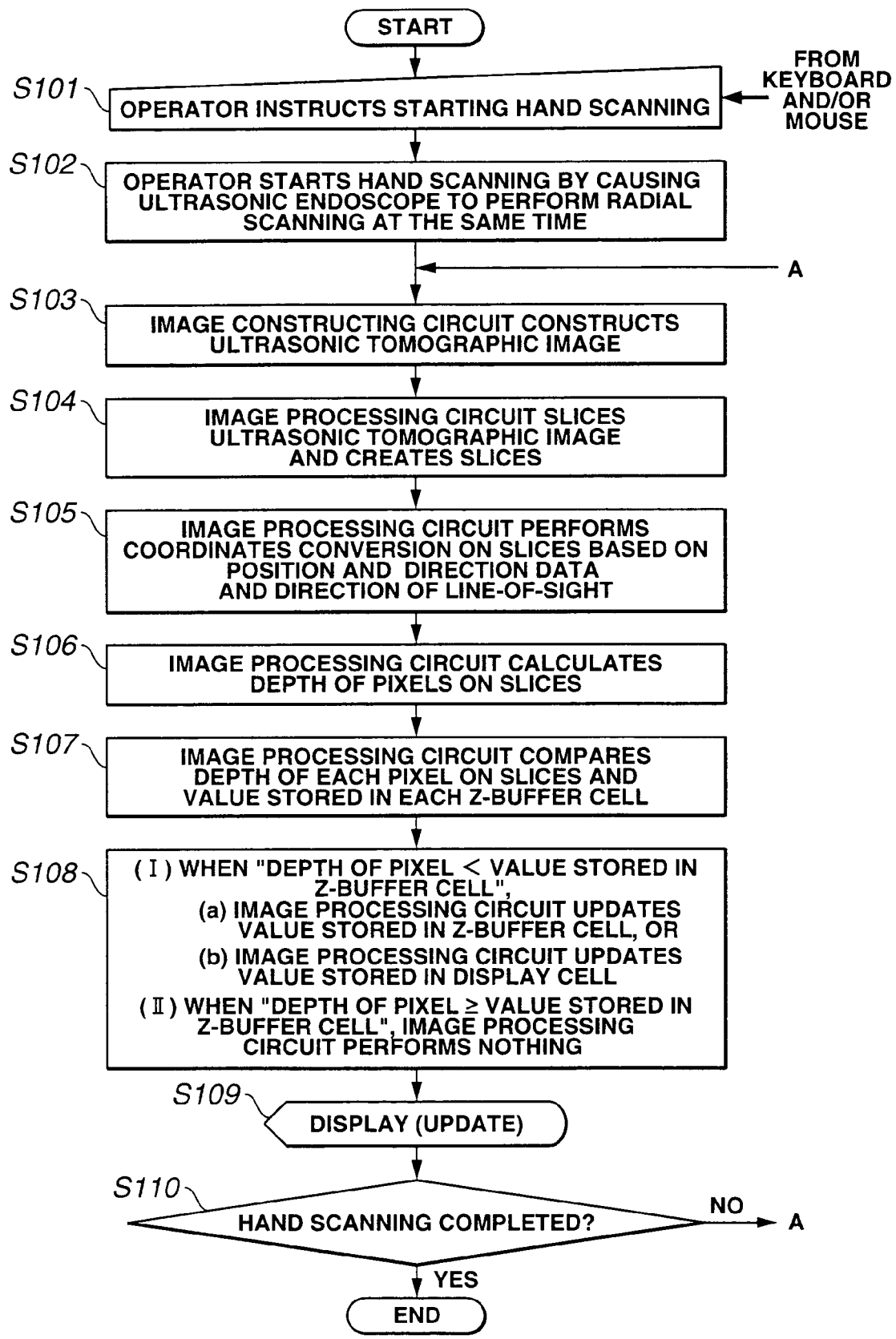
FIG. 3 is a flowchart describing an operation for creating tomographic parallel images by performing a hand scanning by means of the ultrasonic diagnostic apparatus according to the first embodiment.
Figure 4:
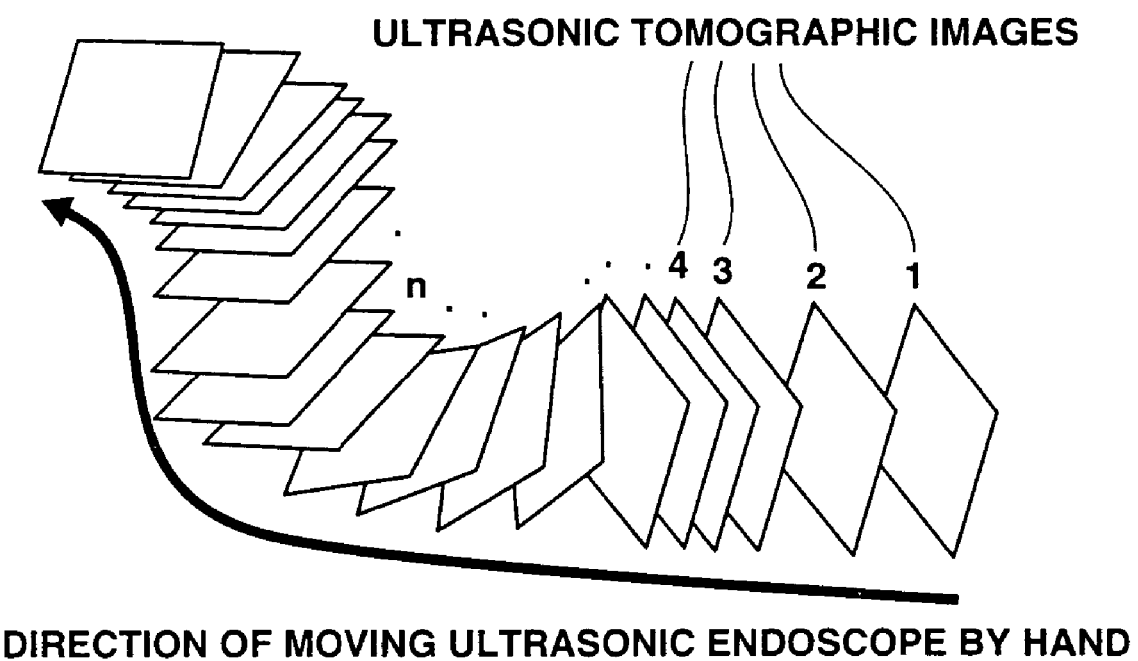
FIG. 4 is an explanatory diagram of an ultrasonic tomographic image created by a hand scanning by means of the ultrasonic diagnostic apparatus according to the first embodiment.
Figure 5:
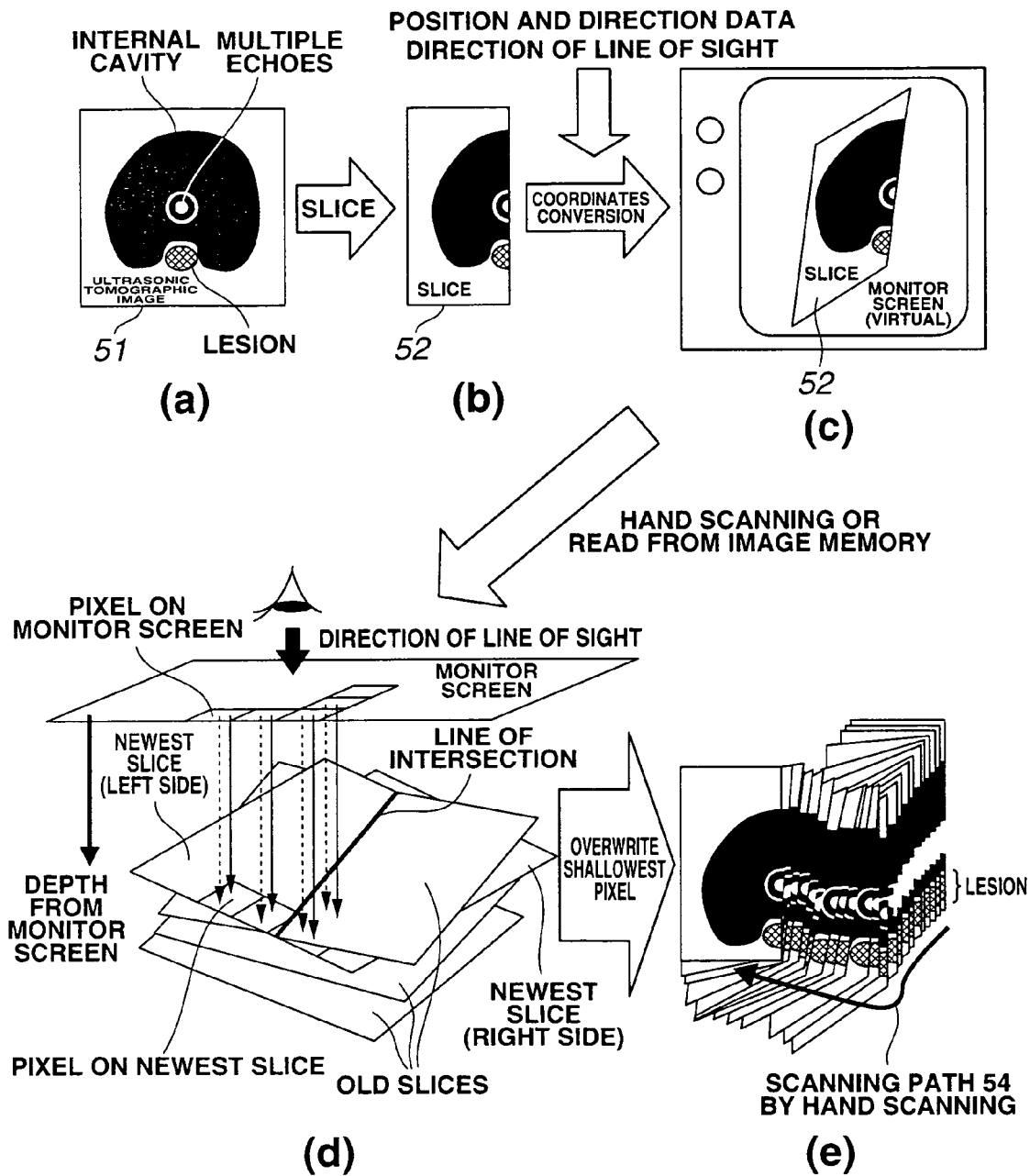
FIG. 5 is an explanatory diagram describing an operation for slicing an ultrasonic tomographic image by means of the ultrasonic diagnostic apparatus according to the first embodiment.
Figure 6:
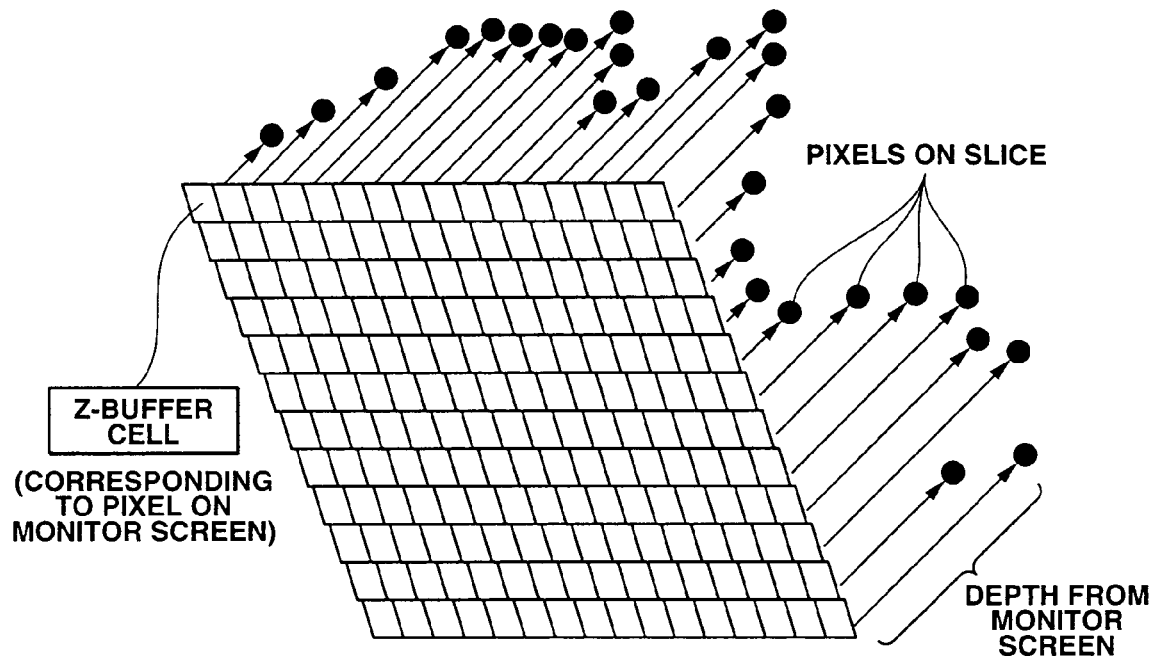
FIG. 6 is an explanatory diagram describing Z buffer cells of the ultrasonic diagnostic apparatus according to the first embodiment.
Figure 7:
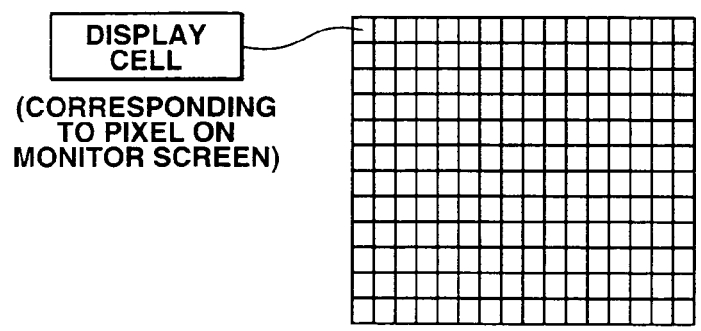
FIG. 7 is an explanatory diagram describing an arrangement of pixels on a monitor screen of the ultrasonic diagnostic apparatus according to the first embodiment.
Figure 8:
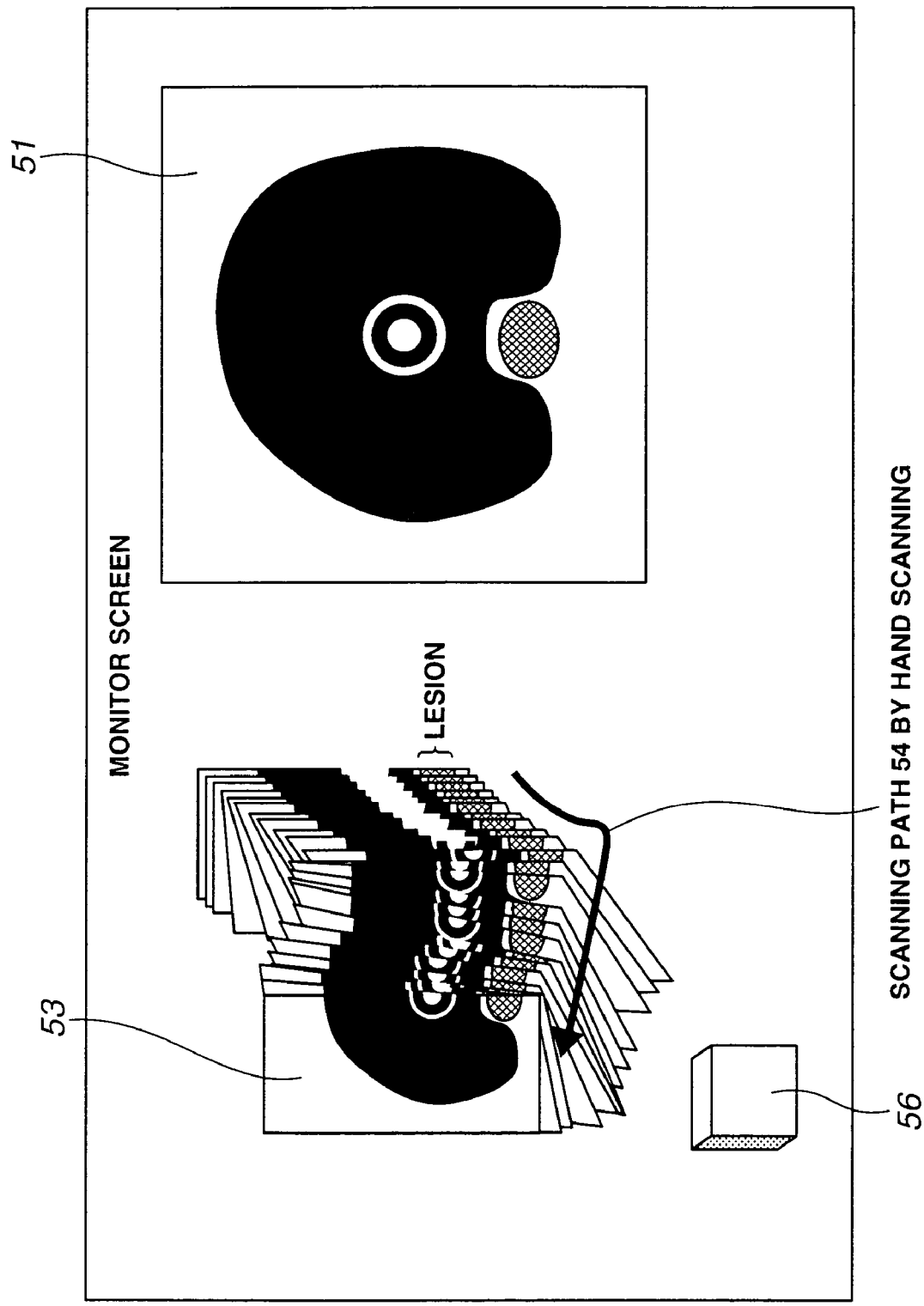
FIG. 8 is an explanatory diagram describing a display state on the monitor screen of the ultrasonic diagnostic apparatus according to the first embodiment.
Figure 9:
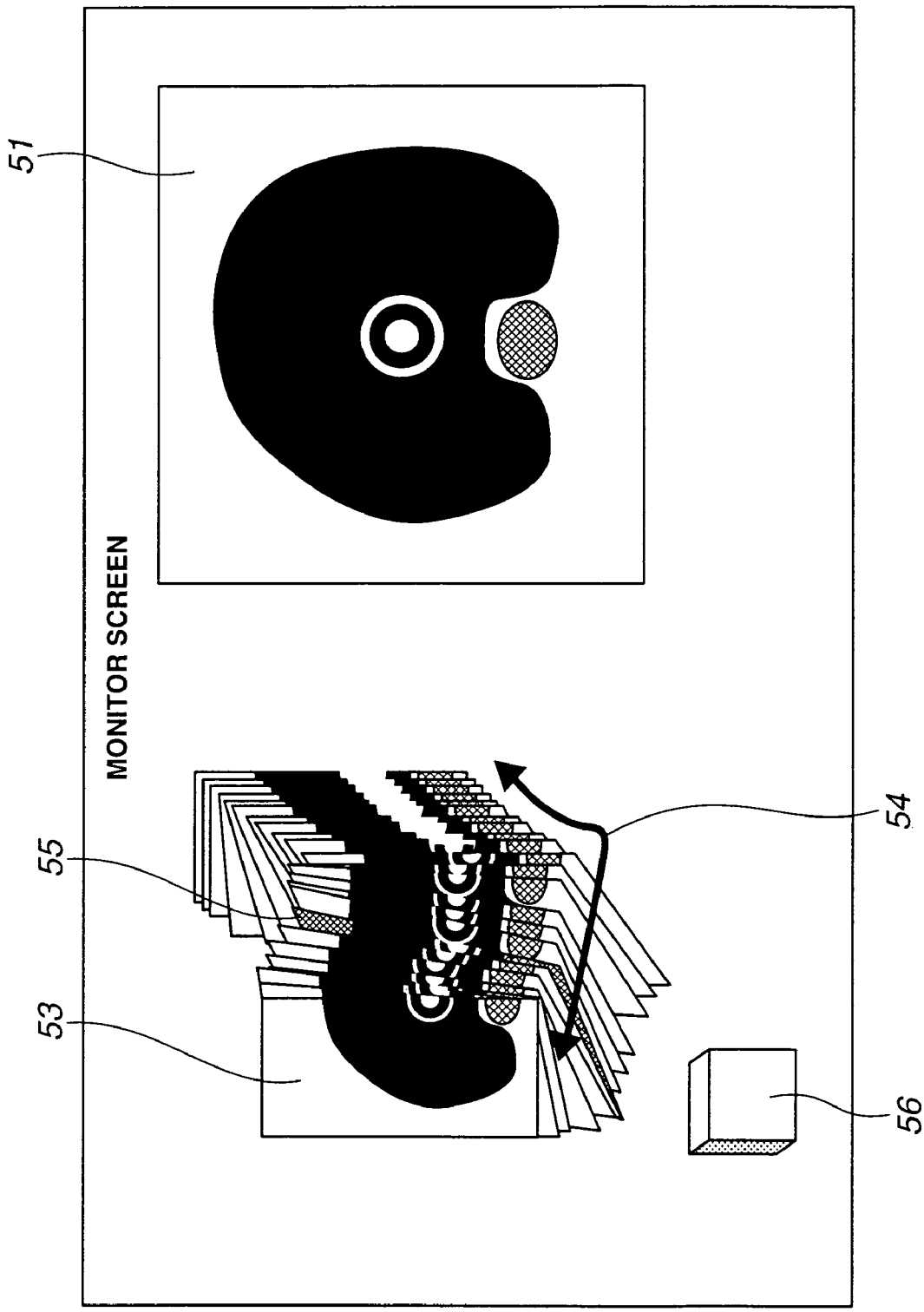
FIG. 9 is an explanatory diagram describing an operation for moving an ultrasonic tomographic image marker on the monitor screen of the ultrasonic diagnostic apparatus according to the first embodiment.
Figure 10:
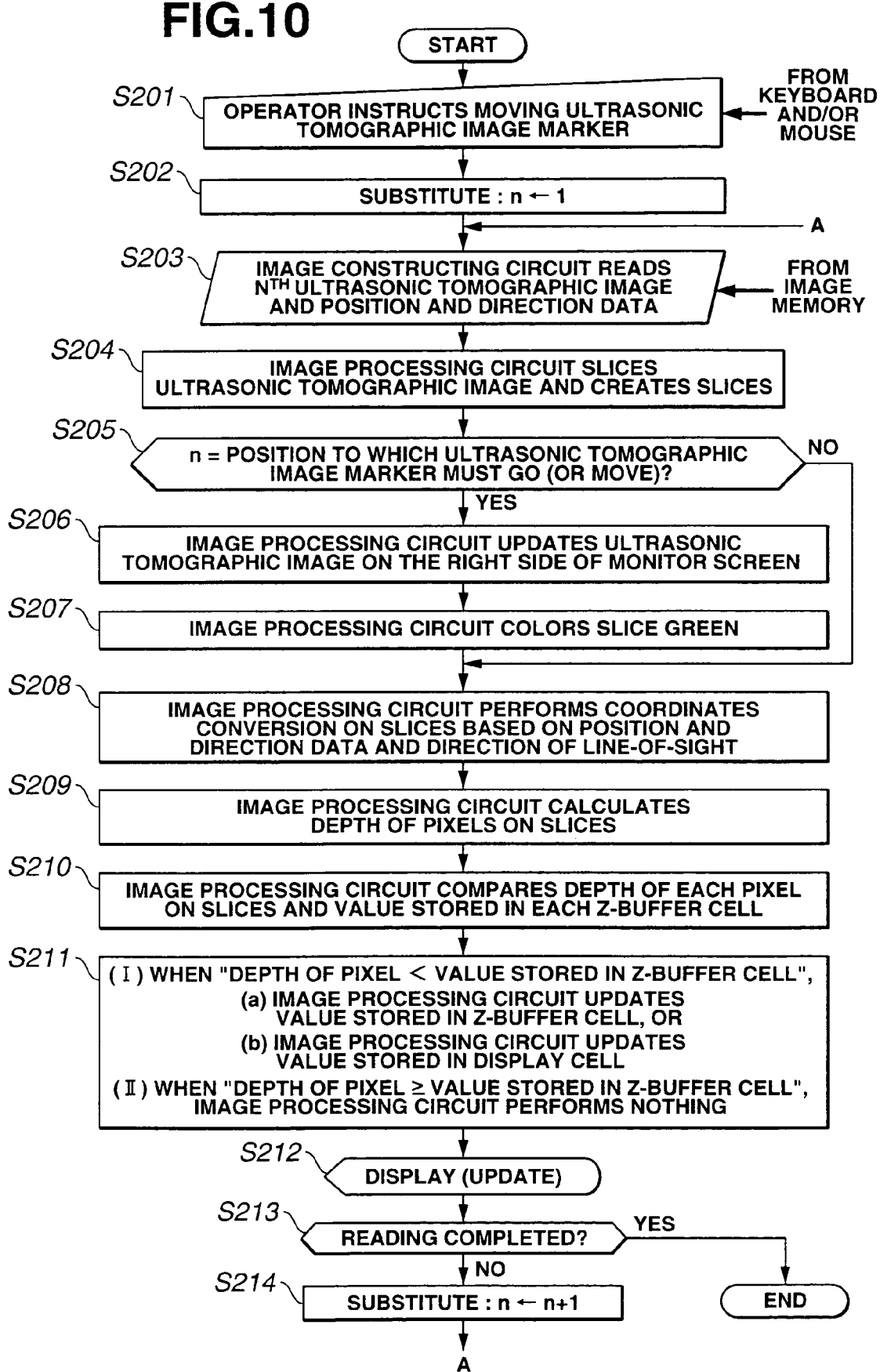
FIG. 10 is a flowchart describing the operation for moving an ultrasonic tomographic image marker by the ultrasonic diagnostic apparatus according to the first embodiment.
Figure 11:
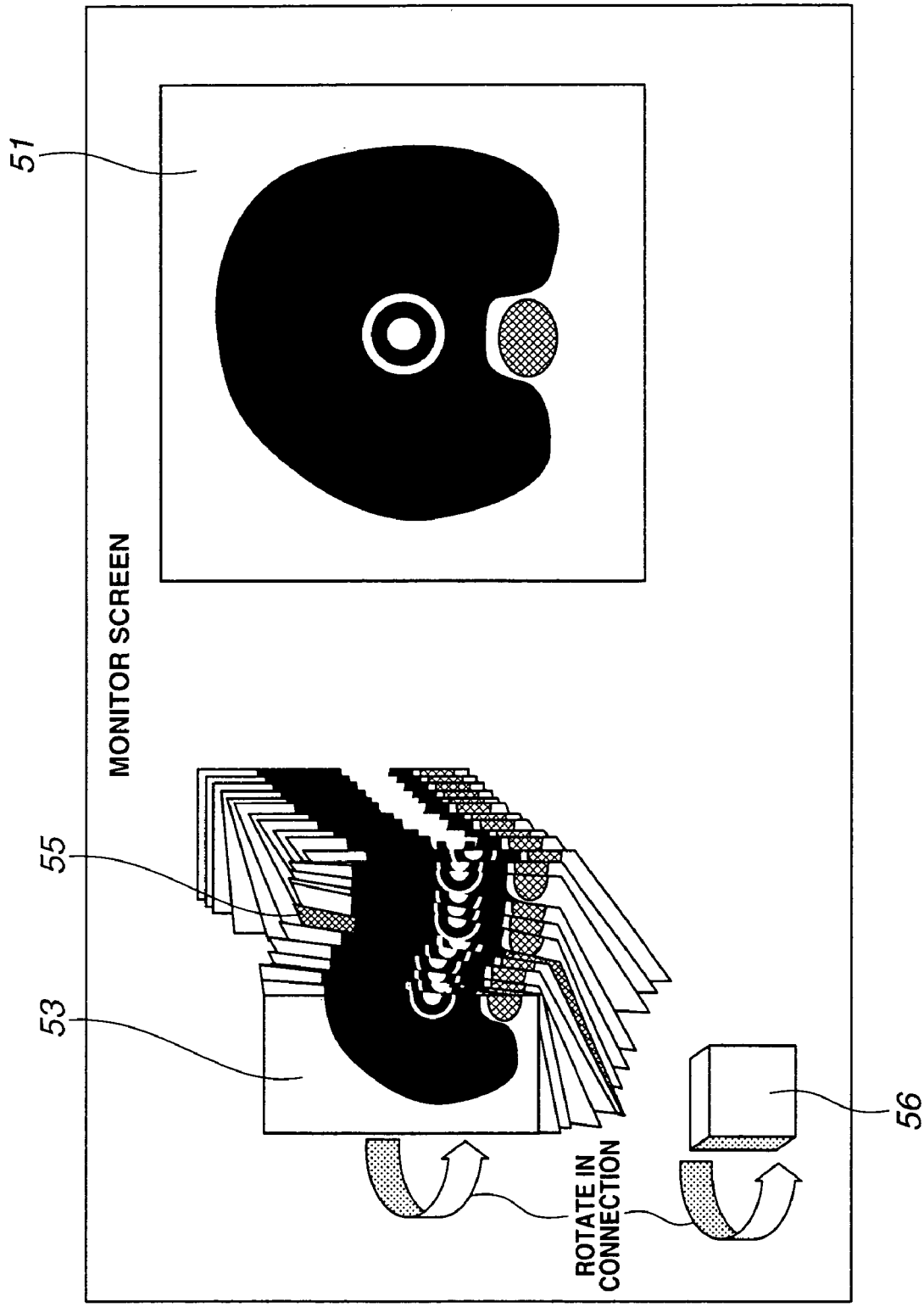
FIG. 11 is an explanatory diagram describing an operation for rotating tomographic parallel images on the monitor screen by the ultrasonic diagnostic apparatus according to the first embodiment.
Figure 12:
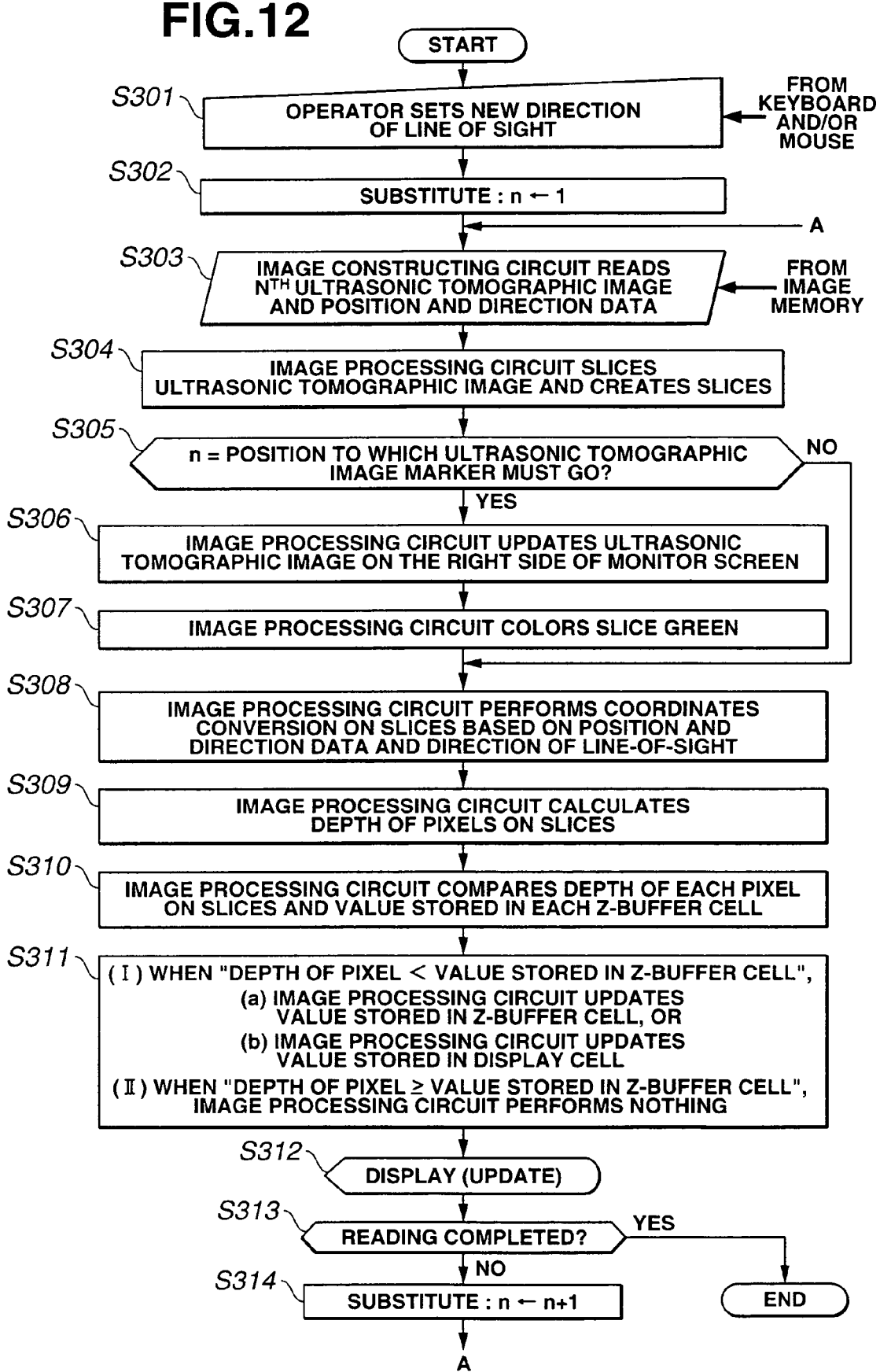
FIG. 12 is a flowchart describing an operation for rotating tomographic parallel images by the ultrasonic diagnostic apparatus according to the first embodiment.
Figure 13:
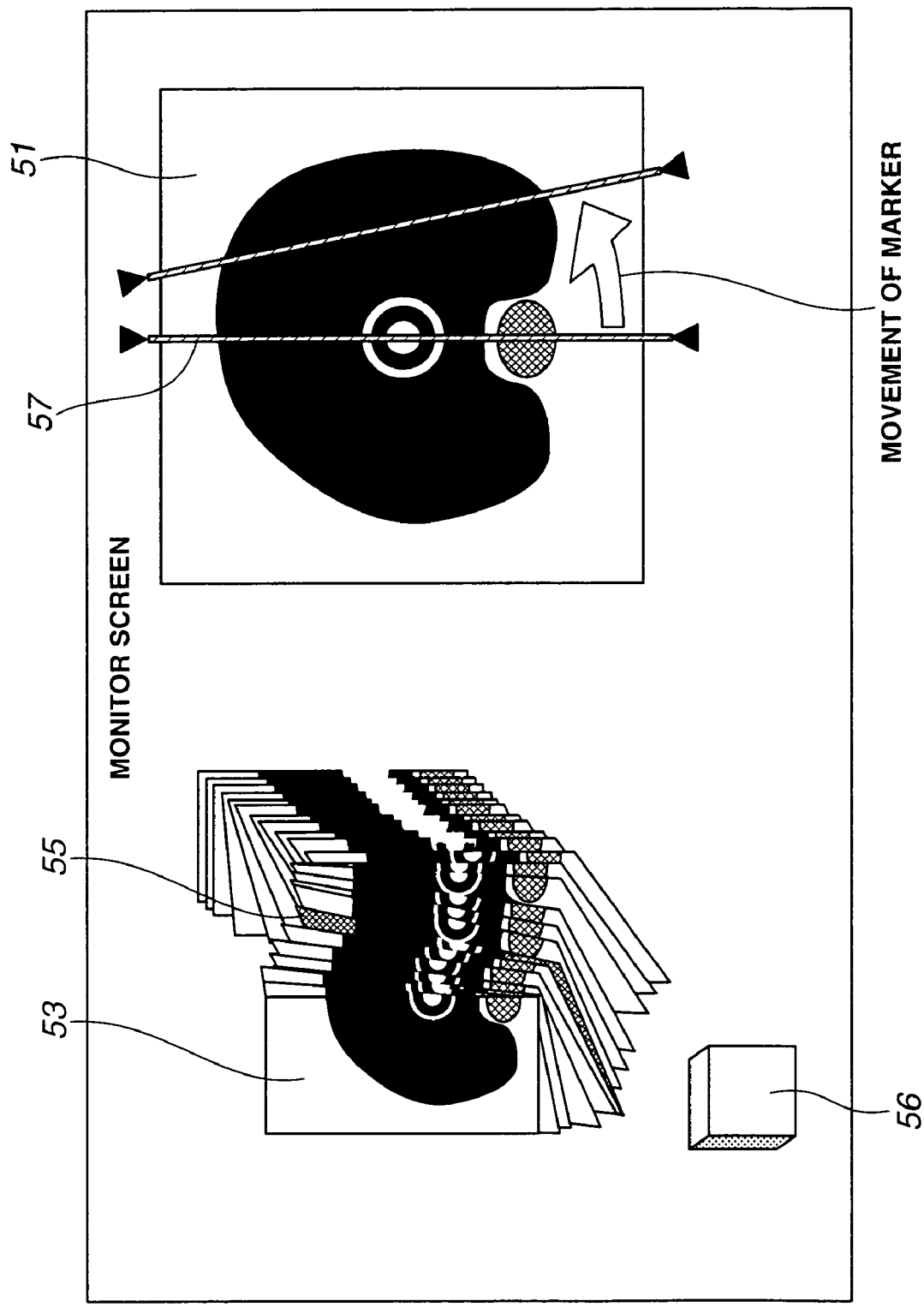
FIG. 13 is an explanatory diagram describing changing of a position of slicing tomographic parallel images and moving of a slice marker on the monitor screen of the ultrasonic diagnostic apparatus according to the first embodiment.
Figure 14:
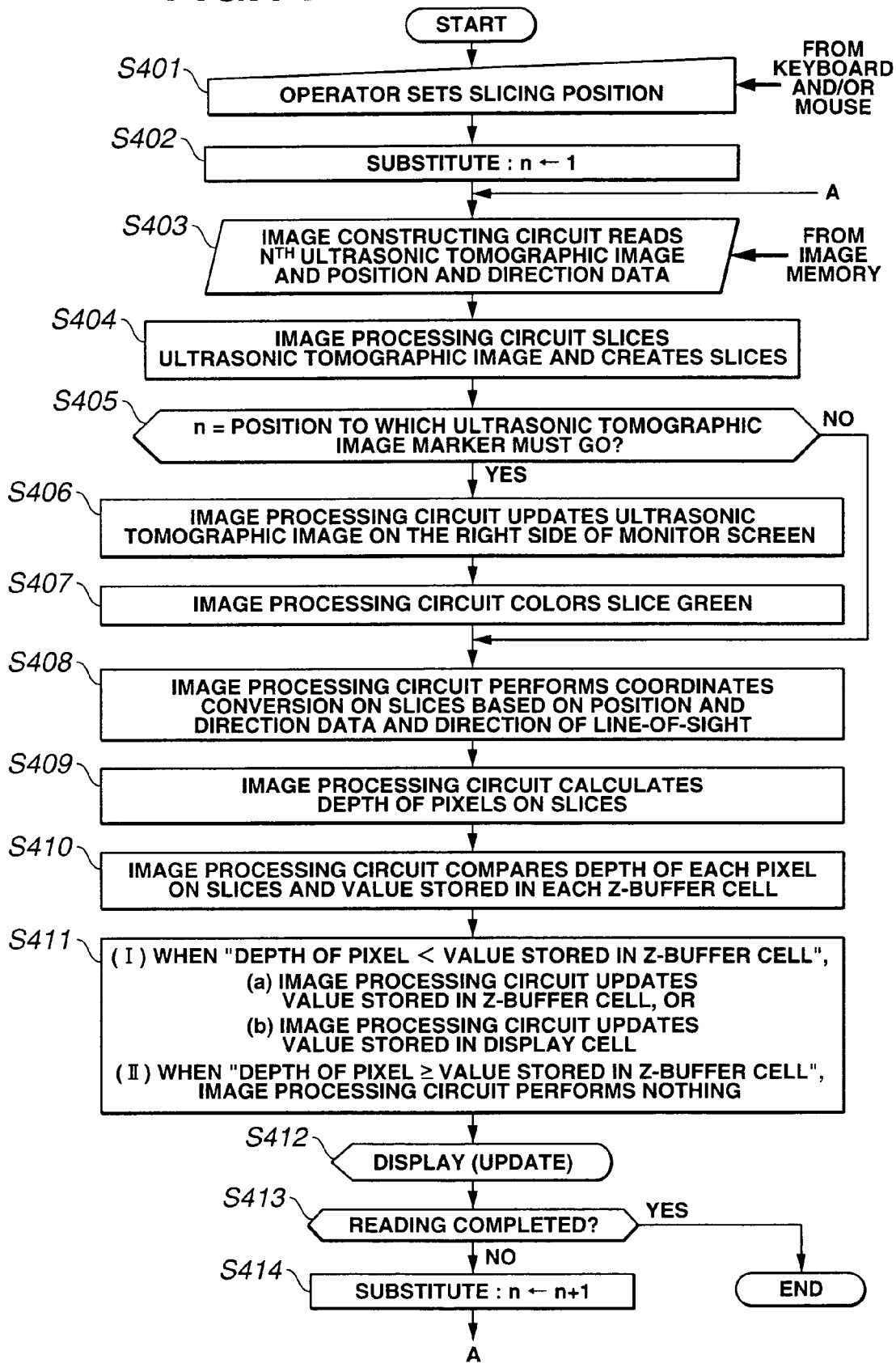
FIG. 14 is a flowchart describing operations for changing a position of slicing tomographic parallel images and moving a slice marker by the ultrasonic diagnostic apparatus according to the first embodiment.

FIGS. 1 to 14 are diagrams describing a first embodiment of an ultrasonic diagnostic apparatus according to the invention. FIG. 1 is a block diagram showing an entire configuration of an ultrasonic diagnostic apparatus of the first embodiment. FIG. 2 is a block diagram showing a configuration of the distal end of an insert portion of an ultrasonic endoscope to be used in the ultrasonic diagnostic apparatus according to the first embodiment. FIG. 3 is a flowchart describing an operation for creating tomographic parallel images by performing a hand scanning by means of the ultrasonic diagnostic apparatus according to the first embodiment. FIG. 4 is an explanatory diagram of an ultrasonic tomographic image created by a hand scanning by means of the ultrasonic diagnostic apparatus according to the first embodiment. FIG. 5 is an explanatory diagram describing an operation for slicing an ultrasonic tomographic image by means of the ultrasonic diagnostic apparatus according to the first embodiment. FIG. 6 is an explanatory diagram describing Z buffer cells of the ultrasonic diagnostic apparatus according to the first embodiment. FIG. 7 is an explanatory diagram describing an arrangement of pixels on a monitor screen of the ultrasonic diagnostic apparatus according to the first embodiment. FIG. 8 is an explanatory diagram describing a display state on the monitor screen of the ultrasonic diagnostic apparatus according to the first embodiment. FIG. 9 is an explanatory diagram describing an operation for moving an ultrasonic tomographic image marker on the monitor screen of the ultrasonic diagnostic apparatus according to the first embodiment. FIG. 10 is a flowchart describing the operation for moving an ultrasonic tomographic image marker by the ultrasonic diagnostic apparatus according to the first embodiment. FIG. 11 is an explanatory diagram describing an operation for rotating tomographic parallel images on the monitor screen by the ultrasonic diagnostic apparatus according to the first embodiment. FIG. 12 is a flowchart describing an operation for rotating tomographic parallel images by the ultrasonic diagnostic apparatus according to the first embodiment. FIG. 13 is an explanatory diagram describing changing of a position of slicing tomographic parallel images and moving of a slice marker on the monitor screen of the ultrasonic diagnostic apparatus according to the first embodiment. FIG. 14 is a flowchart describing operations for changing a position of slicing tomographic parallel images and moving a slice marker by the ultrasonic diagnostic apparatus according to the first embodiment.

As shown in FIG. 1, an ultrasonic diagnostic apparatus according to the first embodiment includes an ultrasonic endoscope 11a, an ultrasonic observing portion 12, a position detecting portion 13, a monitor 14, a keyboard 15 and a mouse 16. The ultrasonic endoscope 11a is an ultrasonic probe. The ultrasonic observing portion 12 includes tomographic parallel-images constructing means for creating tomographic parallel images from ultrasonic tomographic images, ultrasonic tomographic image marker setting means, slicing position setting means, rotating means, display control means, slicing means and the like. The position detecting portion 13 is positional information detecting means. The monitor 14 is display means. The keyboard 15 includes ultrasonic tomographic image marker setting means, slicing position setting means, rotating means and the like.

The ultrasonic endoscope 11a, which is an ultrasonic probe, includes an insert portion 21 and a driving portion 23. The insert portion 21 contains a flexible material and is to be inserted into a body cavity of a body to be examined. The driving portion 23 includes a motor 22 driving and rotating an ultrasonic transducer 25, which will be described later, disposed at the distal end of the insert portion 21.

An acoustically translucent distal-end cap 24 is provided at the distal end of the insert portion 21 of the ultrasonic endoscope 11a as shown in FIG. 2. The distal-end cap 24 contains a material allowing ultrasonic wave to pass through. The ultrasonic transducer 25 is arranged in the distal-end cap 24 and an acoustic medium (not shown) is filled in the ultrasonic transducer 25.

The ultrasonic transducer 25 is mounted and fixed at a distal end of a flexible shaft 26 containing a flexible member. The other end of the flexible shaft 26 is connected to a rotationally-driving axis of the motor 22 of the driving portion 23.

The ultrasonic transducer 25 is connected to an image constructing circuit 31, which will be described later, of the ultrasonic observing portion 12 by a signal line (not shown) provided in the flexible shaft 26, through the driving portion 23.

A send coil 27 generating a magnetic field is provided at the distal end of the distal-end cap 24 of the insert portion 21. The send coil 27 is connected to a coil driver circuit 41, which will be described, of the position detecting portion 13 by a signal line (not shown) provided in the insert portion 21.

The send coil 27 is wound about the insert portion 21 in two directions orthogonal to the axis direction (the shown X-axis direction and Y-axis direction with respect to the Z-axis of the insert portion 21 shown in FIG. 2). The Z-axis is a direction in which the insert portion 21 of the ultrasonic endoscope 11a is inserted. The X-axis and Y-axis are parallel to a radial scan plane 25c, which will be described later, and vertical to the Z-axis.

When the motor 22 of the driving portion 23 of the ultrasonic endoscope 11a is driven and rotated, the flexible shaft 26 rotates in a direction indicated by the shown arrow. Then, the ultrasonic transducer 25 is also driven and is rotated in the direction of a radial scan 25b indicated by the shown arrow. When the ultrasonic transducer 25 is driven by ultrasonic oscillation, an ultrasonic beam 25a is projected.

The ultrasonic observing portion 12 has an image constructing circuit 31, a large capacity image memory 32, an image processing circuit 33, a display circuit 34, a large capacity three-dimensional data recording portion 35, a communication circuit 36 and an external input control circuit 37 and further includes a controller 39. The image constructing circuit 31 outputs pulse-voltage-shaped exciting signals for driving by ultrasonic oscillation. Also, the image constructing circuit 31 performs different kinds of signal processing on echo signals from the ultrasonic transducer 25 and constructs ultrasonic image data. The image memory 32 stores image data created by the image constructing circuit 31 and image data of plural ultrasonic tomographic images created by the image processing circuit 33, which will be described later. The image processing circuit 33 is a circuit performing different kinds of image processing on image data stored in the image memory 32 and includes tomographic parallel image constructing means. The display circuit 34 is a display control means. The display circuit 34 performs digital-analog converting processing on image data having undergone different kinds of image processing in the image processing circuit 33 to convert analog video signals and causes the monitor 14 to display an image. The three-dimensional data recording portion 35 is a hard disk for storing image data constructed by the image constructing circuit 31 and/or position and direction data, which will be described later, for a long period of time. The communication circuit 36 performs different kinds of communication for exchanging different kinds of information with the position detecting portion 13. The external input control circuit 37 receives an instruction input from the keyboard 15 and/or the mouse 16. The controller 39 is a control portion giving a drive control command to the image constructing circuit 31, the image memory 32, the image processing circuit 33, the display circuit 34, the three-dimensional data recording portion 35, the communication circuit 36 and the external input control portion 37 through a bus 38 provided among the circuits 31 to 37. The controller 39 has tomographic parallel image constructing means, ultrasonic tomographic image marker setting means, slicing position setting means, rotating means, slicing means and rotating means and the like.

The image memory 32 includes three areas. One of these areas stores image data of ultrasonic tomographic images output from the image constructing circuit 31. Another area stores image data for displaying images created by the image processing circuit 33 on the monitor 14. Another area stores a Z-buffer, which will be described later.

The monitor 14 displays an ultrasonic tomographic image 51 (see FIG. 5) based on analog video signals generated by the display circuit 34. The keyboard 15 has plural keys and is used to input instruction for different operations using these keys. The mouse 16 is used to input instructions for different operations by manipulating symbols and/or signs displayed on the monitor 14.

The position detecting portion 13 includes a coil driver circuit 41, a receive coil unit 44 and a position calculating circuit 43. The coil driver circuit 41 outputs coil exciting signals to the send coil 27 of the ultrasonic endoscope 11a. The receive coil unit 44 is placed and fixed at a specific position by a predetermined placing method, wherein the receive coil unit 44 has plural receive coils 42 sequentially detecting magnetic fields from the send coil 27 and generates and outputs position signals. The position calculating circuit 43 calculates and generates position and direction data from position signals generated by the receive coil unit 44.

The receive coil unit 44 has plural receive coils 42 fixed integrally in a rectangular parallelepiped cabinet. In FIG. 1, the receive coils 42 are aligned and fixed on a straight line in the receive coil unit 44 for the convenience of space of paper. However, in reality, the receive coils 42 may be aligned and fixed on a two-dimensional plane or in a three-dimensional space.

An operation for constructing the ultrasonic tomographic image 51 (see FIG. 5) in the ultrasonic diagnostic apparatus having the above-described construction will be described.

The ultrasonic transducer 25 generates and projects an ultrasonic beam, which is a compressional wave of a medium, based on pulse-voltage-shaped exciting signals from the image constructing circuit 31 of the ultrasonic observing portion 12. The ultrasonic beam is projected to the outside of the insert portion 21 of the ultrasonic endoscope 11a via an acoustic medium filled in the distal end of the insert portion 21 and the distal-end cap 24. The ultrasonic beam projected to the outside is reflected within a body to be examined and is input to the ultrasonic transducer 25 as a reflected echo. The ultrasonic transducer 25 converts the reflected echo to echo signals and outputs the echo signal to the image constructing circuit 31.

While operations of the projection of ultrasonic beams by the ultrasonic transducer 25 and the generation of reflected echo signals are repeated, the flexible shaft 26 and the ultrasonic transducer 25 rotate in the respective directions indicated by the shown respective arrows by rotationally driving the motor 22 within the driving portion 23. Thus, the ultrasonic beams are sequentially and radially projected within the radial scan plane 25c vertical to the axis direction of the insert portion 21 of the ultrasonic endoscope 11a. As a result, so-called mechanical radial scanning (simply called radial scanning, hereinafter) 25b is performed.

The echo signals generated by the ultrasonic transducer 25 undergo publicly known processing in the image constructing circuit 31 of the ultrasonic observing portion 12 to construct so-called ultrasonic tomographic image data (simply called ultrasonic tomographic image, hereinafter). The publicly known processing may include envelope detection, logarithm multiplication, analog/digital conversion and scan conversion (processing converting image data of a polar coordinates system generated by radial scanning to image data of an orthogonal coordinates system). The ultrasonic tomographic image is stored in the image memory 32 through the bus 38.

Next, an operation relating to position and direction data will be described.

The coil driver circuit 41 of the position detecting portion 13 sequentially outputs an exciting signal to the send coil 27. Based on the exciting signal, the send coil 27 spatially generates a magnetic field. On the other hand, the receive coil 42 of the receive coil unit 44 sequentially detects magnetic fields from the send coil 27 and generates a position signal. Then, the receive coil 42 outputs the position signal to the position calculating circuit 43.

The position calculating circuit 43 calculates position and direction data based on the position signal from the receive coil 42 and outputs the position and direction data to the communication circuit 36. The position and direction data is data including a position and direction of the send coil 27 with respect to the receive coil unit 44. More specifically, position and direction data includes not only a position of the send coil 27 but also a direction (Z-axis direction in FIG. 2) that the ultrasonic endoscope 11a is inserted and a specific direction (Y-axis direction in FIG. 2) parallel to an ultrasonic tomographic image.

Here, when the send coil 27 is mounted at the distal-end cap 24 of the insert portion 21 such that the Y-axis in FIG. 2 can be at 12 o'clock position of the ultrasonic tomographic image (the upper direction of the ultrasonic tomographic image displayed on the monitor 14, the position and direction data includes the direction of the normal (Z-axis in FIG. 2) and the direction of 12 o'clock (Y-axis in FIG. 2) of the ultrasonic tomographic image.

The communication circuit 36 receives position and direction data from the position calculating circuit 43 via the bus 38 and outputs the data to the image memory 32. The image memory 32 stores the data.

The ultrasonic tomographic image and the position and direction data are stored in the image memory 32 in connection and in synchronization with each other under the control of the controller 39.

Next, an operation of the controller 39 for generating tomographic parallel images for performing an ultrasonic diagnosis by using the ultrasonic endoscope 11a will be described with reference to FIG. 3.

When an operator operating the ultrasonic diagnostic apparatus causes the display of a menu having different items and inputs a selection of an item from the displayed menu by using the keyboard 15 and/or the mouse 16, the data of the selected item is transmitted from the external input control circuit 37 to the controller 39. In accordance with the selection input, the controller 39 drives and controls the circuits 31 to 36. In the processing in FIG. 3, under the control of the controller 39, the construction of an ultrasonic tomographic image, the slicing of the tomographic image and/or the construction of tomographic parallel images thereof may be performed.

In other words, when an operator inputs a manipulation for starting an ultrasonic diagnosis (command for starting a hand scanning) at a step S101, the controller 39 drives and controls the image constructing circuit 31 to output an exciting signal to the ultrasonic transducer 25. Furthermore, the controller 39 drives and rotates the motor 22 and starts the radial scanning 25b of the ultrasonic transducer 25.

At a step S102, the operator repeats the hand scanning for inserting and withdrawing the insert portion 21 of the ultrasonic endoscope 11a within a body cavity of a body to be examined along a lumen by performing the radial scanning 25b at the same time. Based on a reflected echo from the ultrasonic transducer 25, the controller 39 drives and controls the image constructing circuit 31, and ultrasonic tomographic images are constructed sequentially. This scanning method is called "hand scanning", hereinafter. The ultrasonic tomographic image 51 and the tomographic parallel images 53 are constructed through a scanning path 54, which is a path of the hand scanning (see FIGS. 5 and 8). In accordance with the advance of the hand scanning, the scanning path 54 sequentially extends (FIG. 5).

Once the hand scanning starts, the controller 39 causes the image constructing circuit 31 to sequentially construct ultrasonic tomographic images as shown in FIG. 4 based on reflected echoes from the ultrasonic transducer 25 at a step S103. In FIG. 4, reference numerals 1 to n are given to the ultrasonic tomographic images in order of the construction.

The ultrasonic tomographic image constructed by the image constructing circuit 31 is stored in the image memory 32 in synchronization and in connection with the position and direction data calculated by the position calculating circuit 43 when the ultrasonic tomographic image is constructed. An example of the ultrasonic tomographic image 51 which is displayed on the monitor 14 is shown as the ultrasonic tomographic image 51 in (a) of FIG. 5.

Next, at a step S104, the controller 39 drives and controls the image processing circuit 33 to read the ultrasonic tomographic image and the position and direction data from the image memory 32, slice the ultrasonic tomographic image 51 and create slices 52.

A position slicing the ultrasonic tomographic image 51 is preset. For example, when it is preset that the ultrasonic tomographic image 51 shown in (a) of FIG. 5 is sliced at a straight line through the center of the image (that is, the rotational center of the ultrasonic transducer 25), the slicing at the slicing position results in slices 52 including a slice 52 shown in (b) of FIG. 5. The setting of the slicing position may be changed.

The slices 52 resulting from the slicing at the slicing position at the step S104 undergo coordinates conversion based on the position and direction data and a line-of-sight direction in the image processing circuit 33 under the control of the controller 39 at the step S105.

The line-of-sight direction is a direction vertical to a monitor screen showing a plane of the tomographic parallel images 53 displayed on the monitor 14. The line-of-sight direction is preset.

A relationship between the slice 52 after the coordinates conversion and a monitor screen is shown as a sliced state shown in (c) of FIG. 5. The sliced state shown in (c) of FIG. 5 shows on the monitor 14 only one of the slices 52 having undergone coordinates conversion. However, FIG. 5 does not illustrate an example of a real screen displayed on the monitor 14 but is an explanatory diagram illustrating the relationship between the slice 52 and the monitor screen.

Next, at a step S106, the controller 39 drives and controls the image processing circuit 34 to calculate a depth of pixels on the slice from the monitor screen.

The depth from the monitor screen is a distance between an assumed plane and each pixel on the slice. In this case, a plane corresponding to a position of the monitor screen is assumed in a space. Coordinates of the receive coil unit 44 of each pixel on the slice are calculated from the position and direction data. FIG. 5 shows in (d) a relationship between the assumed plane corresponding to a given monitor screen and pixels on the slice.

Pixels on the slice may be on a plane than the plane expressing the monitor screen in the line-of-sight direction according to settings of the assumed plane. However, in subsequent steps, the closer pixels are processed as "pixels having negative depth". Here, for convenience of explanation, by assuming that the plane is sufficiently far away from a first slice, pixels on all slices are assumed to be deeper than the plane. Thus, depth is adopted for all of them in following descriptions.

When the calculation of the depth from the monitor screen at the step S106 has completed, the controller 39 drives and controls the image processing circuit 33 to compare depths of the pixels on the slices and stored values of Z-buffer cells, which will be described later, at a step S107.

The Z-buffer cell is a cell corresponding to each pixel on the monitor screen, as shown in the conceptual diagram of a Z-buffer in FIG. 6. The Z-buffer cell stores a depth from a monitor screen to a pixel on a slice.

Each of the Z-buffer cells stores a storable maximum value as an initial value. In other words, an initial value of each Z-buffer cell is set deepest.

The image processing circuit 33 compares a depth of each pixel on the slice from the monitor screen and a value stored in a respective Z-buffer cell and calculates a large-small relationship with respect to the value.

Next, at a step S108, in accordance with the comparison between the pixel depth and the Z-buffer cell storing value at the step S107, the controller 39 performs a following process.

(I) If "the depth of a pixel<a value stored in the Z-buffer cell", (a) The image processing circuit 33 updates the value stored in the Z-buffer cell to the depth of the pixel on the slice.

In other words, the hand scanning is continued, and the serial plural slices 52 are obtained through steps, which will be described below. Then, each Z-buffer cell stores a depth of a shallowest pixel immediately under pixels on the monitor screen among pixels on the plural slices from the monitor screen.

(b) The image processing circuit 33 alternatively updates the value stored in a display cell, which will be described later, to a luminance value of a pixel on the slices 52.

As shown in FIG. 7, which is a conceptual diagram of an area storing monitor screens of the image memory 32, the area of the image memory 32 includes cells (called display cell, hereinafter) corresponding to pixels, respectively, on a monitor screen. The display cell stores a luminance value to be displayed by the monitor 14.

In this way, when a given pixel on the slice 52 compared at the step S107 is shallowest, the image processing circuit 33 updates the value stored in the display cell to the luminance value. Therefore, when the hand scanning is continued and the serial plural slices 52 are obtained through steps, which will be described, each display cell stores a luminance value of a shallowest pixel immediately under the pixels on the monitor screen among pixels on the plural slices.

(II) If "the depth of a pixel≧a value stored in the Z-buffer cell", the image processing circuit 33 does not perform any processing.

In other words, when the hand scanning is continued, and the serial plural slices 52 are obtained through steps, which will be described later, the image processing circuit 33 sequentially overlays the slices 52 to the closer side in the line-of-sight direction. This state is shown as the relationship state between a plane corresponding to the monitor screen and each pixel on the slices in (d) of FIG. 5. In the relation state in (d) of FIG. 5, pixels on the left side with respect to the line of intersection of the newest slice and an old slice among pixels on the newest slice are mainly shallower than the old slice. On the other hand, the pixels on the right side are mainly deeper than the old slice.

Therefore, the pixels on the left side on the newest slice appear to an operator to be overwritten on the tomographic parallel images. The tomographic parallel images 53 created in this way are shown as tomographic parallel images shown in (e) of FIG. 5.

Next, at a step S109, the controller 39 controls the monitor 14 to display side by side the newest ultrasonic tomographic image and the newest tomographic parallel images.

A display example including the ultrasonic tomographic image and the tomographic parallel images on the monitor screen is shown in FIG. 8. In FIG. 8, the ultrasonic tomographic image 51 is displayed on the right while the tomographic parallel images 53 are displayed on the left. A receive coil unit marker 56 is displayed near the tomographic parallel images 53. The receive coil unit marker 56 indicates a direction of the rectangular parallelepiped receive coil unit 44. When the monitor 14 displays up to the step S109 the old ultrasonic tomographic image 51 and the tomographic parallel images 53 in which the old slices 52 are piled, the monitor screen is updated.

At a step S110, the controller 39 terminates radial scanning when an operator inputs an instruction for terminating the hand scanning through the keyboard 15 and/or the mouse 16. Otherwise, the processing returns to the steps S103.

More specifically, when the operator selects one of different items in a menu and instructs to terminate the hand scanning by using the keyboard 15 and/or the mouse 16, the image constructing circuit 31 terminates outputting an exciting signal based on the instruction from the controller 39. Thus, the driving of the rotation of the motor 22 is terminated, and the radial scanning is terminated. In this way, as far as an operator instructs the termination of the hand scanning, the processing from the step S103 to the step S110 are repeated.

By repeating the processing at the steps S103 to S110, the tomographic parallel images 53 are sequentially extended as shown in the tomographic parallel images in (e) of FIG. 5 or as shown in tomographic parallel images in FIG. 8 in accordance with the hand scanning. Here, the ultrasonic tomographic image 51 in FIG. 8 is updated to the newest ultrasonic tomographic image in accordance with the hand scanning and is displayed.

When the tomographic parallel images 53 are about to lie off the monitor screen in accordance with the hand scanning, the image processing circuit 33 promptly scrolls the tomographic parallel images 53 before the display at the step S109 such that the newest slice 52 can be displayed entirely within the monitor screen.

Hand scanning for generating tomographic parallel images has been described above. Next, an operation after the hand scanning will be described.

An operator can select again an ultrasonic tomographic image to be displayed on the right side of a monitor screen from plural serial ultrasonic tomographic images 51 obtained through hand scanning. As shown in FIG. 9, the one slice 52 resulting from the slicing of the ultrasonic tomographic image 51 to be displayed on the right of the monitor screen is displayed in a different color, such as green, on the tomographic parallel images 53 for distinction. The slice displayed in a different color is called an ultrasonic tomographic image marker 55, hereinafter.

An operator can instructs selectively and sequentially to move the ultrasonic tomographic image marker 55 from the external input control circuit 37 to the adjacent slice 52 by using the keyboard 15 and/or the mouse 16. The display color of the slice 52 of the tomographic parallel images 53, which is indicated by the instruction for moving the ultrasonic tomographic image marker 55, is changed to green. Then, the slice 52 originally having the ultrasonic tomographic image marker 55 instructed to move is returned to a slice of an ultrasonic tomographic image in a same color as the other uninstructed plural slices, that is, in black and white. Then, the ultrasonic tomographic image 51 on which the indicated slice 52 is based is displayed on the right side of the monitor screen.

In other words, in connection with the selective movement of the ultrasonic tomographic image marker 55 in the tomographic parallel images on the monitor screen to the position of a desired slice 52, the ultrasonic tomographic image 51 is updated and is displayed.

Referring to the flowchart in FIG. 10, the operation will be further described in detail. The processing in FIG. 10 is performed under the control of the controller 39 in accordance with an instruction for moving an ultrasonic tomographic marker from the keyboard 15 and/or the mouse 16.

First of all, an operator selects an item for moving an ultrasonic tomographic image marker from different items in a menu by using the keyboard 15 and/or the mouse 16. At a step S201, the controller 39 receives through the external input control circuit 37 an instruction for moving the ultrasonic tomographic image marker 55 to the position of the adjacent slice 52. At a step S202, the controller 39 controls and drives the image processing circuit 33 and substitutes 1 for a variable n of a counter provided in the image processing circuit 33.

Next, at a step S203, the controller 39 causes the image processing circuit 33 to read the $n^{th}$ ultrasonic tomographic image and the position and direction data among the plural serial ultrasonic tomographic images 51 stored in the image memory 32. At a step S204, the image processing circuit 33 slices the read $n^{th}$ ultrasonic tomographic image 51 and creates slices 52. The creation of the slices at the step S204 is the same process as the process at the step S104 in FIG. 3, and the detail description will be omitted here.

When the slices 52 of the ultrasonic tomographic image 51 are created at the step S204, the controller 39 controls at the S205 the driving of the image processing circuit 33 and judges whether or not the read $n^{th}$ ultrasonic tomographic image is the ultrasonic tomographic image which is the base of the slice to which the ultrasonic tomographic image marker 55 is moved by being instructed at the step S201. If the $n^{th}$ ultrasonic tomographic image is determined as the ultrasonic tomographic image, the processing jumps to a step S206. If not, the processing jumps to a step S208.

At the step S205, if it is determined that the read $n^{th}$ ultrasonic tomographic image is the newly indicated ultrasonic tomographic image that the ultrasonic tomographic image marker 55 is moved to, the controller 39 at a step S206 drives and controls the image processing circuit 33 to update the ultrasonic tomographic image displayed on the right side of the monitor screen to the $n^{th}$ ultrasonic tomographic image. At a step S207, a slice of the $n^{th}$ ultrasonic tomographic image is colored green. In other words, the slice of the $n^{th}$ ultrasonic tomographic image is the new ultrasonic tomographic image marker 55 now.

Next, at the step S208, the controller 39 control the image processing circuit 33 to perform coordinates conversion of the slices based on the position and direction data and the line-of-sight direction like the step S105. At a step S209, the image processing circuit 33 calculates the depths of the pixels from the monitor screen to the slice like the step S106. At a step S210, the image processing circuit 33 compares the depths of the pixels on the slice and the values stored in respective Z-buffer cells like the step S107. Furthermore, at a step S211, like the step S108, the image processing circuit 33 performs a process in accordance with the comparison between the depths of the pixels and the values stored in the Z-buffer cells.

Next, at a step S212, the controller 39 updates and displays the ultrasonic tomographic image 51 and the newly created tomographic parallel images 53 to be displayed on the monitor 14 side by side as shown in FIG. 9.

When the display update for the monitor 14 has completed at the step S212, the controller 39 at a step S213 judges whether a process for reading all of the plural serial ultrasonic tomographic images obtained by hand scanning has completed or not. If the reading process has not completed, a step S214 and subsequent steps are performed. More specifically, if n is the last image of the plural serial ultrasonic tomographic images obtained by hand scanning, the controller 39 causes the image processing circuit 33 to complete all of the above-described processing. If n is not the last image of the plural serial ultrasonic tomographic images, the image processing circuit 33 is caused to add 1 to the variable n provided as a counter at a step S214. Then, the processing jumps to the step S203, and the processing from the step S203 to the step S214 is repeated.

As described above, by performing the processing from the step S201 to the step S214, the ultrasonic tomographic image marker 55 is moved to the position of the adjacent slice 52. In connection therewith, the ultrasonic tomographic image 51 is updated and is displayed.

An operator repeats the instruction performed at the step S201 by using the keyboard 15 and/or the mouse 16 so that the ultrasonic tomographic image marker 55 on the tomographic parallel images 53 can be selectively moved to the position of a desired slice 52. In connection therewith, the desired ultrasonic tomographic image 51 can be displayed.

At the initial state, that is, immediately after hand scanning, the monitor 14 displays the tomographic parallel images 53 along the scanning path 54 by the hand scanning and the newest obtained ultrasonic tomographic image 51 as shown in FIG. 8. Here, FIG. 8 does not show the ultrasonic tomographic image marker 55. This is because the ultrasonic tomographic image marker 55 appears when an operator first instructs to move the ultrasonic tomographic image marker 55 to a position of the adjacent slice 52 at the step S201.

Next, as shown in FIG. 11, when an instruction is given for driving the rotation of a receive coil unit marker 56 of the monitor screen, the tomographic parallel images 53 can be rotated in connection with the rotation of the receive coil unit marker 56. The rotational operation of tomographic parallel images will be described with reference to FIG. 12. The processing in FIG. 12 is performed under the control of the controller 39 in accordance with an instruction for a line-of-sight (rotation) from the keyboard 15 and/or the mouse 16.

At a step S301, an operator inputs an instruction for rotating the receive coil unit marker 56 by using the keyboard 15 and/or the mouse 16. Then, the instruction is input to the controller 39 through the external input control circuit 37. Then, through the display circuit 34, the receive coil unit marker 56 displayed on the monitor 14 is rotated in the direction indicated by the arrow in FIG. 11, and the tomographic parallel images 53 are also rotated in connection thereto. This state is checked on the monitor 14 by the operator. The rotation of the tomographic parallel images 53 is set such that the rotation in a new line-of-sight direction can be a direction from the closer side to the deep side in FIG. 11 by regarding the receive coil unit marker 56 as the receive coil unit 44.

At the step S301, after the line-of-sight direction of the tomographic parallel images 53 is set by using the receive coil unit marker 56, the processing from a step S302 to a step S314 is performed. Since the processing from the step S302 to the step S314 are the same as the steps S202 to S214, the description thereof will be omitted here.

In other words, the image processing circuit 33 reads from the image memory 32 the plural serial ultrasonic tomographic images 51 resulting from hand scanning. Then, the image processing circuit 33 can construct new tomographic parallel images 53 in the set new line-of-sight direction.

In this description, the tomographic parallel images 53 are rotated after the operator rotates the receive coil unit marker. However, the rotated tomographic parallel images 53 can be re-constructed every time the receive coil unit marker 56 slightly rotates if the processing by the controller 39, bus 38, image processing circuit 33, display circuit 34 and so on is fast enough. In this case, it appears to an operator that the receive coil unit marker 56 and the tomographic parallel images 53 rotate in connection with each other simultaneously.

Next, an operation for changing a position of slicing the ultrasonic tomographic image 51 will be described. As shown in FIG. 13, a slicing line marker 57 is displayed on the ultrasonic tomographic image 51 displayed on the monitor screen. Then, a new slicing position is defined by moving the slicing line marker 57 in accordance with an input of an instruction via the keyboard 15 and/or the mouse 16. Thus, the tomographic parallel images 53 of the slice 52 resulting from the slicing at the new slicing position are created.

The operation for changing the slicing position will be described with reference to the flowchart in FIG. 14. The processing in FIG. 14 is performed under the control of the controller 39 in accordance with an instruction for a slicing position from the keyboard 15 and/or the mouse 16.

At a step S401, an operator selects an item for changing a slicing position on the menu from the external input control circuit 37 to the controller 39 by using the keyboard 15 and/or the mouse 16. Then, the controller 39 controls the image processing circuit 33 and the display circuit 34 to display the slicing line marker 57 on a segment of the ultrasonic tomographic image 51 on the right side of a monitor screen shown in FIG. 13. When the operator instructs to move the slicing line marker 57 via the keyboard 15 and/or the mouse 16, the slicing marker 57 moves in the direction indicated by the arrow in FIG. 13, for example, in accordance with the instruction. The state is checked by an operator on the monitor, and the slicing position is defined at the position of the newly moved slicing line marker 57.

When the setting for moving a slicing line marker position at the step S401 has completed, the processing from a step S402 to a step S414 are performed. Since the processing from the step S402 to the step S414 is the same as the processing at the step S202 to S214, the detail description will be omitted here. In other words, the image processing circuit 33 reads from the image memory the plural serial ultrasonic tomographic images resulting from hand scanning. Then, the image processing circuit 33 can construct the tomographic parallel images 53 of a slice resulting from the slicing at a defined new slicing position. The tomographic parallel images 53 are updated and displayed at the new slicing position in connection with the movement of the slicing position marker 57.

In this description, the tomographic parallel images 53 are re-constructed after the operator moves the slicing line marker 57. However, the rotated tomographic parallel images 53 can be re-constructed every time the slicing line marker slightly moves if the processing by the controller 39, bus 38, image processing circuit 33, display circuit 34 and so on is fast enough. In this case, it appears to an operator that the slicing line marker 57 and the tomographic parallel images 53 vary in connection with each other simultaneously.

The slicing line marker 57 is displayed in a different color such as green from the color of the background so as to be distinctive when an image of the background is black and white.

As described above, since the tomographic parallel images 53 are displayed during hand scanning, the density of an image can be easily recognized with respect to which part of a body cavity of a subject and how many images are picked up. Therefore, unexpected failures in picking up images may hardly occur.

Since the newest ultrasonic tomographic image 51 and the tomographic parallel images 53 are displayed on the right and left sides, respectively, on the monitor screen during the hand scanning, which part is scanned for an ultrasonic tomographic image displayed on the current screen can be easily recognized. For example, when the insert portion 21 of the ultrasonic endoscope 11a is inserted and/or withdrawn along the digestive tract from the esophagus to the duodenum through the stomach, the locus substantially and anatomically agrees with the form of the digestive tract. By using the fact, an operator can clearly identify which part within a body cavity the distal end of the insert portion of the ultrasonic endoscope exists based on the tomographic parallel images.

After the hand scanning, a slice expressing the ultrasonic tomographic image displayed on the monitor screen has a different color as an ultrasonic tomographic image marker from that of the other slices. Thus a correspondence between the ultrasonic tomographic image and the tomographic parallel images can be expressed. Therefore, which part of a curved or bent lumen is scanned to obtain the ultrasonic tomographic image can be easily recognized. As a result, a desired ultrasonic tomographic image can be easily obtained, and an area of concern such as a lesion can be easily rendered and discovered.

Furthermore, an ultrasonic tomographic image marker on topographic parallel images is moved by using input means such as a keyboard and a mouse, and an ultrasonic tomographic image is updated in connection therewith. Thus, the tomographic parallel images can be used as a guide for searching an ultrasonic tomographic image. In addition, since an ultrasonic tomographic image is updated by moving an ultrasonic tomographic image marker little by little. Thus, connections among internal organs and the travel of vessels can be easily understood. Also, a spatial positional relationship between a lesion and surrounding organs can be more easily understood.

The image processing circuit creates tomographic parallel images by slicing an ultrasonic tomographic image and overwriting the shallowest pixel on a slice thereof. Thus, when a slicing position crosses a lesion, an organ and/or a vessel, a connection of lesions, connection of organs and travel of vessels along hand scanning can be recognized at a glance. By rotating tomographic parallel images, the tomographic parallel images can be observed in a direction that the connection of lesions, connection of organs and travel of vessels along hand scanning can be further easily understood. Furthermore, a slicing position is adjusted and operated to be changed on an ultrasonic tomographic image by using an input unit such as a keyboard and a mouse. Thus, tomographic parallel images including a lesion, an organ and/or a vessel at the slicing position can be easily created.

A receive coil unit marker indicating a direction of a receive coil unit is provided near tomographic parallel images. Thus, a direction of the observation of the tomographic parallel images can be further easily understood, and the direction of hand scanning can be further easily understood.

Tomographic parallel images are created by slicing an ultrasonic tomographic image and overwriting the shallowest pixel every time the ultrasonic tomographic image is constructed during hand scanning. Thus, processing such as interpolating processing required for constructing a three-dimensional image is not necessary, and tomographic parallel images can be created and be updated fast. In addition, while an operator performs hand scanning, and the operator can observe live tomographic parallel images along hand scanning.

Therefore, an ultrasonic diagnostic apparatus according to the first embodiment may be used to easily and realistically observe an extension of an invasion along a lumen of a lesion, a depth of a vertical invasion from a surface of a lumen and a spread and depth of an invasion to an organ and/or a portal vein in a deeper part from a lumen by moving a radial scan type ultrasonic endoscope within a body cavity.

In the description of the first embodiment of the ultrasonic diagnostic apparatus according to the invention, tomographic parallel images are re-constructed by moving a slicing line marker on the tomographic parallel images. However, the slicing line marker may be fixed, and tomographic parallel images may be moved in parallel or be rotated within a monitor screen.

The hand scanning may be performed in any one direction between a direction that the insert portion of the ultrasonic endoscope is withdrawn from a deep part of a body cavity or a direction that the insert portion is inserted to the deep part within the body cavity.

In the description above, an ultrasonic tomographic image and tomographic parallel images are displayed on the monitor screen simultaneously. However, an ultrasonic tomographic image and tomographic parallel images may be displayed separately on separate monitors, respectively. Alternatively, an ultrasonic tomographic image and tomographic parallel images may be alternately switched and displayed on a single monitor screen.

In the description above, displaying an ultrasonic tomographic image and tomographic parallel images thereof after the hand scanning uses the ultrasonic tomographic image and position and direction data stored in an image memory. However, the ultrasonic tomographic image and the position and direction data may be recorded in a three-dimensional data recording portion instead of an image memory immediately after the hand scanning, and the ultrasonic tomographic image and tomographic parallel images recorded in the three-dimensional data recording portion may be used after the hand scanning.

In the description above, the ultrasonic tomographic image marker is a slice corresponding to ultrasonic tomographic image displayed on the right side of a monitor screen and having a different display color from that of the other slices. However, a specific slice may be distinguished in any display form. For example, an ultrasonic tomographic image marker may have a different luminance instead of a different color. Alternatively, an ultrasonic tomographic image marker may have a specific mark such as a circle or a square on a slice corresponding to an ultrasonic tomographic image displayed on the right side of a monitor screen. Alternatively, an ultrasonic tomographic image marker may be a slice having a frame in a specific color corresponding to an ultrasonic tomographic image displayed on the right side of a monitor screen.

In the description above, a send coil is provided at the distal end of the insert portion of the ultrasonic endoscope while the receive coil is fixed in a space. However, the send coil and the receive coil may be provided oppositely.

Furthermore, in the description above, the position and direction of an ultrasonic tomographic image are detected by using a magnetic field thereof. However, apparently, another means for detecting a position and a direction may be provided.

Figure 15:
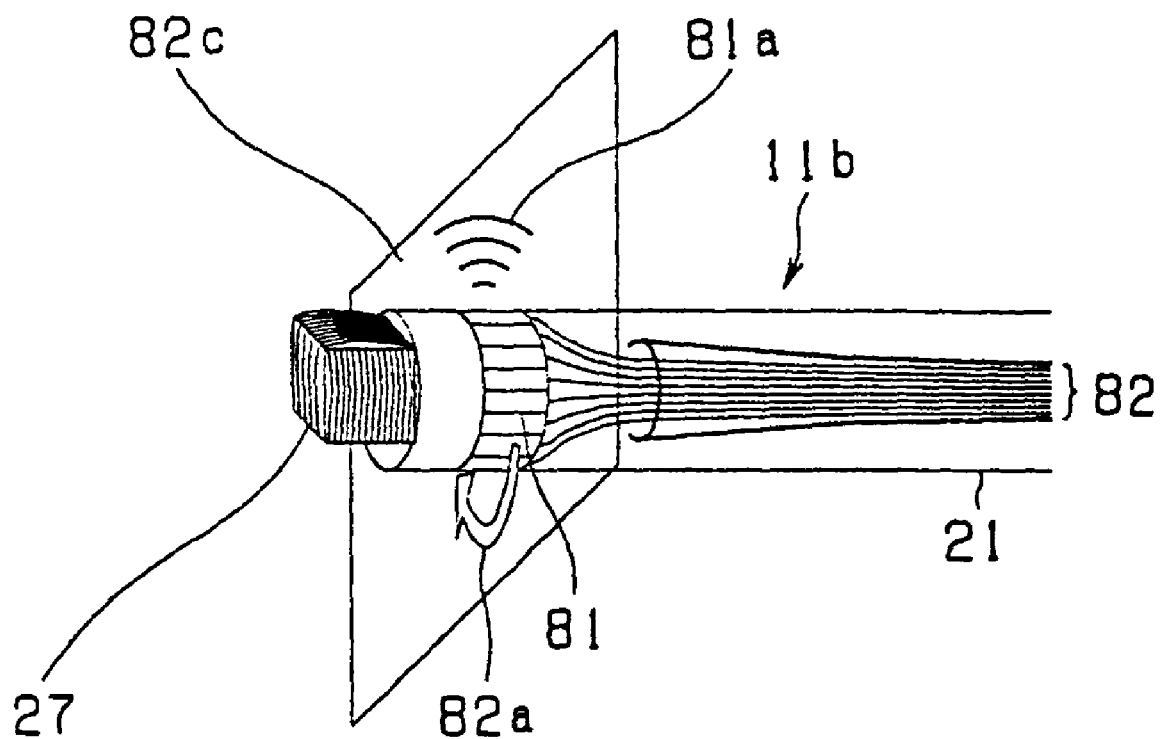
FIG. 15 is a block diagram showing a configuration of a distal end of an insert portion of an ultrasonic endoscope used in an ultrasonic diagnostic apparatus according to a second embodiment of the invention.
Figure 16:
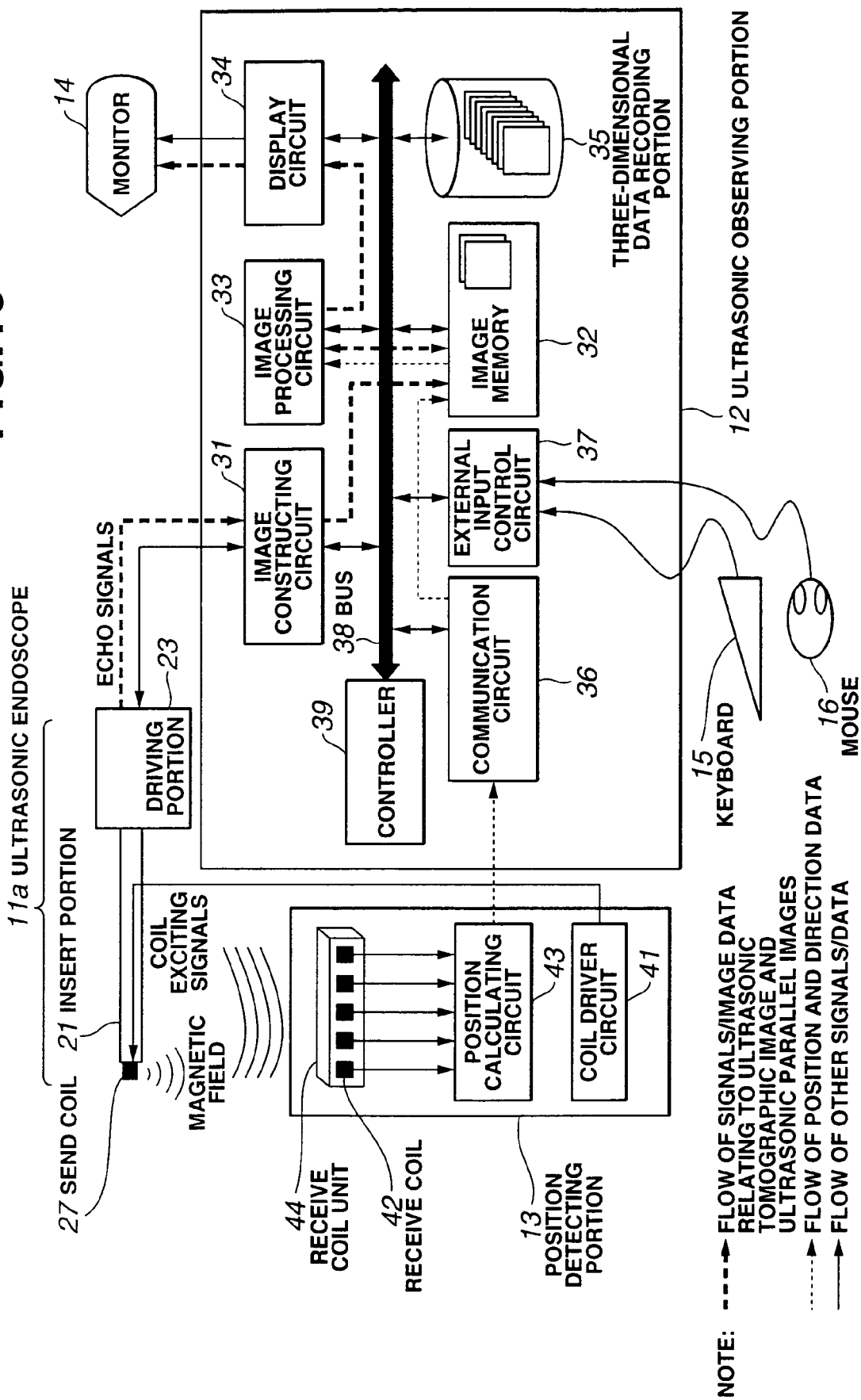
FIG. 16 is a block diagram showing an entire configuration of the ultrasonic diagnostic apparatus according to the second embodiment.

Next, a second embodiment of an ultrasonic diagnostic apparatus according to the invention will be described with reference to FIGS. 15 and 16. FIG. 15 is a block diagram showing a configuration of a distal end of an insert portion of an ultrasonic endoscope to be used in an ultrasonic diagnostic apparatus according to the second embodiment of the invention. FIG. 16 is a block diagram showing an entire configuration of the ultrasonic diagnostic apparatus according to the second embodiment. The same reference numerals are given to the same components in FIGS. 1 and 2, and the detail descriptions thereof will be omitted here.

An ultrasonic transducer array 81 is provided at a distal end of an insert portion 21 of an ultrasonic endoscope 11b to be used in an ultrasonic diagnostic apparatus according to the second embodiment. The ultrasonic transducer array 81 is produced by slicing an ultrasonic transducer into rectangular pieces, and the pieces are arranged as a ring-shaped array around the insert portion 21 in the axis direction. The ultrasonic transducers included in the ultrasonic transducer array 81 are connected to an image constructing circuit 31 of an ultrasonic observing portion 12 through a signal line 82 and a driving portion 23.

The ultrasonic transducer array 81 is of a so-called electronic radial scan type in which a ring-shaped array is sequentially switched and driven from the image constructing circuit 31 via the driving portion 23, and an ultrasonic beam 81a is oscillated thereby such that a radial scanning 82a can be performed electronically.

A part of or plural ultrasonic transducers among the ultrasonic transducers included in the ultrasonic transducer array 81 generate and output ultrasonic wave, which is a compressional wave of a medium, in response to an exciting signal in a pulse-voltage shape from the image constructing circuit 31 of the ultrasonic observing portion 12. In this case, the image constructing circuit 31 delays exciting signals such that the exciting signals can reach the ultrasonic transducers at different times. The delay is defined such that one ultrasonic beam 81a can be formed when ultrasonic waves excited by the ultrasonic transducers are overlapped within a body to be examined. The ultrasonic beam 81a is irradiated to the outside of the ultrasonic endoscope 11b, and reflected echo from the inside of a body to be examined is input to each of the ultrasonic transducers. Each of the ultrasonic transducers converts the reflected echo to an electric echo signal and outputs the echo signal to the image constructing circuit 31.

In order to perform the radial scanning 82a indicated by the arrow in FIG. 15 by using the ultrasonic beam 81a output from the ultrasonic transducer array 81, the image constructing circuit 31 re-selects plural ultrasonic transducers relating to the formation of the ultrasonic beam 81a and sends exciting signals again. Thus, the angle of the ultrasonic beam 81a is changed, and so-called radial scanning is performed.

In other words, the ultrasonic endoscope 11a according to the first embodiment of the present invention performs mechanical radial scanning in which the ultrasonic transducer 25 is rotated by the motor 22. On the other hand, the ultrasonic endoscope 11b according to the second embodiment selects and drives an ultrasonic transducer outputting the ultrasonic beam 81a from plural ultrasonic transducers in the ultrasonic transducer array 81 and performs electronic radial scanning, which is different from the first embodiment. The other configurations and operations are entirely the same.

Since mechanical radial scanning is adopted according to the first embodiment, a twist occurs in the flexible shaft 26. The twist causes ununiformity among plural ultrasonic tomographic images, and a distortion may occur on tomographic parallel images. This is because, in mechanical radial scanning, a position of a rotational angle of a motor is detected by a rotary encoder adjacent to the motor.

However, since a mechanical twist and/or an error may not occur when electronical radial scanning is adopted, no distortion occurs on tomographic parallel images.

Apparently, the electronic radial scanning according to the second embodiment may be 270° radial scanning, for example, as well as 360° radial scanning.

Figure 17:
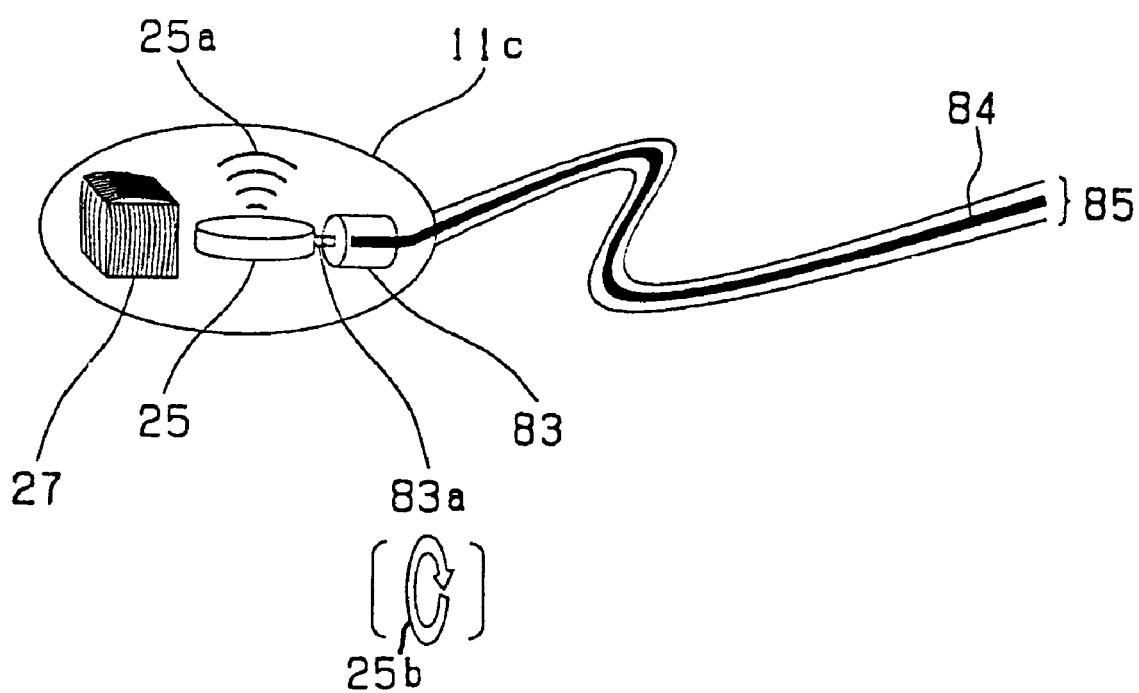
FIG. 17 is a block diagram showing a variation example of the ultrasonic endoscope used in the ultrasonic diagnostic apparatus according to the second embodiment.

Next, a variation example of the ultrasonic endoscope 11b used in an ultrasonic diagnostic apparatus according to the second embodiment will be described with reference to FIG. 17. FIG. 17 is a block diagram showing an ultrasonic endoscope according to this variation example.

The ultrasonic endoscope in the variation example shown in FIG. 17 is a capsule ultrasonic endoscope 11c in which an ultrasonic endoscope is stored in a capsule as a radial scan type ultrasonic probe.

The capsule ultrasonic endoscope 11c contains in the capsule the send coil 27, the ultrasonic transducer 25, a micromotor 83, and a rigid shaft 83a extending from a rotational axis of the micromotor 83 and holding and fixing the ultrasonic transducer 25.

A signal cable 85 extends from the capsule ultrasonic endoscope 11c. A signal line 84 of the signal cable 85 is connected to the ultrasonic transducer 25 as a signal of the micromotor 83 and is connected to the driving portion 23.

The micromotor 83 of the capsule ultrasonic endoscope 11c drives the rotation of the ultrasonic transducer 25 through the rigid shaft 83a. The rotational direction of the rigid shaft 83a is a direction of the radial scanning 25b of the ultrasonic transducer 25.

A rotational twist between the micromotor 83 and the ultrasonic transducer 25 may not occur easily when the micromotor 83 and the ultrasonic transducer 25 are brought closer by using the rigid shaft 83a. Thus, images with no distortion among ultrasonic tomographic images can be created by preventing a different between the rotation of the micromotor 83 and the rotation of the ultrasonic transducer 25.

The capsule ultrasonic endoscope 11c can be reduced in size since components such as an optical observation window, a CCD camera, a light guide fiber and a video-signal cable are not required. Thus, a load on a subject can be reduced when the subject swallows the capsule ultrasonic endoscope into his/her body cavity, and scanning in the body cavity can be easier. Therefore, an operator can easily recognize an observed position within the body cavity and can perform observation easily.

Furthermore, since the capsule ultrasonic endoscope 11c can be inserted or be withdrawn by natural swallowing, falling and writhing, hand scanning within a body cavity can be easier.

Figure 18A:
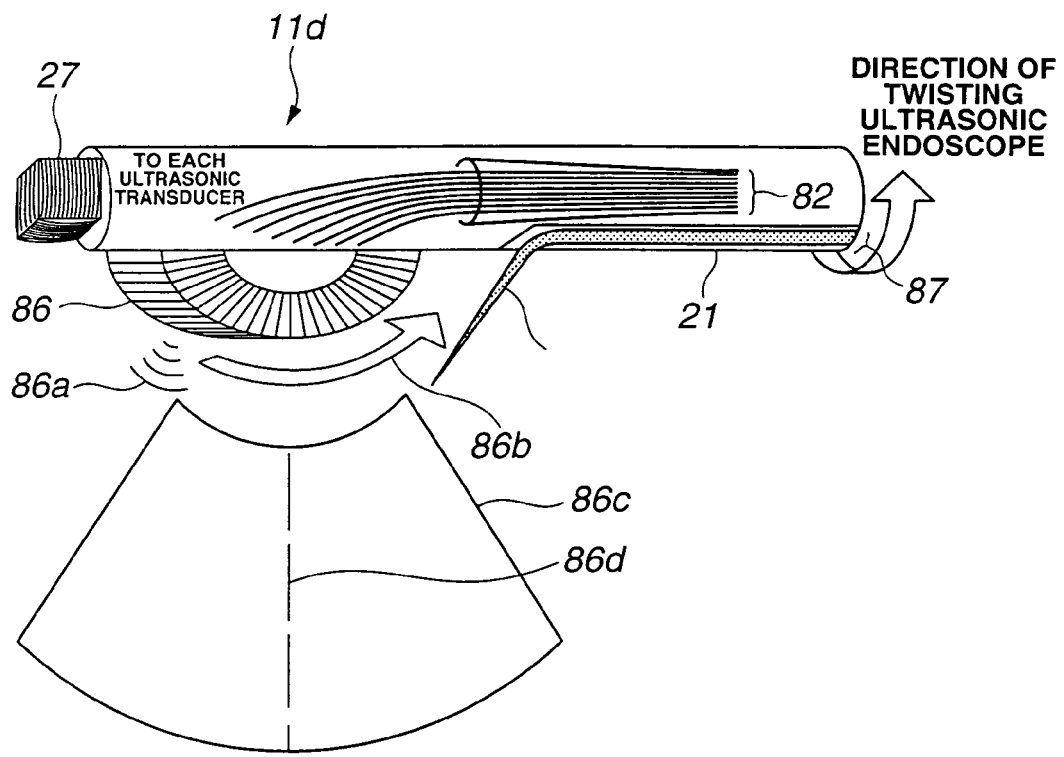
FIG. 18A is an explanatory diagram showing a configuration and operation of an ultrasonic endoscope according to a third embodiment applicable to an ultrasonic diagnostic apparatus according to the invention.
Figure 18B:
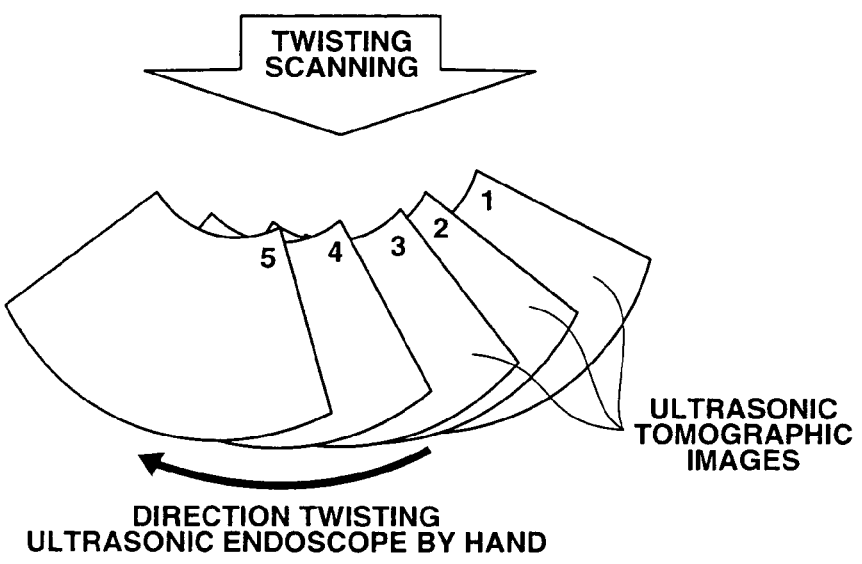
FIG. 18B is a diagram showing ultrasonic tomographic images resulting from twisting scanning by the ultrasonic endoscope in FIG. 18A.
Figure 19:
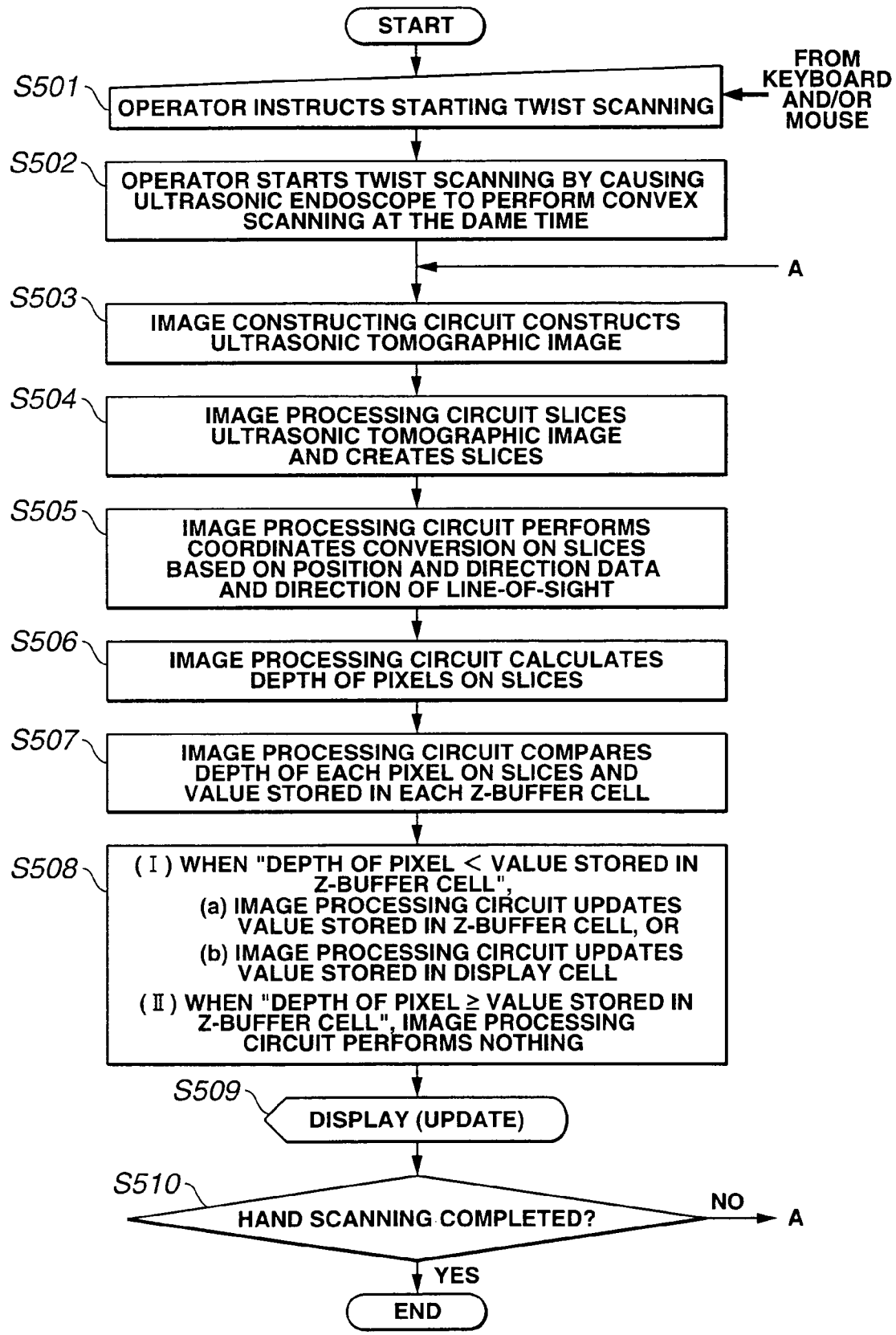
FIG. 19 is a flowchart describing an operation of the ultrasonic diagnostic apparatus to which the ultrasonic endoscope according to the third embodiment is applied.

Next, an ultrasonic endoscope according to a third embodiment to be applied to the ultrasonic diagnostic apparatus according to the invention will be described with reference to FIGS. 18A and 18B and FIG. 19. FIG. 18A is an explanatory diagram showing a configuration and operation of the ultrasonic endoscope according to the third embodiment. FIG. 18B is a diagram showing ultrasonic tomographic images resulting from twist scanning by the ultrasonic endoscope. FIG. 19 is a flowchart describing an operation of an ultrasonic diagnostic apparatus to which the ultrasonic endoscope according to the third embodiment is applied. A configuration of the ultrasonic diagnostic apparatus to which the ultrasonic endoscope according to the third embodiment is applied is common to that of the ultrasonic diagnostic apparatus according to the second embodiment in FIG. 16.

An ultrasonic endoscope 11d according to the third embodiment includes an ultrasonic transducer array 86 at the distal end of an insert portion 21. As shown in FIG. 18A, the ultrasonic transducer array 86 is produced by slicing an ultrasonic transducer into rectangular pieces, and the pieces are arranged in a substantial arc form in a direction that the ultrasonic transducers are inserted.

The ultrasonic transducers included in the ultrasonic transducer array 86 are connected to an image constructing circuit 31 of an ultrasonic observing portion 12 via a signal line 82 and a driving portion 23.

In order to perform different kinds of treatments by observing ultrasonic tomographic images at the same time, the ultrasonic endoscope 11d includes a channel 87, which is a through-hole into which a puncture needle and/or a forceps (not shown) is inserted through the insert portion.

In the ultrasonic endoscope 11d, ultrasonic wave, which is a compressional wave of a medium, is projected to a part of and plural ultrasonic transducers included in the ultrasonic transducer array 86 in response to an exciting pulse-voltage-shape signals from the image constructing circuit 31 of the ultrasonic observing portion 12.

When the ultrasonic wave is projected, the image constructing circuit 31 delays exciting signals such that the exciting signals to be supplied to the ultrasonic transducers can reach the ultrasonic transducers at different times. The delay is defined such that one ultrasonic beam 86a can be formed when ultrasonic waves excited by the ultrasonic transducers overlap within a body to be examined.

The ultrasonic beam 86a is irradiated to the outside of the ultrasonic endoscope 11d, and reflected echo from the inside of a body to be examined is input to each of the ultrasonic transducers. Each of the ultrasonic transducers converts the reflected echo to an electric echo signal and outputs the echo signal to the image constructing circuit 31.

In order to perform convex scanning 86b indicated by the shown arrow by using the ultrasonic beam 86a projected from the ultrasonic transducer array 86 of the ultrasonic endoscope 11d, the image constructing circuit 31 sequentially selects and sends the exciting signal to plural ultrasonic transducers.

Thus, the angle of the ultrasonic beam 86a projected from the ultrasonic transducer array 86 is changed, and so-called convex scanning is performed.

An ultrasonic tomographic image and tomographic parallel images can be created by using the ultrasonic endoscope 11d like the first to third embodiments.

An operation during twist scanning for creating tomographic parallel images during an ultrasonic diagnosis using the ultrasonic endoscope 11d will be described with reference to FIG. 19.

At a step S501, an operator inputs an instruction for displaying a menu having different items and selects an item for starting twist scanning from the menu via a keyboard 15 and/or a mouse 16. An exciting signal for driving the ultrasonic transducer array 86 is output from the controller 39 to the image constructing circuit 31, and convex scanning is started.

Next, at a step S502, the operator starts rotating (twists, hereinafter) the ultrasonic endoscope 11d within a body cavity of a body to be examined about the insert axis while convex scanning. By repeating the convex scanning with the twists at subsequent steps, ultrasonic tomographic images can be constructed sequentially. This scanning method is called "twist scanning", hereinafter. The state of the twist scanning is shown in FIG. 18B, and reference numerals 1 to 5 are given to ultrasonic tomographic images in order of the construction. For convenience of description, FIG. 18A shows a state where a puncture needle projects from a channel 87. However, during twist scanning, the puncture needle does not project.

Once the twist starts at the step S502, the controller 39 controls the image constructing circuit 31 to construct ultrasonic tomographic images based on echo signals from the ultrasonic transducer array 86 at a step S503. The constructed ultrasonic tomographic image and position and direction data calculated when the ultrasonic tomographic image is constructed are stored in the image memory 32 in synchronization and in connection with each other.

Next, at a step S504, the controller 39 controls the image processing circuit 33 to read the ultrasonic tomographic image and position and direction data stored in the image memory 32, slice the ultrasonic tomographic image 51 and create slices. A slicing position of the ultrasonic tomographic image from which the slices are created is preset. Here, for convenience of description of following steps, as shown in FIG. 18A, the ultrasonic tomographic image is sliced at a slicing position 86d of a straight line through the center of a convex scan plane 86c. The slicing position 86d may be changed or be newly set like the first embodiment.

When the creation of the slices at the step S504 ends, a step S505 and subsequent steps are performed. Here, since operations in the steps S505 to S510 are the same as those at the steps S105 to S110, the detail description will be omitted.

In other words, image processing circuit 33 reads plural serial ultrasonic tomographic images resulting from the twist scanning from the image memory 32 and constructs new tomographic parallel images in a newly set line-of-sight direction. By performing processing from the steps S503 to the step S510, tomographic parallel images are sequentially extended in accordance with the advance of the twist scanning.

When the tomographic parallel images are about to lie off the screen of the monitor 14 due to the twist scanning, the image processing circuit 33 prompts the scrolling of the tomographic parallel images before being displayed at the step S509 so that a newest slice can be displayed entirely within the monitor screen. An operation after the twist scanning is the same as the operation after the hand scanning.

With the convex scan type ultrasonic endoscope, an affected area is observed by using ultrasonic tomographic images thereof and, at the same time, a puncture needle is sticked into the affected area. Thus, cells and/or a tissue of the affected area can be sucked and be biopsied. The biopsied cells and/or tissue are called specimen and are pathologically examined under a microscope. Therefore, a disease of the affected area can be diagnosed and judged based on the specimen, which is significantly medically effective.

By using the convex scan type ultrasonic endoscope 11d, an operator can recognize a spread of a lesion to surrounding organs based on tomographic parallel images thereof and can stick the needle into the lesion with accuracy. Thus, the specimen can be extracted easily.

How blood vessels travel can be easily recognized before the sticking, and the travel of the blood vessel can be easily checked so as to avoid bleeding upon sticking. Thus, an examination time before the sticking can be saved.

As described above, the ultrasonic diagnostic apparatus according to the first to third embodiments and variations of the invention, ultrasonic images can be displayed on a monitor, from which an extension of an invasion along a lumen of a lesion, a vertical depth of an invasion from a surface of the lumen and a spread and depth of an invasion to an organ and/or a portal vein in a deeper part than a lumen can be observed. By displaying tomographic parallel images during scanning, the density of image pickup can be easily recognized with respect to which part of a body cavity of a subject and how may tomographic parallel images are displayed on the monitor screen. Therefore, an ultrasonic diagnostic apparatus preventing unexpected failures in picking up images can be advantageously provided.

Next, an ultrasonic diagnostic apparatus according to a fourth embodiment of the invention will be described with reference to FIGS. 20 to 32.

Figure 20:
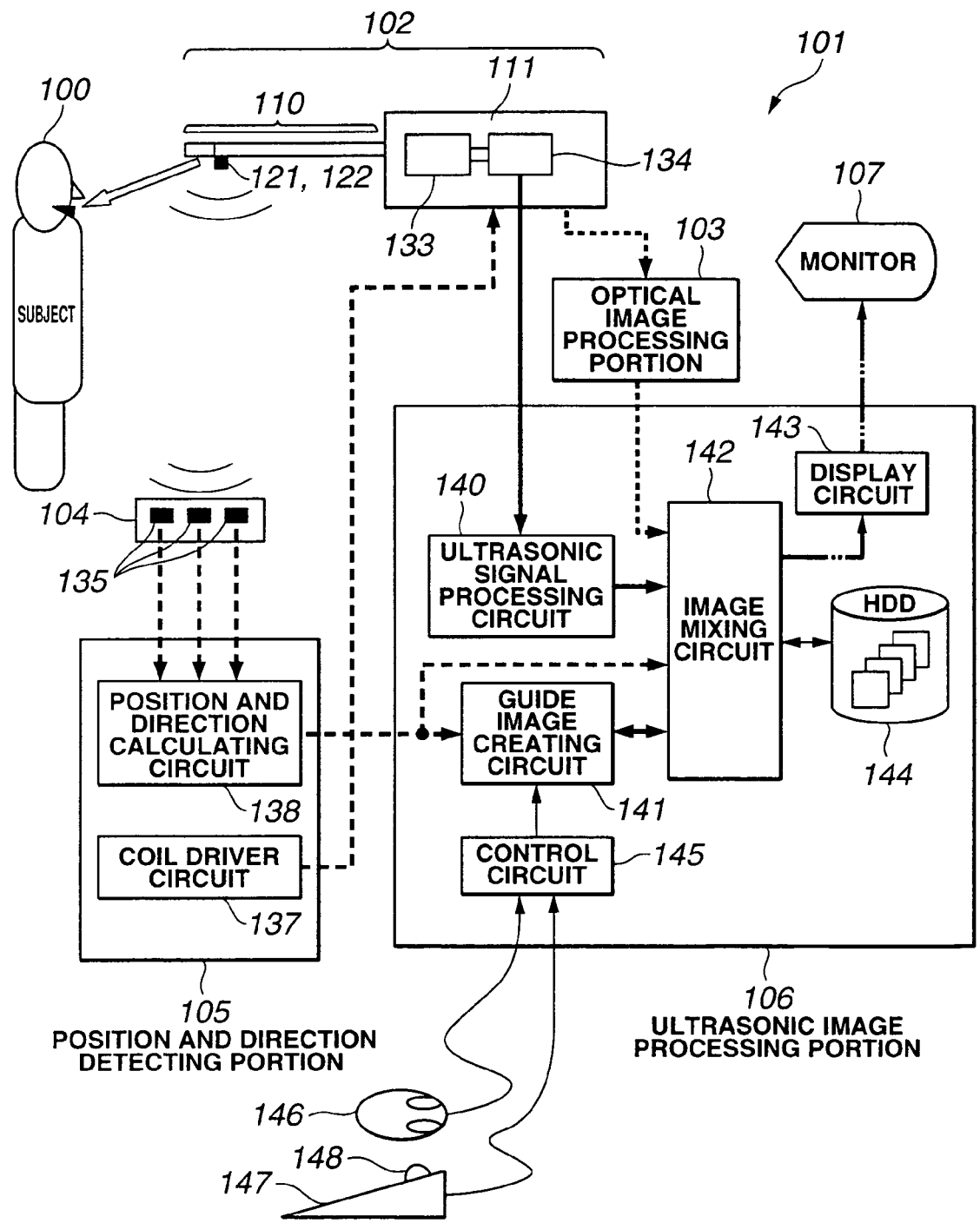
FIG. 20 is a schematic configuration diagram of an ultrasonic diagnostic apparatus according to a fourth embodiment of the invention.
Figure 21:
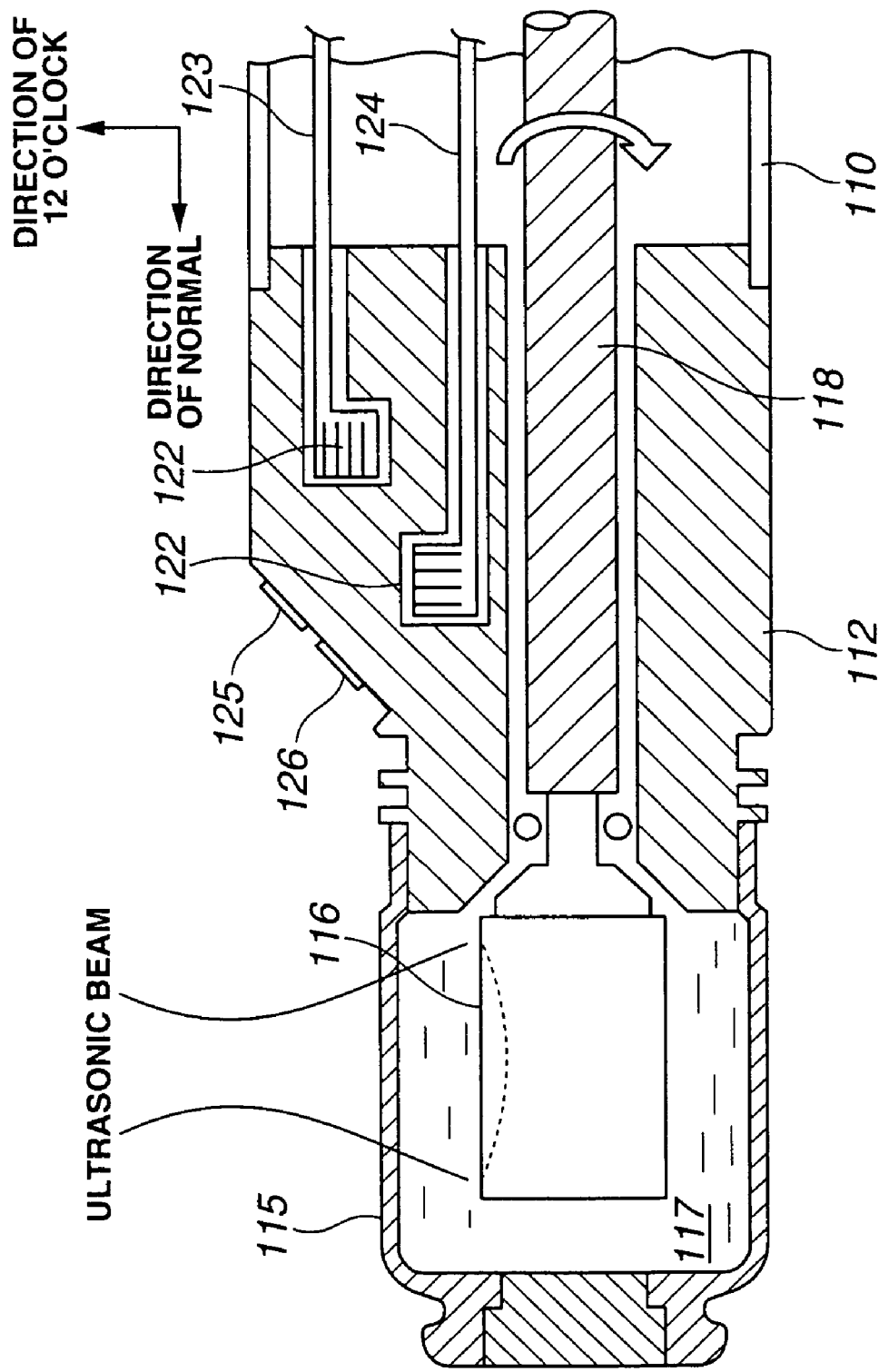
FIG. 21 is an enlarged sectional view of a distal end to be inserted of an insert port of an endoscope in the ultrasonic diagnostic apparatus according to the fourth embodiment.
Figure 22:
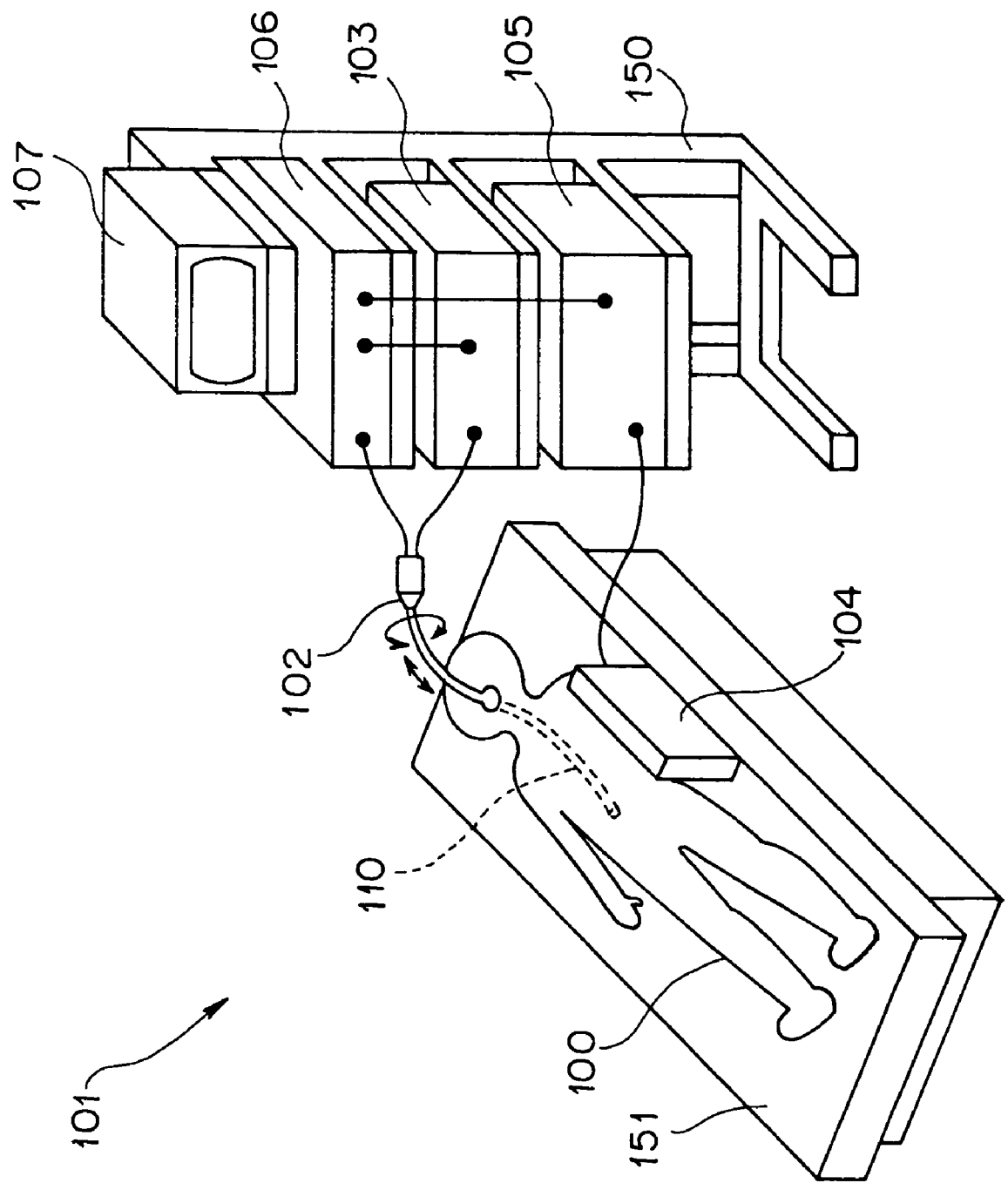
FIG. 22 is an external view in which the ultrasonic diagnostic apparatus according to the fourth embodiment is used to a body to be examined.
Figure 23:
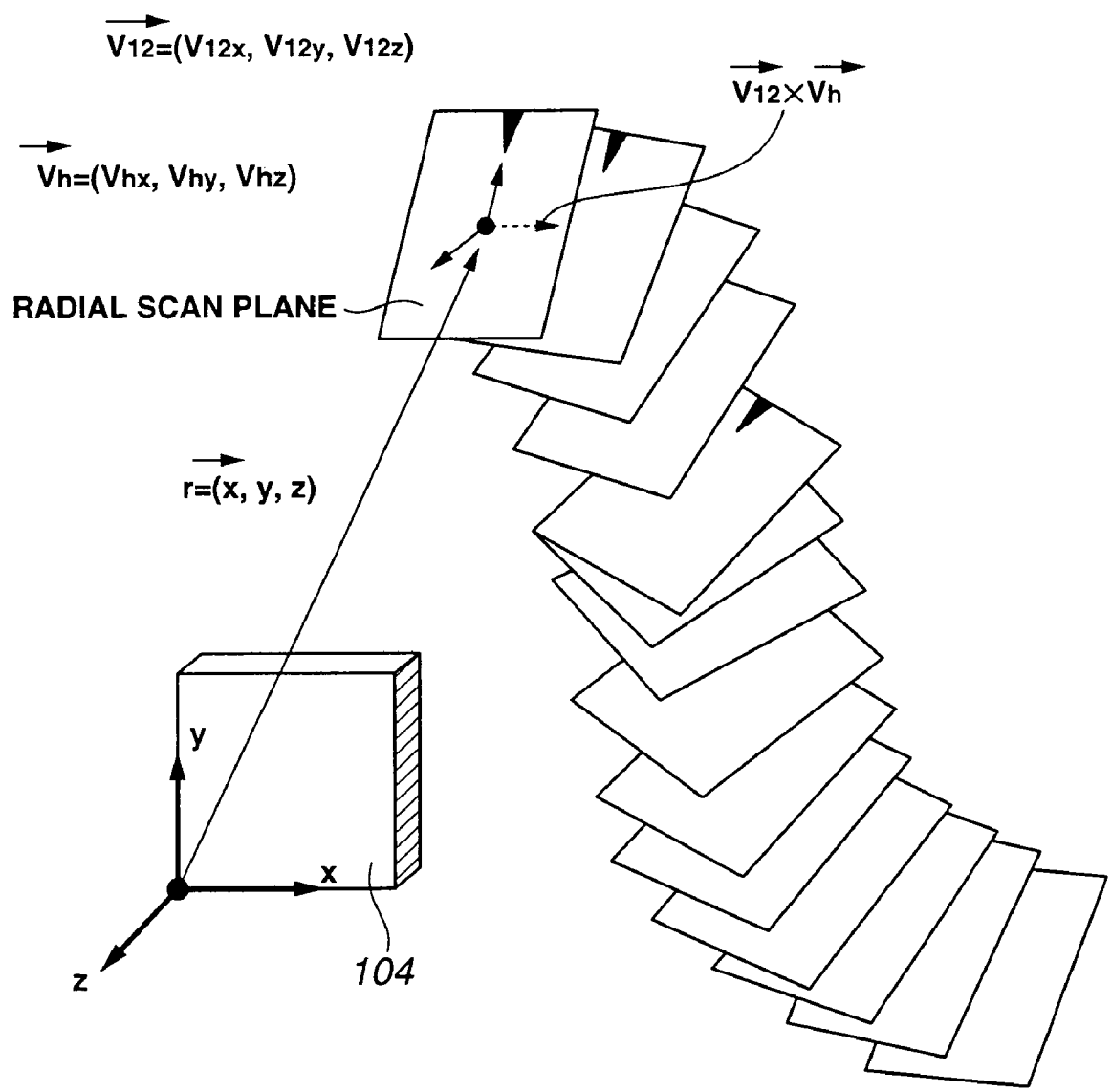
FIG. 23 is a conceptual diagram of data for describing position and direction data in the ultrasonic diagnostic apparatus according to the fourth embodiment.
Figure 24:
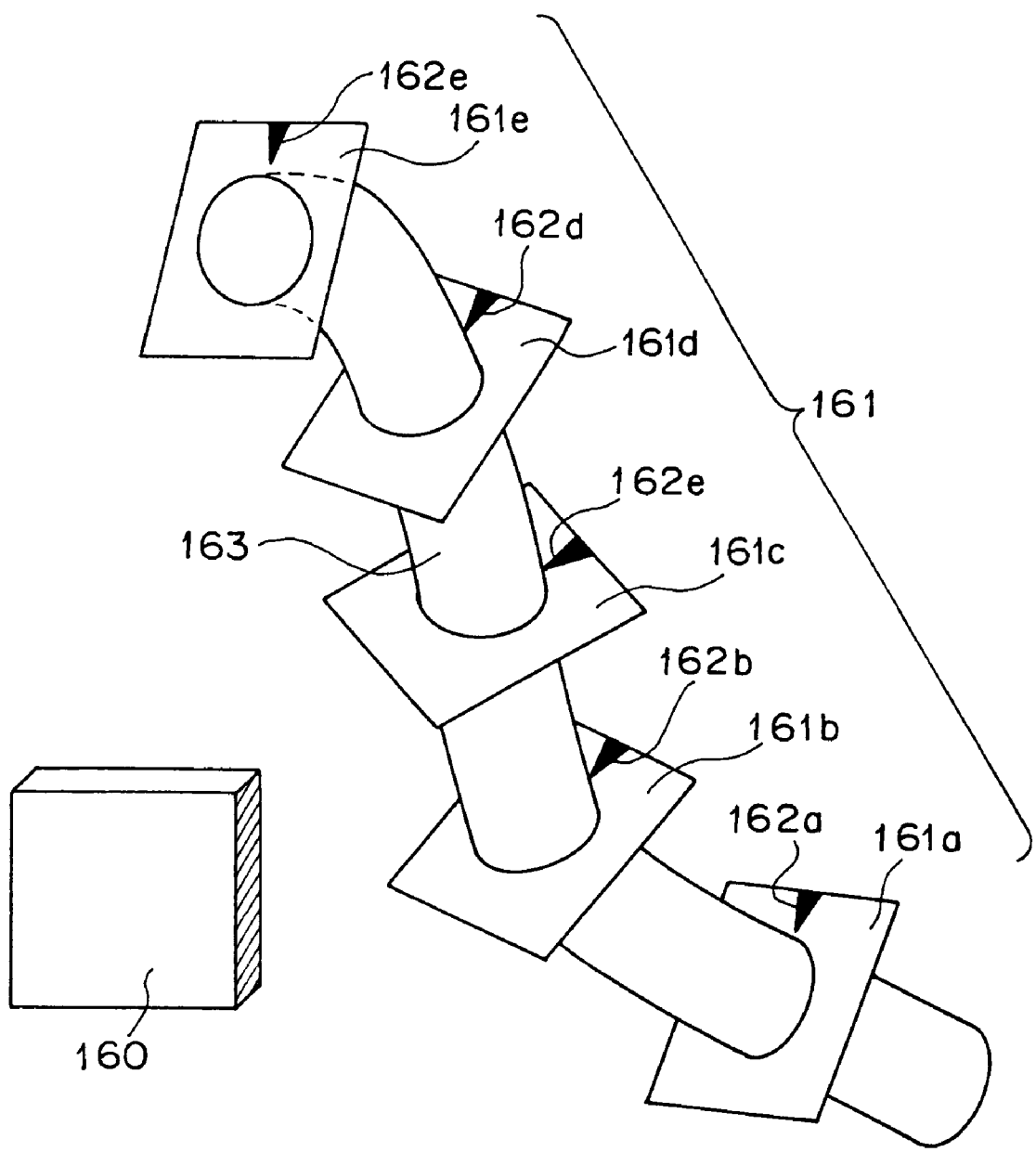
FIG. 24 is an explanatory diagram showing an ultrasonic guide image in the ultrasonic diagnostic apparatus according to the fourth embodiment.
Figure 31:
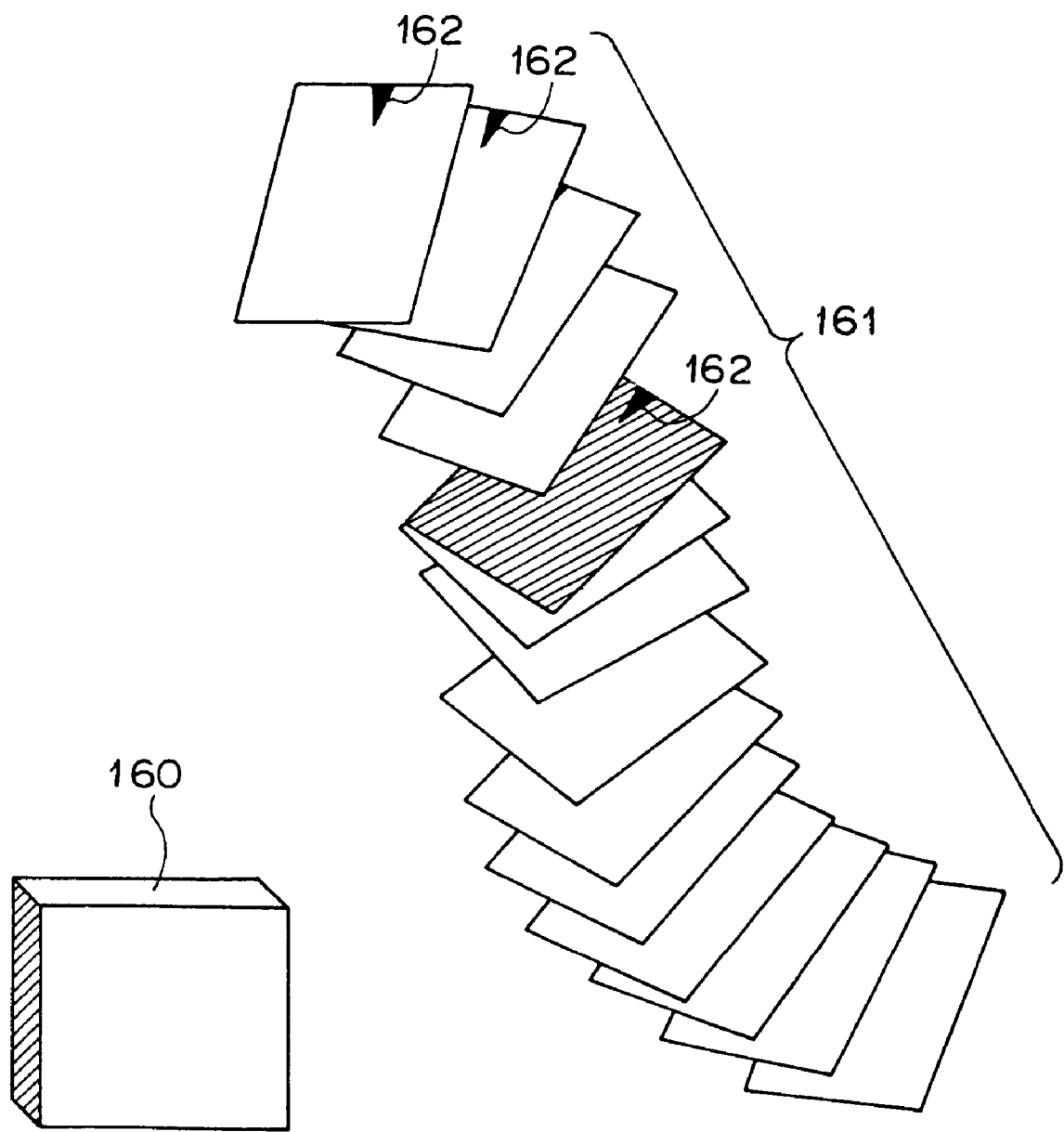
FIG. 31 is an explanatory diagram showing a variation example of a guide image in the ultrasonic diagnostic apparatus according to the fourth embodiment.
Figure 32:
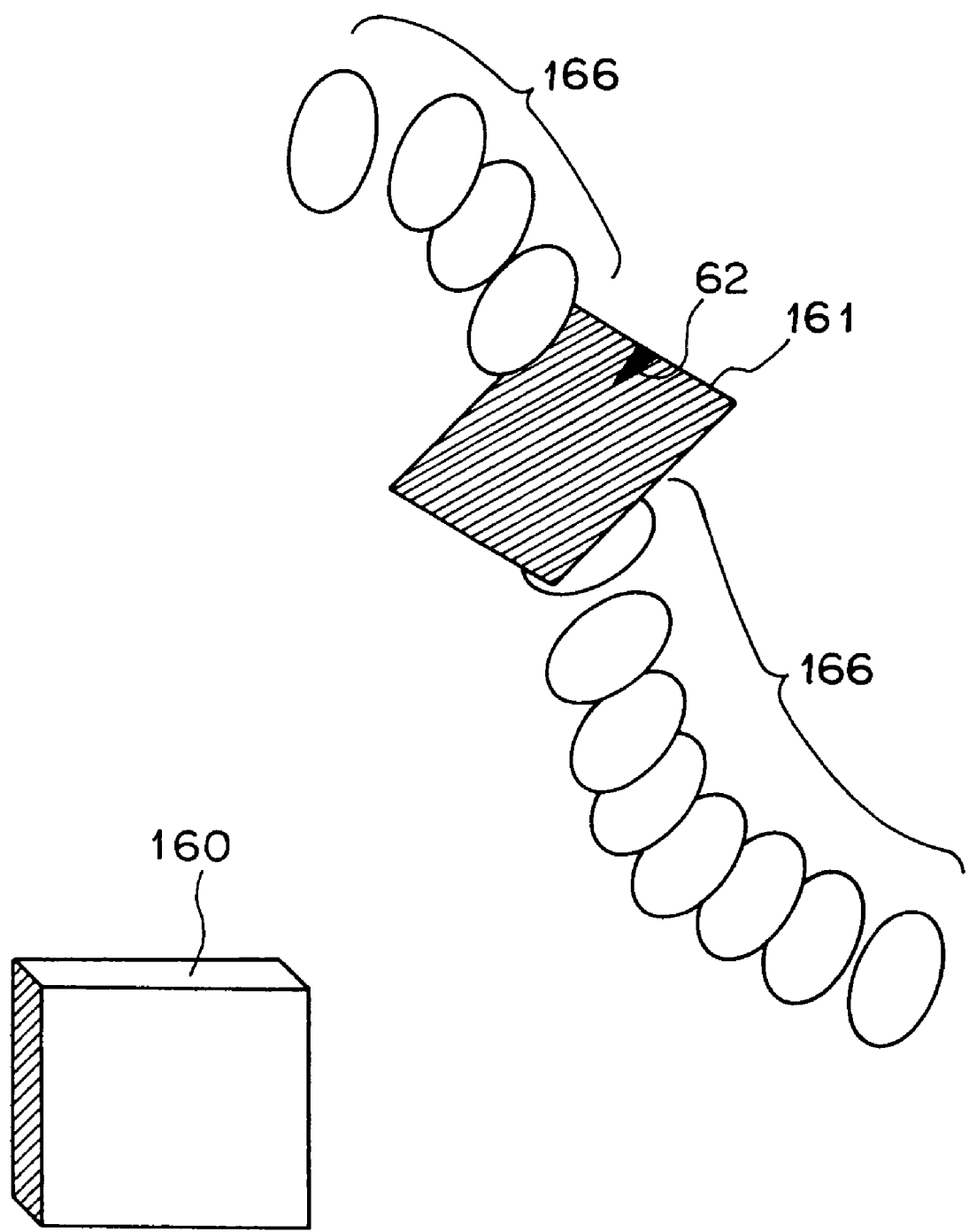
FIG. 32 is an explanatory diagram showing the variation example of a guide image in the ultrasonic diagnostic apparatus according to the fourth embodiment.

FIGS. 20 to 32 relate to the fourth embodiment. FIG. 20 is a schematic configuration diagram of the ultrasonic diagnostic apparatus. FIG. 21 is an enlarged sectional view of a distal end to be inserted of an insert portion of an endoscope. FIG. 22 is an external view in which the ultrasonic diagnostic apparatus works on a body to be examined. FIG. 23 is a conceptual diagram of data for describing position and direction data. FIG. 24 is an explanatory diagram showing an ultrasonic guide image. FIGS. 25 to 30 are explanatory diagrams showing display examples displaying an ultrasonic image and an ultrasonic guide image together on a monitor. FIGS. 31 and 32 are explanatory diagrams showing variation examples of a guide image.

In FIG. 20, an ultrasonic diagnostic apparatus 101 according to the fourth embodiment includes an ultrasonic endoscope 102, an optical image processing portion 103, a magnetic sensor unit 104, a position and direction detecting portion 105, an ultrasonic image processing portion 106, and a monitor 107 as a display unit. In the fourth embodiment, among signal lines shown in FIG. 20, a thin dashed line, a thick line (solid line), and a long dashed line, a chain double-dashed line and a thin line (solid line) indicate flows of signals/data relating to an optical image, signals/data relating to an ultrasonic image (tomographic image), signals/data relating to a position/direction of an ultrasonic image, signals/data relating to a display screen and the other signals/data, respectively.

The ultrasonic endoscope 102 has an endoscope insert portion 110 and an endoscope operating portion 111. The endoscope insert portion 110 has flexibility and is inserted to a body cavity of a body to be examined 100. The endoscope operating portion 111 is provided and connected to the proximal end of the endoscope insert portion 110.

As shown in FIG. 21, a hard frame 112 is connected to the distal end of the endoscope insert portion 110. A distal-end cap 115 is provided to cap the distal end of the hard frame 112. The distal-end cap 115 is made of a material such as hard polyethylene and polymethylpenten, allowing ultrasonic wave to pass through efficiently. An ultrasonic transducer 116 is provided within the distal-end cap 115. The ultrasonic transducer 116 is freely pivotably supported by the hard frame 112. An ultrasonic transmission medium 117 such as fluid paraffin and deaerated water is filled within the distal-end cap 115.

The distal end of a flexible shaft 118 is connected to the ultrasonic transducer 116. The flexible shaft 118 is made of a flexible material. The proximal-end side of the flexible shaft 118 is guided (not shown) to the endoscope operating portion 111 side through the endoscope insert portion 110 and is connected to a motor 133 provided within the endoscope operating portion 111. Thus, the ultrasonic transducer 116 is rotated and driven through the flexible shaft 118 in the direction indicated by the arrow in FIG. 21 (that is, in the clockwise direction). A signal line (not shown) is wired within the flexible shaft 118. The ultrasonic transducer 116 outputs echo signals to an ultrasonic signal processing circuit 140 (which will be described later) within the ultrasonic image processing portion 106 through the signal line and the endoscope operating portion 111.

A pair of magnetic sources 121 and 122 are provided within the hard frame 112 at the distal end of the endoscope insert portion 110. The pair of magnetic sources 121 and 122 includes solenoid coils generating a magnetic field in a space. The pair is connected to a coil driver circuit 137 (which will be described later) within a position and direction detecting portion 105 through the signal lines 123 and 124 and the endoscope operating portion 111. A direction of a winding axis including the coil of the one magnetic source 121 between the magnetic sources is set in the "direction of 12 o'clock" shown in FIG. 21. A direction of a winding axis including the coil of the other magnetic source 122 is set in the "direction of the normal" shown in FIG. 21. Here, according to the fourth embodiment, the direction of the normal is a direction of an insert axis of the endoscope insert portion 110. The direction of the normal agrees with the direction of the normal of an ultrasonic image resulting from radial scanning of the inside of a body cavity of the body to be examined 100 by the ultrasonic transducer 116. The direction of 12 o'clock is a direction of one axis orthogonal to the direction of the normal. The direction of the winding axis of the magnetic source 22 is set so as to agree with the direction of 12 o'clock of an ultrasonic image (see FIG. 25). The radial scanning by the ultrasonic transducer 116 will be described later.

Furthermore, a CCD camera 125 for picking up an optical image is provided in the hard frame 112 at the distal end of the endoscope insert portion 110. An image-pickup light irradiating window 126 is provided closely in a CCD camera 125. The image-pickup light irradiating window 126 irradiates to a body cavity the light required for picking up an image in the CCD camera 125. The CCD camera 125 is connected to the optical image processing portion 103 via a signal line (not shown) wired in the endoscope insert portion 110 and the endoscope operating portion 111. When image pickup signals are output from the CCD camera 125 to the optical image processing portion 103, the optical image processing portion 103 creates an optical image of an internal part of a body cavity based on the image pickup signals. A distal end part of a light-guide path (not shown) such as optical fiber is provided at the image-pickup light irradiating window 126. The proximal end of the light-guide path is connected to a light source apparatus (not shown) via the inside of the endoscope insert portion 110 and endoscope operating portion 111. Thus, image pickup light is guided to the image-pickup light irradiating window 126.

As shown in FIG. 20, the endoscope operating portion 111 has a motor 133 and a rotary encoder 134. The motor 133 rotates and drives the ultrasonic transducer 116 through the flexible shaft 118. The rotary encoder 134 detects a rotational angle of the motor 133. The rotary encoder 134 is connected to the rotational axis of the motor 133 through a rigid shaft. Thus, a rotating angle is detected from a reference position with respect to the direction of 12 o'clock of the ultrasonic transducer 116, and detected rotating angle is output as a rotating angle signal to the ultrasonic signal processing circuit 140 within the ultrasonic image processing portion 106.

The magnetic sensor unit 104 has plural magnetic sensors 135, which are solenoid coils for sensing magnetic fields. These magnetic sensors 135 are provided at predetermined positions and in a predetermined direction within a cabinet of the magnetic sensor unit 104. Thus, the magnetic sensors 135 can sense magnetic fields from the magnetic sources 121 and 122 provided at the distal end of the endoscope insert portion 110.

The position and direction detecting portion 105 functions as position information detecting means together with the magnetic sensor unit 104 and the magnetic sources 121 and 122. The position and direction detecting portion 105 has a coil driver circuit 137, a position and direction calculating circuit 138. The coil driver circuit 137 generates and outputs drive signals to the magnetic sources 121 and 122. The position and direction calculating circuit 138 calculates position vectors and direction vectors expressing directions of the winding axes of the magnetic sources 121 and 122, respectively, based on signals received from the magnetic sensors 135 provided in the magnetic sensor unit 104. The position vectors and direction vectors calculated by the position and direction calculating circuit 138 are output as position and direction data (position information) to a guide image creating circuit 141 and image mixing circuit 142 of the ultrasonic image processing portion 106.

The ultrasonic image processing portion 106 has an ultrasonic signal processing circuit 140, the guide image creating circuit 141, the image mixing circuit 142, a display circuit 143, a hard disk (called HDD hereinafter) 144, and a control circuit 145. The ultrasonic signal processing circuit 140 creates an ultrasonic image by performing publicly known signal processing such as envelope detection, logarithm multiplication, A/D conversion, and digital scan conversion (which will be described later) on echo signals from the ultrasonic transducer. The guide image creating circuit 141 is auxiliary image creating means for creating an ultrasonic guide image (simply called guide image, hereinafter) as an auxiliary image illustrating a relationship between a locus of the distal end of the endoscope insert portion 110 and a position and direction of a given ultrasonic image based on the position and direction data from the position and direction calculating circuit 138. The image mixing circuit 142 is display control means for creating display image data for displaying an ultrasonic image, a guide image and an optical image from the optical image processing portion 103 in a predetermined manner simultaneously or by selectively combining (mixing) these images such that these images can be compared. The display circuit 143 converts image data generated by the image mixing circuit 142 to analog video signals. The HDD 144 stores different kinds of image data such as a display image, an ultrasonic image, a guide image and an optical image created by the image mixing circuit 142 in connection with the position and direction data. The control circuit 145 totally controls the components within the ultrasonic image processing portion 106 including the guide image creating circuit 141 based on an input signal from input means such as the mouse 146, the keyboard 147 and a trackball 148 provided on the keyboard 147.

Here, as shown in FIG. 22, according to the fourth embodiment, the monitor 107, the ultrasonic image processing portion 106, the optical image processing portion 103 and the position and direction detecting portion 105 are provided as units having separate cabinets. They are held integrally by a trolley 150. The magnetic sensor unit 104 provided in a rectangular parallelepiped cabinet is fixed on a bed 151 on which the body to be examined 100 is placed on his/her back or side. In this case, the magnetic sensor unit 104 is fixed so as to be close to an area of concern of the body to be examined 100 as much as possible. Thus, a distance between the distal end of the endoscope insert portion 110 including the magnetic sources 121 and 122 and the magnetic sensor 104 is defined smaller. Therefore, an S/N ratio can be increased, and a magnetic field can be sensed by the magnetic sensor unit 104 with high accuracy. An operator performs examination by inserting and/or withdrawing the distal end of the endoscope insert portion 110 in a direction indicated by the arrow shown in FIG. 22 by hand and rotating (twisting) the distal end of the endoscope insert portion 110 about the insert direction.

Next, an operation of the fourth embodiment having the above-described construction will be described.

First of all, a flow of signals/data relating to an optical image will be described.

An image pickup signal captured by the CCD camera 125 mounted at the distal end of the endoscope insert portion 110 undergoes signal processing and image processing required by the optical image processing portion 103 and is output to the image mixing circuit 142 within the ultrasonic image processing portion 106 as an optical image.

Next, a flow of signals/data relating to an ultrasonic image will be described.

The ultrasonic transducer 116 receives an exciting signal in a pulse-voltage shape emitted by the ultrasonic signal processing circuit 140 within the ultrasonic image processing portion 106 and converts the exciting signal to an ultrasonic beam, which is a compressional wave of a medium. The ultrasonic beam propagates through an ultrasonic transmission medium 117 and the distal-end cap 115 and is irradiated to the outside of the ultrasonic endoscope 102. Then, reflected echo from the inside of the body to be examined 100 returns to the ultrasonic transducer 116 through an opposite path of the ultrasonic beam. The ultrasonic transducer 116 converts the reflected echo to electric echo signals and transmits the echo signals to the ultrasonic signal processing circuit 40 through a path reverse to that of the exciting signals. Furthermore, while this operation is repeated, the motor 133 within the endoscope operating portion 111 is rotated. Thus, the flexible shaft 118 and the ultrasonic transducer 116 rotate in the direction indicated by the block arrow in FIG. 21. Therefore, ultrasonic beams are sequentially irradiated in all directions within a plane vertical to the endoscope insert portion 110 (called radial scan plane, hereafter), and so-called mechanical radial scanning (simply called radial scanning, hereafter) is performed. The ultrasonic signal processing circuit 140 performs publicly known processing, such as envelope detection, logarithm multiplication, A/D conversion, and digital scan conversion (processing converting data in a polar coordinates system generated by radial scanning to image data in an orthogonal coordinates system), on echo signals from the ultrasonic transducer 116 and creates image data of an ultrasonic image. In order to create the image, the direction of 12 o'clock of an ultrasonic image is determined by using a rotational angle signal from the rotary encoder 134. The ultrasonic image is output to the image mixing circuit 142.

Next, a flow of signals and data relating to a position and direction of an ultrasonic image will be described. The magnetic sources 121 and 122 are driven by drive signals generated by the coil driver circuit 137 of the position and direction detecting portion 105. When the magnetic sensors 135 of the magnetic sensor unit 104 receive magnetic fields from the magnetic sources 121 and 122, the signals received from the magnetic sensors 135 are converted to the position and direction data of the distal end of the endoscope insert portion 110 and are output to the guide image creating circuit 141 within the ultrasonic image processing portion 106.

Here, as shown in the conceptual diagram in FIG. 23, the position and direction data calculated by the position and direction calculating circuit 138 includes:

(1) Position vector, r[=(x, y, z)] of the center of the rotation of the ultrasonic transducer 116, wherein the center of the rotation of the ultrasonic transducer 116 and the magnetic sources 121 and 122 are at the distal end of the endoscope insert portion 110 and are close to each other. The positional relationship therebetween is fixed by the hard frame 112. Thus, r may be equal to the position vector based on one of the two magnetic sources 121 and 122;

(2) Direction vector, Vh[=(Vhx, Vhy, Vhz) of an ultrasonic image in the direction of the normal, wherein the direction vector Vh is equal to the direction vector of the magnetic source 122 wound in the direction of the normal;

(3) Direction vector V12[=(V12x, V12y, V12z)] of an ultrasonic image in the direction of 12 o'clock, wherein the direction vector V12 is equal to the direction vector of the magnetic source 121 wound in the direction of 12 o'clock.

Here, the components of the vector are given with in [ ], and these components are defined as components for a coordinates system determined with reference to the rectangular parallelepiped magnetic sensor unit 104. In reality, these components are output as position and direction data.

As being apparent from FIG. 23, an ultrasonic image is within a plane (radial scan plane) created by two vectors including the vector Vh and the vector (V12×Vh) (where × is an exterior product).

The guide image creating circuit 141 creates a guide image, which will be described later, from position and direction data obtained in the position and direction calculating circuit 138 and outputs the guide image to the image mixing circuit 142.

Finally, a flow of signals/data relating to a display screen on the monitor 107 will be described.

The image mixing circuit 142 creates image data for displaying an optical image, an ultrasonic image and a guide image separately and/or image data for displaying them on a same screen such that they can be compared with each other. The image data is converted to analog video signals by the display circuit 143, and the analog video signals are output to the monitor 107. Furthermore, the image mixing circuit 142 outputs the optical image, the ultrasonic image, the guide image and the position and direction data to the HDD 144 in synchronization and in connection with each other such that they can be provided and used after the examination.

An operation of a method of creating an ultrasonic guide image by the guide image creating circuit 141 will be described below in detail.

First of all, the guide image creating circuit 141 captures position and direction data from the position and direction calculating circuit 138 every time when the ultrasonic signal processing circuit 140 creates an ultrasonic image. The ultrasonic signal processing circuit 140 creates an ultrasonic image every time when the ultrasonic transducer 116 performs radial scanning. Thus, sets of plural pieces of position and direction data in connection with respective ultrasonic images are sequentially captured by the guide image creating circuit 141.

Next, the guide image creating circuit 141 creates an ultrasonic guide image as shown in FIG. 24, for example. The guide image includes a magnetic sensor unit marker 160, plural ultrasonic image markers 161 displayed with respect to the magnetic sensor unit marker 160, a direction-of-12-o'clock marker 162 displayed on the ultrasonic image marker 161, and a locus marker 163.

The magnetic sensor unit marker 160 is a parallelepiped marker expressed in a guide image in the same form as that of the magnetic sensor unit 104 in order to express a direction of the magnetic sensor unit 104. In this case, surfaces of the magnetic sensor unit 104 have predetermined colors, and the corresponding surfaces of the magnetic sensor unit marker 160 have the same colors. Thus, an operator or the like can easily recognize a correspondence between the direction of the actual magnetic sensor unit 104 and the magnetic sensor unit marker 160. In the example shown in FIG. 24, the front side, upper side and right side of the magnetic sensor unit 160 are defined yellow, blue and red, respectively.

The ultrasonic image marker 161 (ultrasonic markers 161a to 161e. in the shown example) is a plate-shape marker resulting from projection onto a plane of a rectangle (or square) expressing a position and direction of a radial scan plane of an ultrasonic image obtained in each timing, that is, a position and direction of each ultrasonic image. The ultrasonic image marker 161 can be easily created from the three component vectors r, Vh and V12. Plural radial scan planes are shown in FIG. 23 while, for convenience of description, images are thinned out in FIG. 24.

The direction-of-12-o'clock marker 162 (162a to 162e in the shown example) is a triangle marker expressing the direction of 12 o'clock of an ultrasonic image on the ultrasonic image marker 161. The direction-of-12-o'clock marker 162 can be easily created from three component vectors r, Vh and V12. The direction-of-12-o'clock marker 162 is a triangle having an apex in the direction toward the center of an image from the direction of 12'oclock.

The locus marker 163 is a curved marker expressing a locus that the distal end of the endoscope insert portion 110 follows. The locus marker 163 is created by sequentially connecting chronological points indicating the vector r. In other words, since a history of a movement of the rotational center of radial scanning can be obtained by chronologically following the point indicating the vector r, a locus marker can be obtained by sequentially and chronologically connecting points indicating r and then projecting the locus onto a plane. Interpolation is required when they are connected. They may be interpolated into a straight line or into a curved line by using the plural position vectors.

In accordance with the insertion or the withdrawal after insertion to a deeper part of the body to be examined 100 by an operator by causing the ultrasonic transducer 116 to perform radial scanning, the guide image creating circuit 141 displays new ultrasonic image markers 161 and direction-of-12-o'clock markers 162 as sequentially referred by the reference numerals 161e, 161d, 161c, 161b and 161a and 162e, 162e, 162c, 162b and 162a in FIG. 24. At the same time, the guide image creating circuit 141 extends the locus marker 163. The guide image creating circuit 141 synthesizes the ultrasonic image markers 161, the direction-of-12-o'clock markers 162 and the locus marker 163 and creates a guide image as well as the magnetic sensor unit marker 160.

Specific display examples and a display method thereof will be described for displaying an ultrasonic guide image and ultrasonic image during radial scanning on the monitor 107 at the same time.

[First Display Example]

Figure 25:
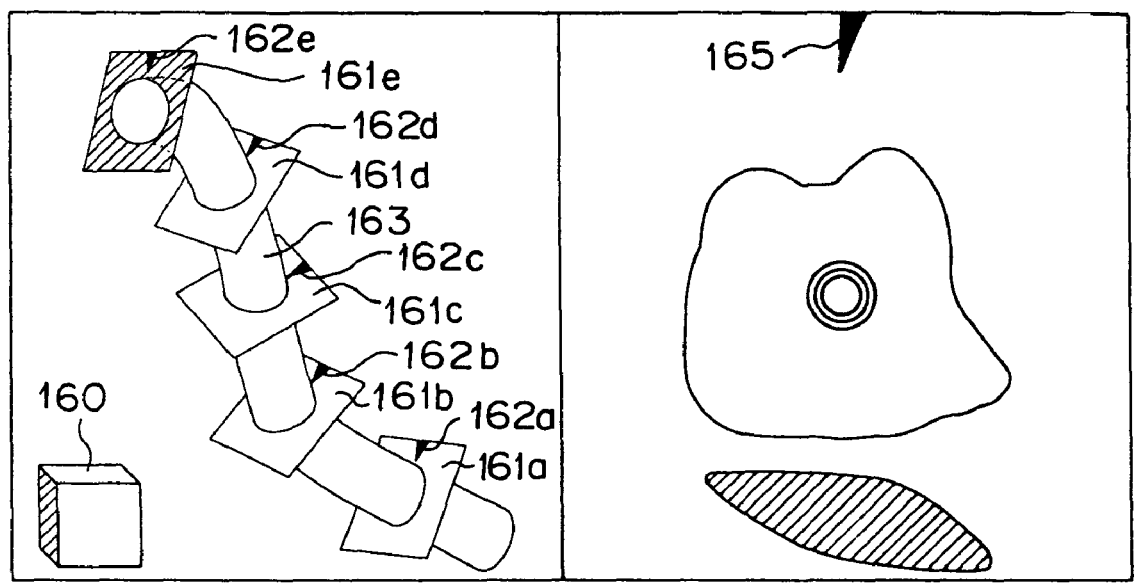
FIG. 25 is an explanatory diagram showing display examples displaying an ultrasonic image and an ultrasonic guide image together on a monitor in the ultrasonic diagnostic apparatus according to the fourth embodiment.

FIG. 25 shows a display example of an ultrasonic image and ultrasonic guide image during radial scanning by the ultrasonic transducer 116. As shown in the display example, a newest ultrasonic image is displayed on the right side of the monitor 107 and a guide image is displayed on the left side of the monitor 107. The guide image creating circuit 141 displays the ultrasonic image marker 161 (ultrasonic image marker 161e in the shown example) indicating an ultrasonic image being displayed in a different color from that of another ultrasonic image markers 161. In this way, by painting the newest ultrasonic image marker 161 in a different color, the newest ultrasonic image being currently displayed can be mapped to the newest ultrasonic image marker 161. The direction-of-12-o'clock marker 165 corresponding to the direction-of-12-o'clock marker 162 (direction-of-12-o'clock marker 162e) provided on the newest ultrasonic image marker 161 is provided on an ultrasonic image. The form of the direction-of-12-o'clock marker 165 is a similar figure to the direction-of-12-o'clock marker 162 on a guide image thereof. By the way, when an operator performs radial scanning and, at the same time, inserts and/or withdraws the distal end of the endoscope insert portion 110, the newest ultrasonic image marker 161, direction-of-12-o'clock marker 162 and locus marker 163 may lie off the monitor screen. However, the image mixing circuit 142 prompts automatic scrolling of these markers so as to prevent the ultrasonic image marker 161 of the ultrasonic image being displayed from lying off the screen.

According to this display example, by having the image mixing circuit 42 and the like and operated such that the newest ultrasonic tomographic image and the guide image can be displayed on the right and left sides, respectively, on the monitor 107, which part of an ultrasonic image displayed on the current monitor 107 is being scanned can be easily recognized by an operator, for example. In other words, when the endoscope insert portion 10 is inserted and/or withdrawn along the digestive tract through the esophagus, the stomach and the duodenum, for example, the locus substantially and anatomically agrees with the form of the duodenum. By using the fact, an operator can clearly identify which part within a body cavity the distal end of the insert portion 10 of the ultrasonic endoscope exists based on the guide image.

The direction-of-12-o'clock markers 162 and 165 indicating the direction of 12 o'clock of the ultrasonic image marker 161 and an ultrasonic image are provided on the ultrasonic image marker 161 and an ultrasonic image such that they can be compared. Therefore, which part is scanned especially in which direction for an ultrasonic image being displayed on the current monitor can be clearly recognized by an operator, for example.

The ultrasonic image marker 161 indicating the ultrasonic image being currently displayed has a different color from that of the other ultrasonic image markers 161. Therefore, which part is being scanned to obtain the ultrasonic image being currently displayed on the screen can be more clearly recognized.

Since a history of ultrasonic images obtained until then can be recognized at a glance by using the ultrasonic image markers 161 of a guide image, an operator can easily recognize which part of the body to be examined 100 and how many (density) ultrasonic images are picked up. Therefore, unexpected failure in picking up an image may hardly occur.

[Second Display Example]

Figure 26:
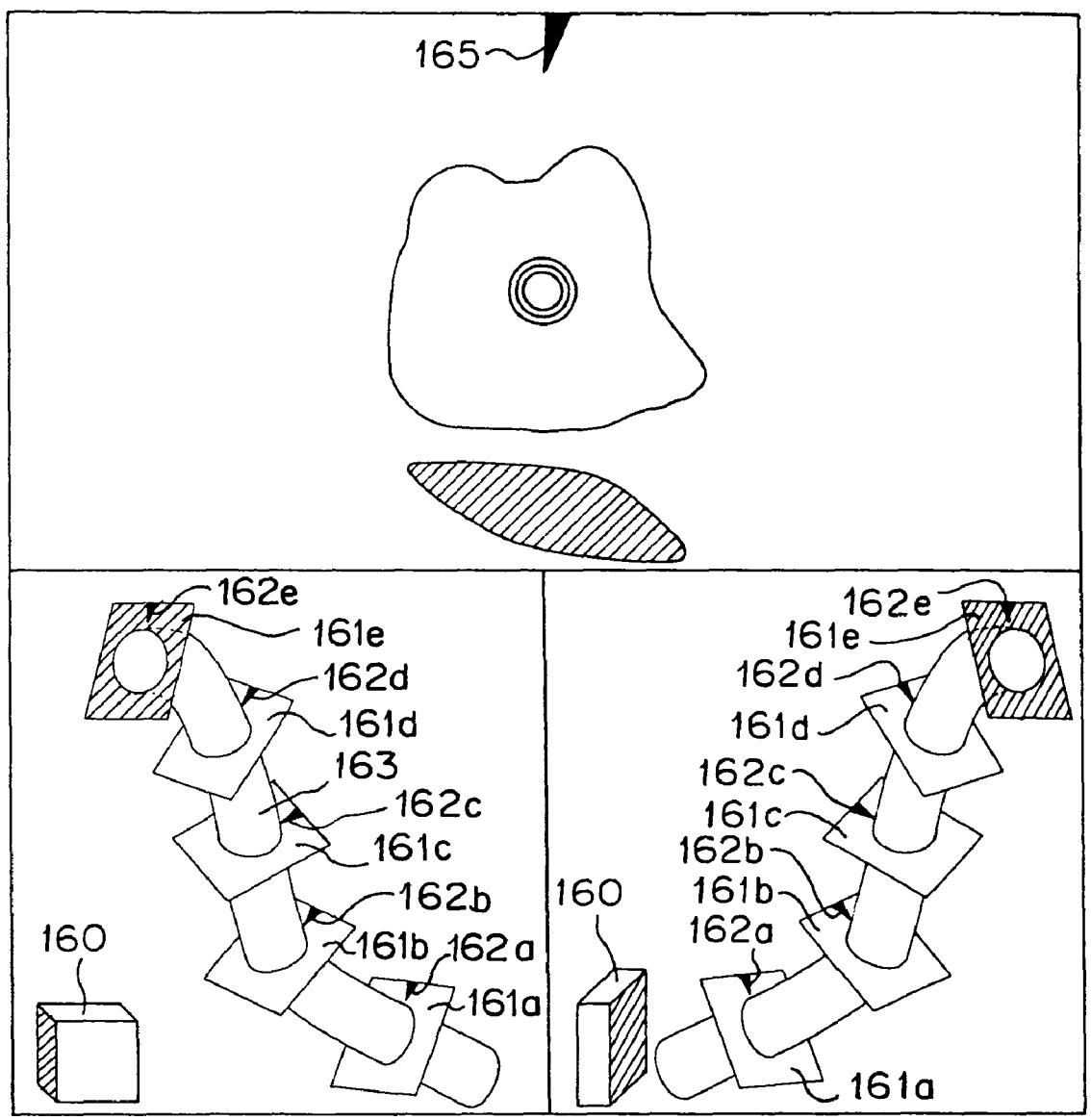
FIG. 26 is an explanatory diagram showing display examples displaying an ultrasonic image and an ultrasonic guide image together on a monitor in the ultrasonic diagnostic apparatus according to the fourth embodiment.

FIG. 26 shows a display example of an ultrasonic image and ultrasonic guide image during radial scanning by the ultrasonic transducer 116. In this display example, as shown in FIG. 26, a newest ultrasonic image is displayed at the upper side of the monitor 107, and guide images from different directions are displayed on the lower left and right respectively. The guide image on the lower right side is a guide image viewed in a different direction orthogonal to that of the guide image on the lower left side. With this operation, even when the screen of monitor 107 is two-dimensional, easily-understandable expression can be obtained during an examination.

In the construction and operation according to this display example, the guide image creating circuit and the image mixing circuit display a newest ultrasonic image on the upper side of the monitor 107, for example, and also display guide images having different directions on the lower left and right sides. Thus, which part is being scanned to obtain an ultrasonic image being currently displayed on the screen can be more easily recognized by an operator, for example.

[Third Display Example]

Figure 27:
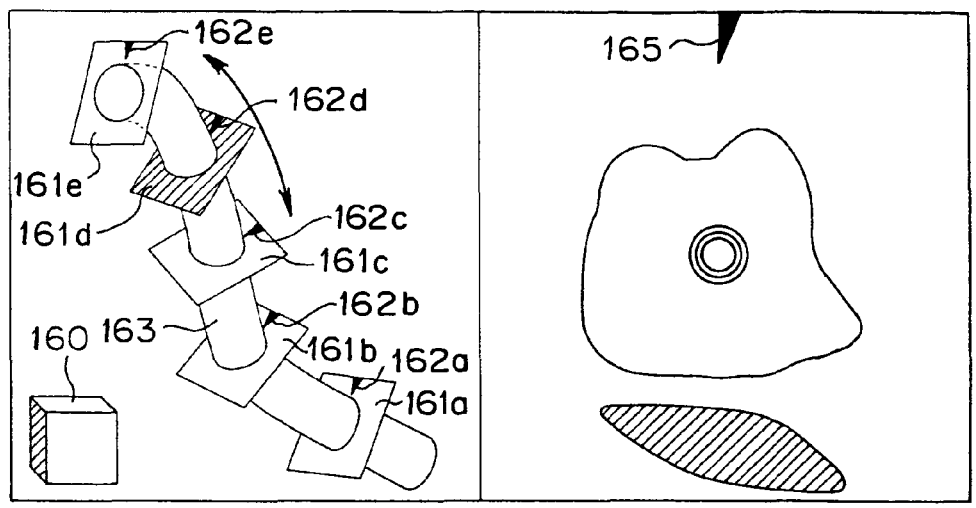
FIG. 27 is an explanatory diagram showing display examples displaying an ultrasonic image and an ultrasonic guide image together on a monitor in the ultrasonic diagnostic apparatus according to the fourth embodiment.

FIG. 27 shows a display example of an ultrasonic image and ultrasonic guide image after radial scanning in the ultrasonic transducer 116. In this display example, as shown in FIG. 27, an ultrasonic image read from the HDD 144 is displayed on the right side of the monitor 107 while a guide image corresponding to the ultrasonic image is displayed on the right side of the monitor 107. In this case, an operator can select an ultrasonic image recorded during radial scanning through the mouse 146 and/or the keyboard 147 and reads the selected one onto the monitor 107.

This display example can be achieved by performing a following operation.

First of all, a predetermined ultrasonic image is selected by an operator from ultrasonic images recorded in the HDD 144, the image mixing circuit 142 chronologically or in the opposite order reads the selected ultrasonic image and position and direction data of a series of ultrasonic images including the ultrasonic image recorded during scanning. Then, the image mixing circuit 142 outputs the read position and direction data to the guide image creating circuit 141. The guide image creating circuit 141 creates a guide image based on the position and direction data and outputs the guide image to the image mixing circuit 142 again. Thus, the guide image is displayed together with the ultrasonic image on the same screen as shown in FIG. 27.

Next, an operation for changing a guide image in accordance with a manipulation by an operation will be described.

When an operator manipulates an arrow key (not shown) on the keyboard 147, the mouse 146 and/or the trackball 148 by watching a screen at the same time, the image mixing circuit 142 read chronologically or in the opposite order ultrasonic images recorded during radial scanning and sequentially updates the ultrasonic images on the right side of the screen. Here, the guide image creating circuit 141 re-creates a guide image such that the ultrasonic image marker 161 (the ultrasonic image marker 161*d* in the shown example) corresponding to the ultrasonic image being displayed on the right side of the screen can have a different color from the color of another ultrasonic image marker 161 for distinction. Then, the guide image creating circuit 141 outputs the re-created guide image to the image mixing circuit 142. Therefore, the operator can recognize that the ultrasonic images on the right side of the screen have been updated sequentially. The operator can further recognize that the ultrasonic image marker having a different color on the left side of the screen is sequentially linked to the position of the adjacent ultrasonic image marker.

According to this display example, an ultrasonic image read from the HDD 144 is displayed on the right side of the screen on the monitor 107, and a guide image linking thereto is displayed on the left side. Thus, an operator can easily recognize at which part the recorded ultrasonic image was recorded in addition to the advantage obtained in the first display example.

The ultrasonic image marker 161 indicating an ultrasonic image being displayed is displayed in a different color from that of the other ultrasonic image marker. Thus, an operator can more easily recognize at which part an ultrasonic image is recorded to obtain the recorded ultrasonic image.

When the ultrasonic image on the right side of the screen is sequentially updated, the ultrasonic image marker 161 having a different color is displayed so as to sequentially move to the position of the adjacent ultrasonic image marker in connection with the update. Thus, an operator can more easily recognize at which part the recorded ultrasonic image an ultrasonic image is recorded. Furthermore, the operator can easily recognize how surrounding organs and vessels are connected along a locus of the movement of the endoscope insert portion 110.

[Fourth Display Example]

Figure 28:
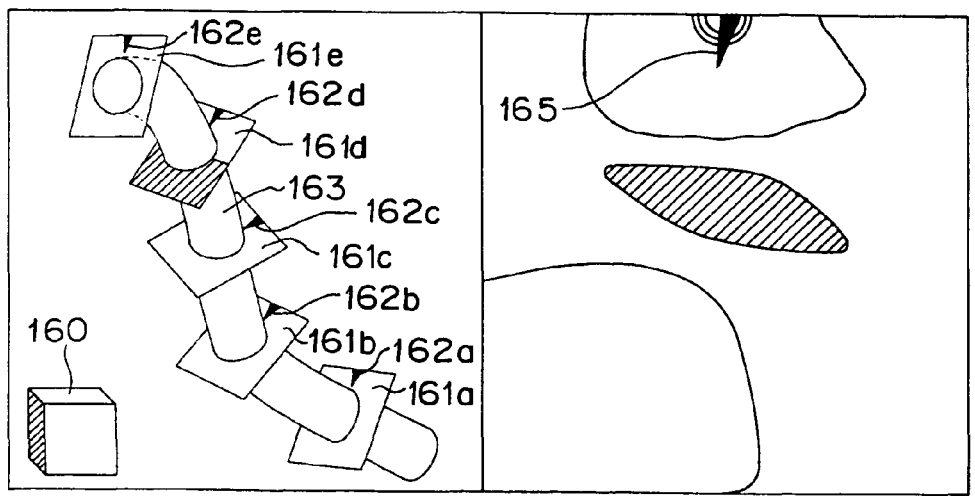
FIG. 28 is an explanatory diagram showing display examples displaying an ultrasonic image and an ultrasonic guide image together on a monitor in the ultrasonic diagnostic apparatus according to the fourth embodiment.

FIG. 28 shows a display example of an ultrasonic image and ultrasonic guide image after radial scanning in the ultrasonic transducer 116. In this display example, an ultrasonic image is displayed on the right side of the monitor 107 while a guide image is displayed on the left side of the monitor 107. Here, an operator selects an ultrasonic image recorded during radial scanning by using the mouse 146 and/or the keyboard 147 and reads the selected one to the screen. Furthermore, the display range of ultrasonic images can be changed. In this case, a lower half circle part or upper half circle part of the ultrasonic image can be displayed such that a part lying off the general display range can be displayed. FIG. 28 shows a case where the lower half circle of a read ultrasonic image is displayed.

The display example can be achieved by an operation below. The operation which will be described below may be performed during radial scanning.

First of all, when an ultrasonic image is selected by an operator from ultrasonic images recorded in the HDD 144, the image mixing circuit 142 chronologically or in the opposite order reads the selected ultrasonic image and position and direction data of a series of ultrasonic images including the ultrasonic image recorded during scanning and outputs the read position and direction data to the guide image creating circuit 141. The guide image creating circuit 141 creates a guide image based on the position and direction data and outputs the guide image to the image mixing circuit 142 again. Thus, the guide image and the ultrasonic image are displayed on the same screen like the third display example.

Next, for example, the operator selects a lower half circle range of an ultrasonic image currently being displayed, the image mixing circuit 142 again reads the ultrasonic image in the range specified by the operator from the HDD 144 and updates the ultrasonic image such that the ultrasonic image in the read range (that is, the lower half circle ultrasonic image) can be enlarged and displayed on the right side of the screen.

Next, an operation for changing a guide image in accordance with a manipulation by an operator will be described.

When the image mixing circuit 142 updates an ultrasonic image on the right side of the screen as described above, the guide image creating circuit 141 creates a guide image such that the color of a part to be displayed (that is, a lower half) of the ultrasonic image marker 161 corresponding to the ultrasonic image (the ultrasonic image marker 161*d* in the shown example) being displayed on the right side of the screen can be different from the color of the other ultrasonic image markers. Then, the guide image creating circuit 141 outputs the guide image to the image mixing circuit 142. Therefore, the operator can recognize that the display range of the ultrasonic image on the right side of the screen has been changed to the lower half circle based on the displayed color of the corresponding ultrasonic image marker 161.

According to this display example, a range of concern can be easily and intensely observed by arbitrarily changing and displaying with magnification the display range of an ultrasonic image in addition to the same advantage as that of the third display example. Here, like this display example, an area on the ultrasonic image marker 161 corresponding to the displayed and enlarged ultrasonic image is displayed in a different color. Thus, an operator can easily recognize which part is displayed under magnification. Furthermore, a positional relationship can be easily understood between the displayed part and a locus that the distal end of the endoscope insert portion 110 follows.

[Fifth Display Example]

Figure 29:
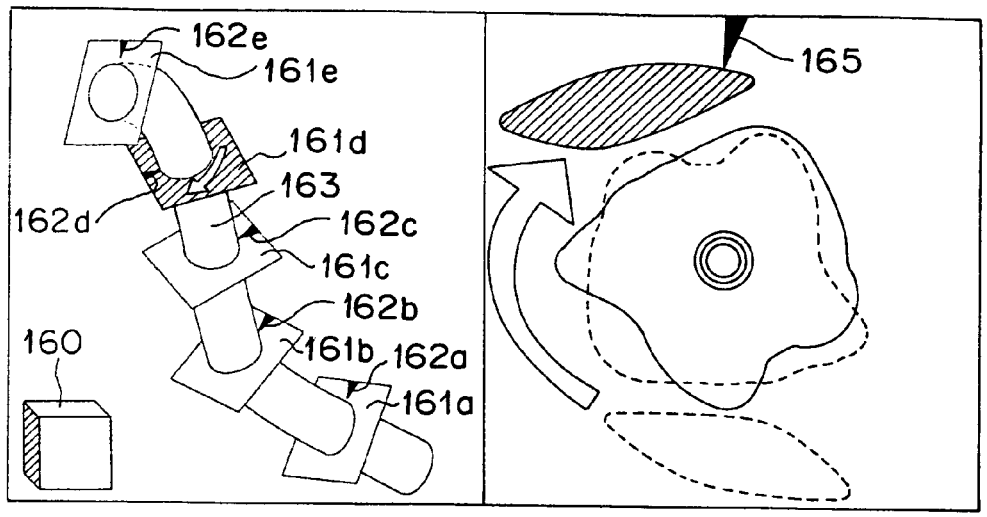
FIG. 29 is an explanatory diagram showing display examples displaying an ultrasonic image and an ultrasonic guide image together on a monitor in the ultrasonic diagnostic apparatus according to the fourth embodiment.

FIG. 29 shows a display example of an ultrasonic image and ultrasonic guide image after radial scanning in the ultrasonic transducer 116. In this display example, as shown in FIG. 29, an ultrasonic image is displayed on the right side of the monitor 107 while a guide image is displayed on the left side of the monitor 107. Here, an operator selects an ultrasonic image recorded during radial scanning by using the mouse 146 and/or the keyboard 147 and reads the selected ultrasonic image to the screen. Furthermore, the operator can rotate the ultrasonic image about the rotational center of the ultrasonic transducer 116 during radial scanning by using the mouse 146, the trackball 148 and/or the keyboard 147. FIG. 29 shows a case where the read ultrasonic image is rotated clockwise (the direction indicated by the arrow in FIG. 29).

This display example can be achieved by an operation below. The operation, which will be described below, may be performed during radial scanning.

First of all, a predetermined ultrasonic image is selected by an operator from ultrasonic images recorded in the HDD 144, the image mixing circuit 142 chronologically or in the opposite order reads the selected ultrasonic image and position and direction data of a series of ultrasonic images including the ultrasonic image recorded during scanning. Then, the image mixing circuit 142 outputs the read position and direction data to the guide image creating circuit 141. The guide image creating circuit 141 creates a guide image based on the position and direction data and outputs the guide image to the image mixing circuit 142 again. Thus, the guide image is displayed together with the ultrasonic image on the same screen like the third display example.

Next, the image mixing circuit 142 rotates the ultrasonic image in accordance with a manipulation by the operator through the mouse 146 and/or the trackball 148.

Next, an operation for changing a guide image in accordance with a manipulation by an operation will be described.

When the image mixing circuit 142 rotates an ultrasonic image on the right side of the screen, the guide image creating circuit 141 rotates the direction of the ultrasonic image marker 161 (ultrasonic image marker 161*d* in the shown example) corresponding to the ultrasonic image being displayed on the right side of the screen including the direction-of-12-o'clock marker 162. Then, the guide image being rotated is sequentially created and is output to the image mixing circuit 142. Therefore the operator can recognize a state of the rotation of the ultrasonic image based on the rotational display of the ultrasonic image marker 161 when the ultrasonic image on the right side of the screen is rotated.

According to this display example, a range of concern can be easily and intensely observed by displaying an ultrasonic image at an arbitrary rotating position in addition to the same advantage as that of the third display example. Here, like this display example, the corresponding ultrasonic image marker 161 in the guide image is rotated in connection with the ultrasonic image. Thus, an operator can easily recognize which part of the rotated ultrasonic image is recorded. Furthermore, a positional relationship can be easily understood between the direction of the rotated ultrasonic image and a locus that the endoscope insert portion 110 follows.

[Sixth Display Example]

Figure 30:
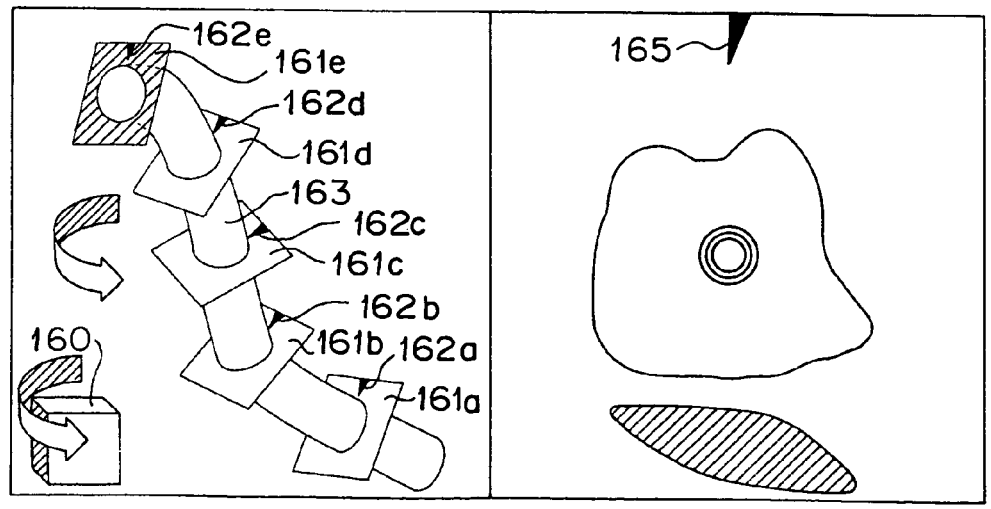
FIG. 30 is an explanatory diagram showing display examples displaying an ultrasonic image and an ultrasonic guide image together on a monitor in the ultrasonic diagnostic apparatus according to the fourth embodiment.

FIG. 30 shows a display example of an ultrasonic image and ultrasonic guide image after radial scanning in the ultrasonic transducer 16. In this display example, as shown in FIG. 30, an ultrasonic image is displayed on the right side of the monitor 107 while a guide image is displayed on the left side of the monitor 107. Here, an operator can rotate the magnetic sensor unit marker 160 of the guide image on the left side of the screen by using the mouse 146, the trackball 148 and/or the keyboard 147. Furthermore, here, the respective ultrasonic image marker 161, direction-of-12-o'clock marker 162 and locus marker 163 can also rotate in connection with the rotation of the magnetic sensor unit marker 160.

This display example can be achieved by an operation below. The operation, which will be described below, may be performed during radial scanning.

First of all, a predetermined ultrasonic image is selected by an operator from ultrasonic images recorded in the HDD 144, the image mixing circuit 142 chronologically or in the opposite order reads the selected ultrasonic image and position and direction data of a series of ultrasonic images including the ultrasonic image recorded during scanning. Then, the image mixing circuit 142 outputs the read position and direction data to the guide image creating circuit 141. The guide image creating circuit 141 creates a guide image based on the position and direction data and outputs the guide image to the image mixing circuit 142 again. Thus, the guide image is displayed together with the ultrasonic image on the same screen like the third display example.

Next, a rotational axis and angle for rotating the magnetic sensor unit marker 160 displayed on the monitor 107 are input by an operator by using the mouse 146, the trackball 148 or the keyboard 147, the guide image creating circuit 141 rotates the magnetic sensor unit marker 160 in accordance with the angle. Furthermore, the guide image creating circuit 141 sequentially creates a guide image in which the respective ultrasonic image marker 161, direction-of-12-o'clock marker 162 and locus marker 163 are rotated in connection therewith. Then, the guide image is output to the image mixing circuit 142. Thus, the magnetic sensor unit marker 160 of the guide image and the guide image in which the respective ultrasonic image marker 161, direction-of-12-o'clock marker 162 and locus marker 163 are rotated are displayed on the left side of the screen on the monitor 107.

According to this display example, in addition to the same advantage as that of the third display example, the recorded ultrasonic image can be observed from different angles with respect to at which part the ultrasonic image is recorded by rotationally displaying the guide image. Therefore, for example, even when the ultrasonic image markers 161 overlap with each other in a display from a given direction, the visibility of desired information can be improved.

[Seventh Display Example]

FIG. 31 shows a display example after radial scanning in the ultrasonic transducer 116. FIG. 31 shows only a guide image. The description of an ultrasonic image is the same as that of the third display example and will be therefore omitted. This display example especially relates to a display example in which the ultrasonic image markers 161 are densely arranged. In other words, when the number of the ultrasonic image markers 161 is large, the locus marker may be hidden. By performing the operation by the guide image creating circuit 141, the locus marker on the guide image is omitted in the display. The display of the guide image may be performed during radial scanning. In this display example, the same advantage can be obtained as that of the third display example.

[Eighth Display Example]

FIG. 32 shows a display example after radial scanning in the ultrasonic transducer 116. FIG. 32 shows only a guide image. The description of an ultrasonic image is the same as that of the third display example and will be therefore omitted. This display example especially relates to a display example in which the ultrasonic image markers 161 are densely arranged. In other words, this display example is a display example in which the ultrasonic image marker 161 corresponding to an ultrasonic image being currently displayed may be hidden by other ultrasonic image markers when the number of the ultrasonic image markers 161 is large. The display example is achieved through the operation by the guide image creating circuit 141. More specifically, as shown in FIG. 32, the guide image creating circuit 141 creates a guide image in which other ultrasonic image markers than the ultrasonic image marker 161 corresponding to the ultrasonic image being displayed are expressed by the oval ultrasonic image marker 166 resulting from the projection of a small circle onto a plane. In this case, each of the small circles constituting the ultrasonic image markers 166 are defined based on a circle having a smaller radius than the vertical and horizontal dimensions of the ultrasonic image marker 161 corresponding to the ultrasonic image being displayed. The guide image display may be performed during radial scanning.

According to this display example, in addition to the same advantage as that of the third display example, the visibility of the ultrasonic image marker 161 corresponding to the ultrasonic image being currently displayed can be advantageously improved.

Figure 33:
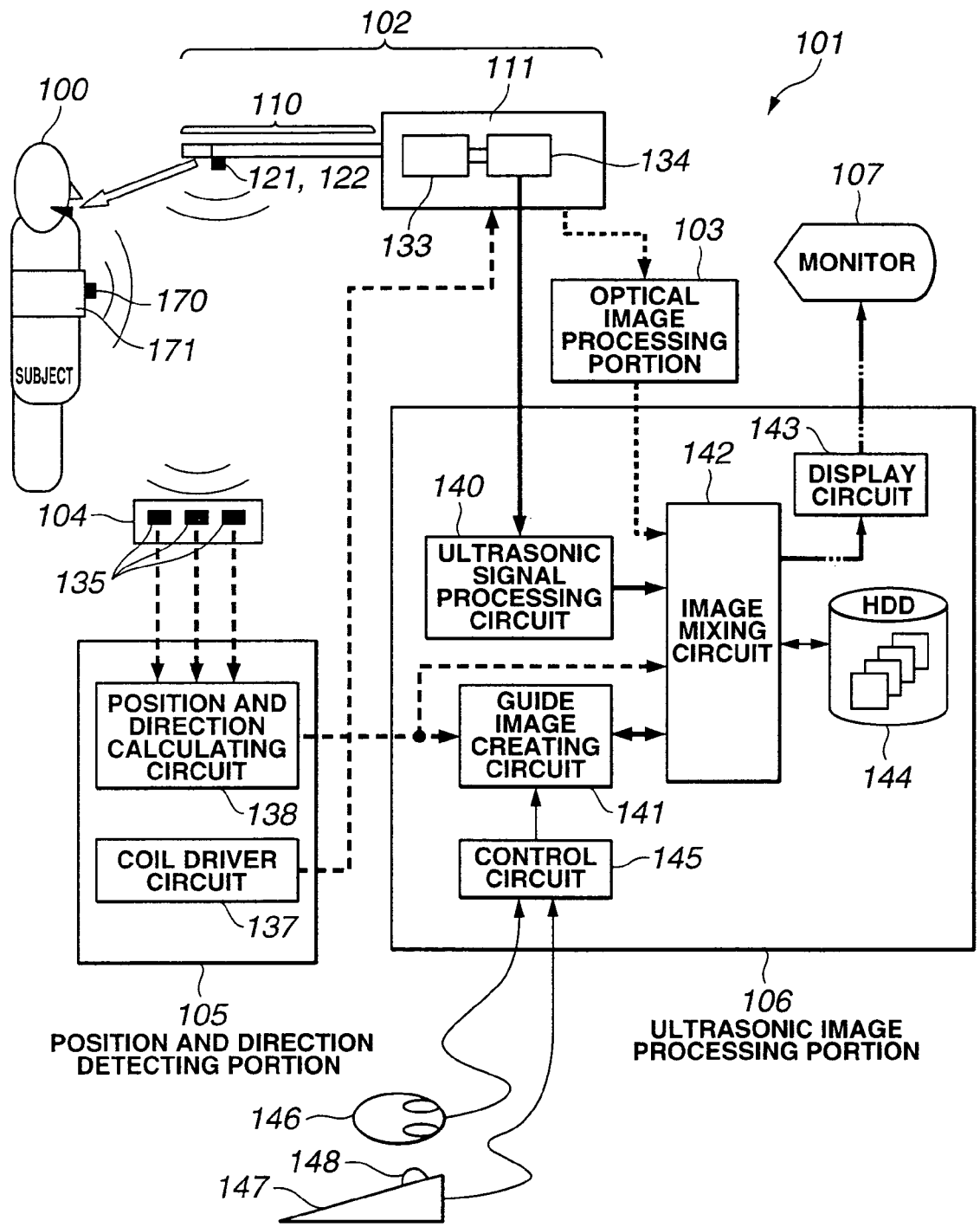
FIG. 33 is a schematic configuration diagram of an ultrasonic diagnostic apparatus according to a fifth embodiment of the invention.
Figure 34:
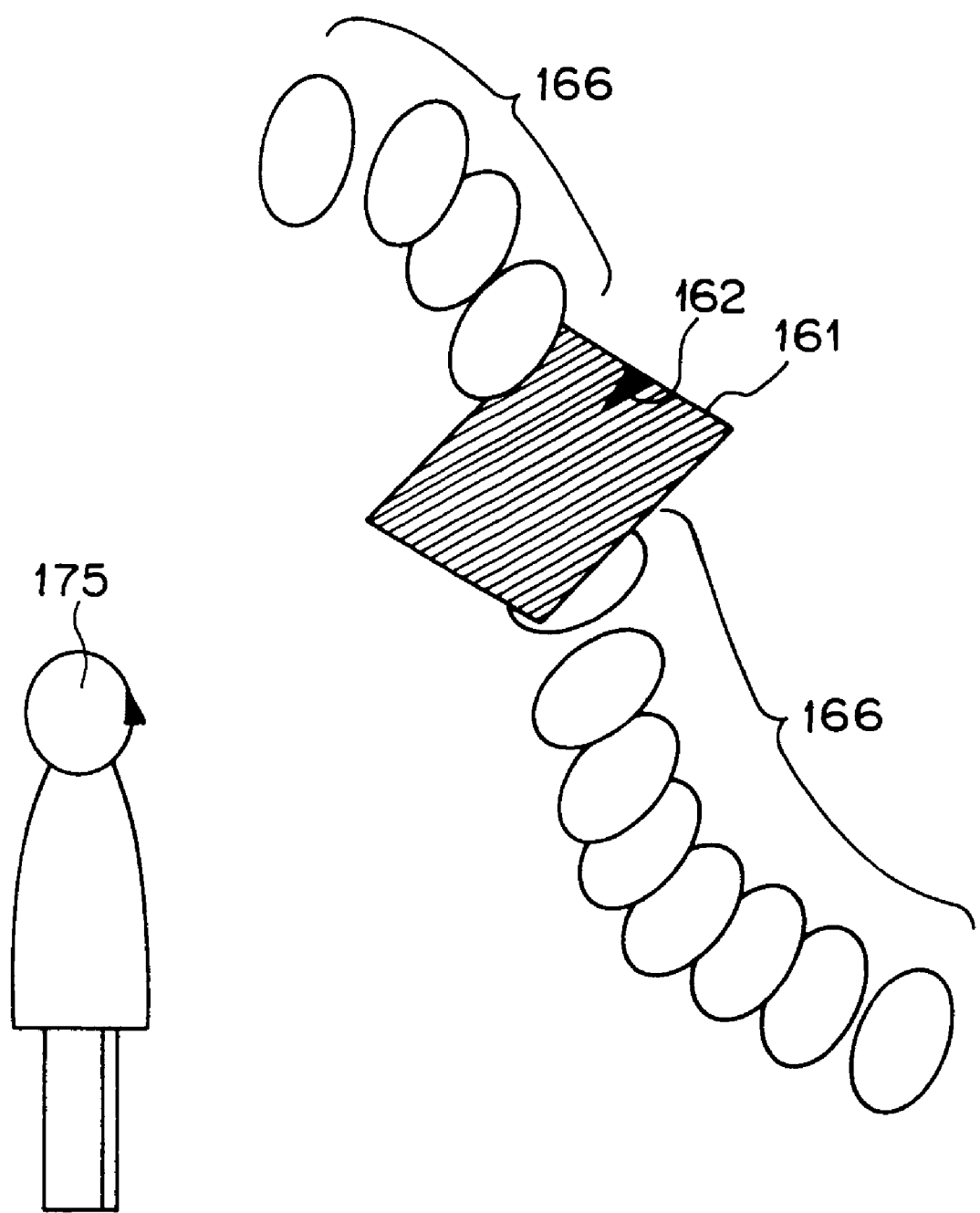
FIG. 34 is an explanatory diagram showing a guide image example according to the fifth embodiment.

Next, FIGS. 33 and 34 relate to the fifth embodiment of the invention. FIG. 33 is a schematic configuration diagram of an ultrasonic diagnostic apparatus. FIG. 34 is an explanatory diagram showing an example of a guide image. According to the fifth embodiment, only differences between the fifth embodiment and the fourth embodiment will be described, and the description of the other similar points will be omitted here.

As shown in FIG. 33, plural sources 170 having solenoid coils wound in different directions are provided on the body to be examined 100 like the magnetic sources 121 and 122 provided in the endoscope insert portion 110. The coil driver circuit 137 inputs drive signals to these magnetic sources 170 through signal lines (not shown). Here, the magnetic sources 170 are fixed on a belt 171 wound around the body to be examined 100. Thus, the position of the magnetic sources 170 can be fixed at a predetermined position on the abdominal part of the body to be examined 100.

Next, an operation under this construction will be described.

According to the fourth embodiment, in order to calculate position and direction data of the magnetic sources 121 and 122 provided at the distal end of the endoscope insert portion 110, the vector components r, $V_h$ and $V_{12}$ are calculated as components for a coordinates system fixed in a parallelepiped magnetic sensor unit. On the other hand, according to the fifth embodiment, the position and direction calculating circuit 138 calculates vectors of the magnetic sources 170 fixed on the body to be examined 100 and then calculates the vector components r, $V_h$ and $V_{12}$ as components of a coordinates system determined by the magnetic sources 170 on the body to be examined 100.

Thus, as shown in FIG. 34, the guide image creating circuit 141 creates an auxiliary image (guide image) with reference to the orientation of the body to be examined 100. Therefore, the auxiliary image according to the fifth embodiment includes a body to be examined marker 175 in a human form expressing the orientation of the body to be examined 100 instead of the magnetic sensor unit marker 160. The other operations are the same as those of the fourth embodiment. FIG. 34 illustrates a display example corresponding to [Eighth Display Example] according to the fourth embodiment. Here, apparently, an auxiliary image may be created in accordance with the other display examples according to the fourth embodiment.

According to the fifth embodiment, in addition to the advantages obtained by the fourth embodiment, the position and direction calculating circuit 138 outputs vector components r, $V_h$ and $V_{12}$ as components for a coordinates system fixed by the magnetic sources 170 on the body to be examined 100. Since the guide creating circuit 141 is adjusted and is operated to create an auxiliary image with reference to an orientation of the body to be examined 100, which part the scanned ultrasonic image being currently displayed on the screen is or which part is recorded of the recorded ultrasonic image can be easily grasped by comparing with the orientation of the body to be examined 100, which is easy to understand. When the body to be examined 100 moves during an examination, this is especially easy to understand and effective.

Figure 35:
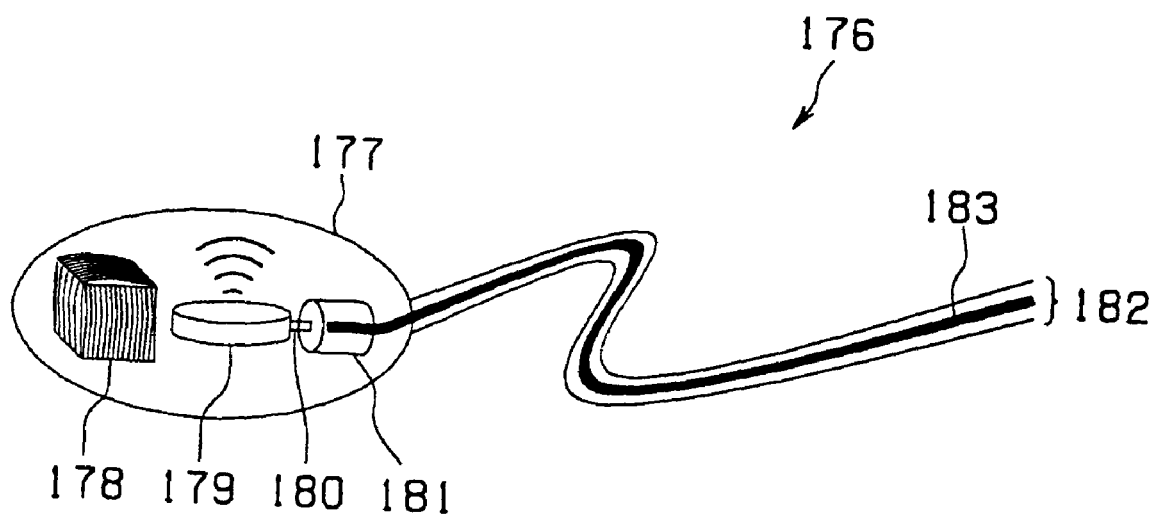
FIG. 35 is a schematic configuration diagram of an ultrasonic probe according to a sixth embodiment of the invention.

Next, FIG. 35 relates to a sixth embodiment of the present invention. FIG. 35 is a schematic configuration diagram of an ultrasonic probe. According to the sixth embodiment, only differences from the fourth embodiment will be described, and the description of the other same points will be omitted here.

Different from the construction according to the fourth embodiment in which the ultrasonic transducer 116 is integrally provided in the endoscope insert portion 110 for achieving a function as a radial scan type ultrasonic probe, an endoscope insert portion is removed according to the sixth embodiment, and instead, an ultrasonic endoscope in a capsule shape (called capsule ultrasonic endoscope, hereinafter) 176 is directly inserted into a body cavity.

The capsule ultrasonic endoscope 176 includes, in a capsule 177, magnetic sources 178, an ultrasonic transducer 179, a rigid shaft 180, and a micromotor 181. The capsule ultrasonic endoscope 176 is directly connected to an endoscope operating portion 111 through a signal cable 182. Under this construction, the micromotor 181 is provided instead of the motor 133 within the endoscope operating portion 111 according to the fourth embodiment.

More specifically, as shown in the figure, in the capsule 177, the ultrasonic transducer 179 is connected to the rigid shaft 180 in a rigid stick shape and is connected to the micromotor 181 through the rigid shaft 180. The ultrasonic transducer 179 is connected to an ultrasonic signal processing circuit 140 within the ultrasonic image processing portion 106 through a signal line 183 via the rigid shaft 180, the micromotor 181 and the signal cable 182 and through the endoscope operating portion 111 via the signal line 183 through the signal cable 182. The magnetic sources 178 are connected to the coil driver circuit 137 within the position and direction detecting portion 105 through the signal line 183. The magnetic source 178 spatially generates a magnetic field based on a drive signal from the coil driver circuit 137. The magnetic sources 178 according to the sixth embodiment are constructed by integrated-solenoid coils wound in two directions. The other construction is the same as that of the fourth embodiment.

According to the sixth embodiment, in addition to the advantages obtained in the fourth embodiment, the capsule ultrasonic endoscope 176 is applied such that the body to be examined 100 can easily swallow the capsule and have the less load, which is an advantage. In this case, since the capsule ultrasonic endoscope 176 can be inserted or be withdrawn by swallowing, falling and writhing, an operator has some difficulty in manipulating the direction of a radial scan plane and which part of the body to be examined 100 is being observed is hard to specify. However, by performing observation using auxiliary images, these problems can be overcome. Thus, an operator, for example, can easily recognize which part the scanned ultrasonic image is.

Figure 36:
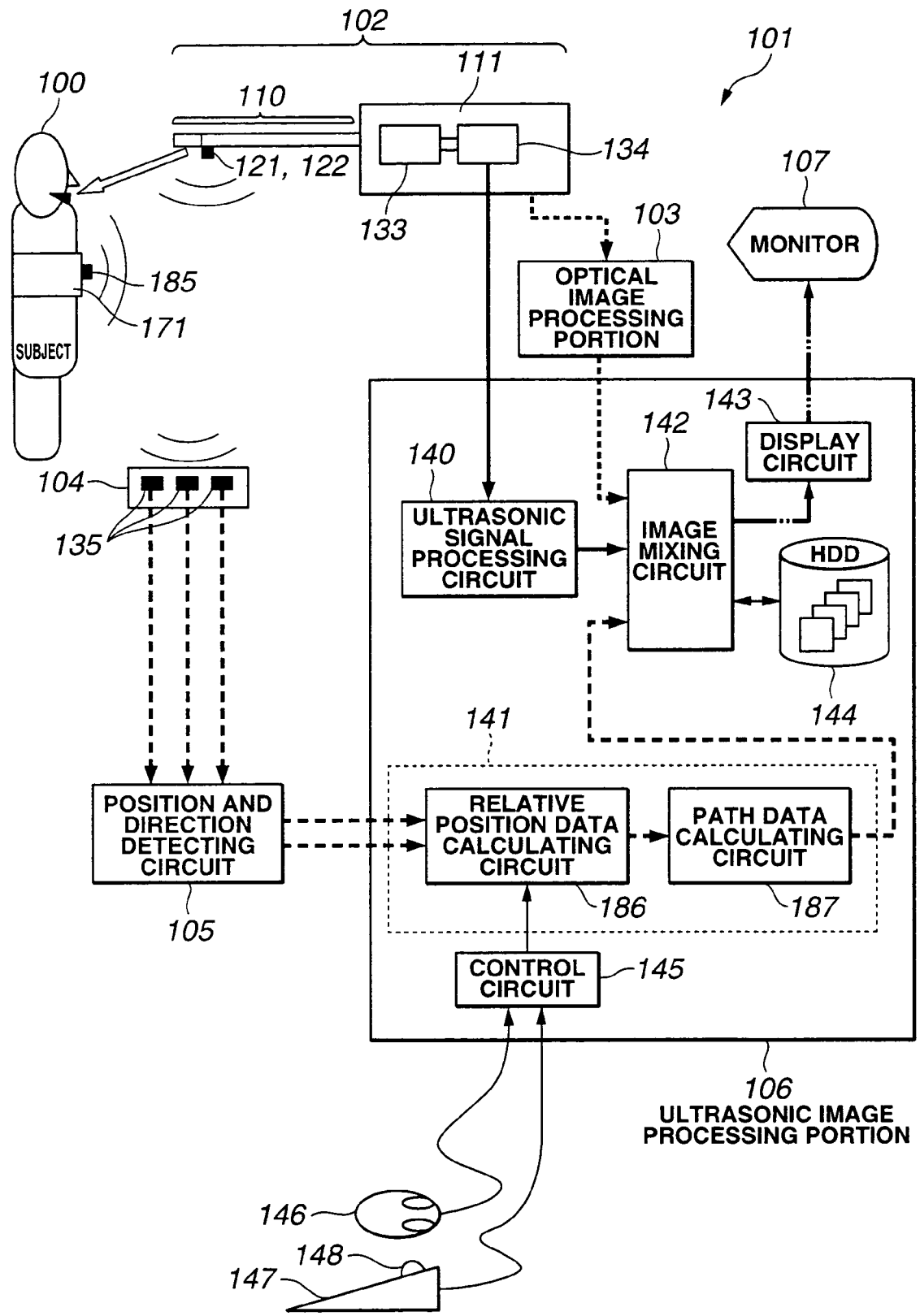
FIG. 36 is a schematic configuration diagram of an ultrasonic diagnostic apparatus according to a seventh embodiment of the invention.
Figure 37:
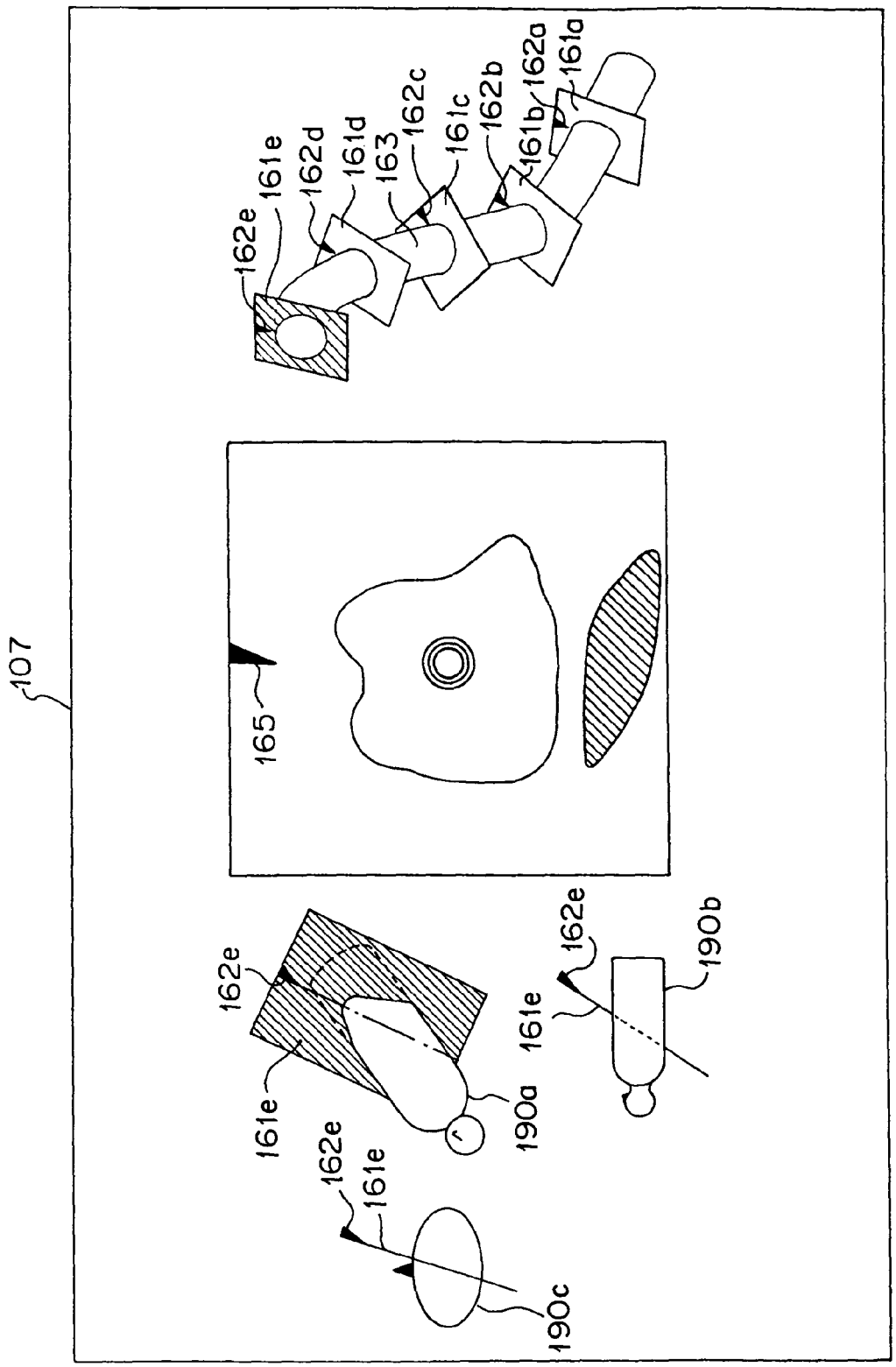
FIG. 37 is an explanatory diagram showing display examples displaying an ultrasonic image and an ultrasonic guide image on a monitor of the ultrasonic diagnostic apparatus according to the seventh embodiment.

Next, FIGS. 36 and 37 relate to a seventh embodiment of the invention. FIG. 36 is a schematic configuration diagram of an ultrasonic diagnostic apparatus. FIG. 37 is an explanatory diagram showing display examples displaying an ultrasonic image and ultrasonic guide images. According to the seventh embodiment, the differences from the fourth embodiment will be only described, and the description of the other same points will be omitted.

As shown in FIG. 36, like the magnetic sources 121 and 122 provided in the endoscope insert portion 110, plural magnetic sources 185 having solenoid coils wound in different directions are provided on a body to be examined 100.

According to the seventh embodiment, a guide image creating circuit 141 of an ultrasonic image processing portion 106 has a relative position data calculating circuit 186 and a path data calculating circuit 187.

Position and direction data based on the magnetic sources 121 and 122 and position and orientation data of body to be examined based on the magnetic sources 185 are input from the position and direction detecting portion 105 to the relative position data calculating circuit 186. The relative position data calculating circuit 186 creates data of the position and orientation of the distal end of the endoscope insert portion 110 with respect to a coordinates system based on the magnetic sources 185 (body to be examined 100). The path data calculating circuit 187 creates the ultrasonic image marker 161, the direction-of-12-o'clock marker 162 and the locus marker 163 based on an input from the relative position data calculating circuit 186. These kinds of data are recorded in the HDD 144 in connection with the respective ultrasonic image, optical image and so on like the fourth embodiment.

Next, a specific display example will be described in which an ultrasonic guide image and an ultrasonic image during radial scanning are displayed on the monitor 107 at the same time.

In the display example in FIG. 37, a guide image includes path information indicating a path of the distal end of the endoscope insert portion 110 and so on and orientation information of the body to be examined 100 on the ultrasonic image being currently displayed.

The path information includes plural ultrasonic image markers 161 (ultrasonic image markers 161a to 161e in the shown example), direction-of-12-o'clock markers 162 (direction-of-12-o'clock markers 162a to 162e in the shown example) given on the ultrasonic image markers 161 and a locus Marker 163 connecting the ultrasonic image markers 161. The orientation information includes plural body to be examined markers 190a, 190b and 190c resulting from the projection of three-dimensional body to be examined markers on a two-dimensional plane from a predetermined direction. In the examples of the ultrasonic image markers 161 and direction-of-12-o'clock markers 162 (ultrasonic image marker 161e and direction-of-12-o'clock marker 162e in the shown example) corresponding to an ultrasonic image being currently displayed are synthesized with these body to be examined markers 190a, 190b and 190c. Thus, the position and/or direction of the body to be examined 100 on the ultrasonic image are displayed. Then, the path information and orientation information are displayed on the right and left sides, respectively, of a newest ultrasonic image displayed at the center of the monitor 107.

According to the seventh embodiment, the same advantages can be substantially obtained as those of the fourth embodiment.

As described above, according to the fourth to seventh embodiments of the invention, an operator, for example, can easily recognize which part is scanned to create the current ultrasonic image by using an ultrasonic transducer within a body cavity or which part is scanned to create the recorded ultrasonic image.

More specifically, in order to create plural chronological tomographic images (ultrasonic images) by using an ultrasonic transducer moving in a body cavity, which part of an obtained ultrasonic image is scanned can be easily recognized.

Therefore, for example, when an endoscope insert portion is inserted and/or withdrawn along the digestive tract through the esophagus, the stomach and the duodenum, the locus of auxiliary images (guide images) substantially and anatomically agrees with the form of the duodenum. By using the fact, an operator can clearly identify which part within a body cavity the distal end of the endoscope insert portion exists based on the guide images. Furthermore, the operator can easily recognize which part the scanned ultrasonic image is. Therefore, unexpected failures in obtaining images may hardly occur.

Recording means for associating and recording an ultrasonic image and the position data or direction data is provided. Auxiliary image creating means reads an ultrasonic image and the position data or direction data in connection therewith from the recording means and creates an auxiliary image based on the read position data or direction data. Under this construction, which part the recorded ultrasonic image is can be easily recognized.

The auxiliary image creating means creates plural auxiliary images in different directions, and display means displays the plural auxiliary images on one screen. Thus, which part the scanned ultrasonic image being currently displayed on the screen is or which part the recorded image is can be more easily recognized.

The auxiliary image creating means creates an auxiliary image by placing a direction marker indicating a specific direction of a given ultrasonic image on the ultrasonic image marker. Under this construction, which part the scanned ultrasonic image being currently displayed is or which part the recorded ultrasonic image is can be more easily recognized.

Therefore, for example, a direction marker indicating the direction of 12 o'clock of a given ultrasonic image is placed and displayed over the ultrasonic image marker. Under this construction, an operator can more accurately compare a given ultrasonic image and anatomically position and direction thereof than a conventional method for estimating an anatomical position of a distal end of an endoscope insert portion and an anatomical direction of the direction of 12 o'clock of a given ultrasonic image based on a movement of an endoscope operating portion.

Furthermore, an input unit is provided for instructing changing a mode of displaying ultrasonic images. The auxiliary image creating unit creates an auxiliary image by changing a mode displaying an ultrasonic image marker in connection with a change in mode of displaying ultrasonic images. Under this construction, advantages below can be obtained.

First of all, a display range may be changed to a half circle display, for example, for intensely observing a range of concern in the in-body-cavity ultrasonic field. In this case, which part the scanned display range of an ultrasonic image being displayed is or at which part the display range of the ultrasonic image is recorded can be easily understood. Furthermore, a positional relationship between a displayed part and a locus that an ultrasonic transducer follows can be easily understood.

Second, an image may be rotated with respect to a specific point in order to observe an area of concern at a good position in the in-body-cavity ultrasonic field. In this case, which part the scanned ultrasonic image is or at which part the ultrasonic image is recorded can be more easily understood. Furthermore, a positional relationship between a direction of the rotated ultrasonic image and a locus that an ultrasonic transducer follows can be easily understood.

The auxiliary image creating means creates an auxiliary image including plural ultrasonic images expressing positions and directions of the plural ultrasonic images obtained through the locus that an ultrasonic probe moves. The auxiliary image creating means further creates an auxiliary image having a specific ultrasonic image marker corresponding to a displayed ultrasonic image and having a different display form from the display form of the other ultrasonic image markers for distinction. Under this construction, which part the scanned ultrasonic image being displayed in the distinctive form is or which part the recorded for the ultrasonic image is can be more easily understood.

Input means for instructing changing an ultrasonic image to be displayed among plural ultrasonic images is provided. Auxiliary image creating means selectively changes an ultrasonic image marker displayed in a different display form among plural ultrasonic image markers in connection with a change in ultrasonic image to be displayed. Under this construction, which part is recorded for a given recorded ultrasonic image can be more easily understood. Furthermore, how surrounding organs and vessels connect with each other can be easily recognized along a locus of movement of an endoscope insert portion.

Auxiliary image creating means creates an auxiliary image including a coordinates marker indicating a coordinates system, which is a reference for calculating position data or direction data of a scan plane. Under this construction, at which angle the locus is observed for a given auxiliary image can be easily understood.

Input means for instructing changing a direction of displaying an auxiliary image is provided. Auxiliary image creating means changes directions of displaying a coordinates marker and auxiliary image in response to the instruction. Under this construction, observation at various angles can be performed with respect to which part the scanned for an ultrasonic image to be displayed distinctively is or which part the recorded ultrasonic image is can be more easily understood. For example, an ultrasonic image having ultrasonic image markers overlapping with each other can be clearly understood.

Position information detecting means calculates position data or direction data of a scan plane of an ultrasonic probe with respect to a coordinates system fixed on a body to be examined. Under this construction, which part the scanned ultrasonic image being currently displayed on a screen is or which part the recorded ultrasonic image is can be compared with a direction of the body to be examined, which is easy to understand. Especially, it is easier to understand when the body to be examined moves during an examination.

According to the fourth to seventh embodiments, an auxiliary image and an ultrasonic image are displayed on one image so as to compare them. One of them may be selectively displayed on a monitor, or they may be displayed on plural monitors, which is independent from the method of comparison.

Furthermore, according to the fourth to seventh embodiments, an ultrasonic diagnostic apparatus uses mechanical radial scan type ultrasonic endoscope for performing radial scanning by mechanically rotating an ultrasonic transducer. However, the invention is not limited to the fourth to seventh embodiments. For example, an ultrasonic diagnostic apparatus may be constructed by using a linear or convex scan type ultrasonic endoscope, instead of radial scanning, having plural ultrasonic transducers provided closely to an insert axis of an endoscope insert portion. In this case, an operator may operate to twist the endoscope insert portion about the insert axis.

According to the fourth to seventh embodiments, an ultrasonic image marker being displayed has a different color from that of the other ultrasonic image markers. However, the display forms may be differentiated in density, shading, shape or other forms.

The invention claimed is:

1. An ultrasonic diagnostic apparatus moving an ultrasonic transducer within a body cavity of a body to be examined and creating plural chronological tomographic images in accordance with the movement, the apparatus comprising:
    position information detecting means for detecting position information of the ultrasonic transducer when the tomographic images are obtained;
    means for creating an auxiliary image indicating position information of the tomographic images along a non-linear path of the movement of the ultrasonic transducer based on position information obtained by the position information detecting means and the tomographic images corresponding to the position information; and
    display control means for displaying the auxiliary image and a tomographic image corresponding to the auxiliary image so as to compare them;
    recording means for recording the tomographic images and the position information in association with each other;
    input means for selecting and indicating one tomographic image to be displayed together with the auxiliary image from among the plural tomographic images recorded in the recording means,
    wherein the auxiliary image creating means creates, during radial scanning by the ultrasonic transducer, the auxiliary image including a plurality of two-dimensional anisotropic ultrasonic image markers arranged along the movement path of the ultrasonic transducer, each of the markers expressing a position and orientation in three dimensional space of a scan plane of the ultrasonic transducer when the tomographic image is obtained,
    wherein the auxiliary image creating means further makes a display form of the ultrasonic image marker corresponding to the tomographic image displayed for comparison among the plural ultrasonic image markers different from a display form of the other ultrasonic image markers, and
    wherein the auxiliary image creating means again creates an auxiliary image such that the ultrasonic image marker at a position where the one tomographic image was obtained and the ultrasonic image markers other than the ultrasonic image marker at the position where the one tomographic image was obtained are displayed in different display forms, in conjunction with the selecting of the one tomographic image by the input means after the radial scanning by the ultrasonic transducer.

2. The ultrasonic diagnostic apparatus according to claim 1, wherein the display control means causes display of the auxiliary image and a tomographic image corresponding to the auxiliary image on the same screen.

3. The ultrasonic diagnostic apparatus according to claim 1, further comprising recording means for relating and recording the tomographic image and the position information,
    wherein the auxiliary image creating means can create an auxiliary image indicating position information of the tomographic image based on the position information read from the recording means and the tomographic image corresponding to the position information.

4. The ultrasonic diagnostic apparatus according to claim 1, wherein:
    the auxiliary image creating means creates plural auxiliary images for indicating position information of the tomographic images from different directions; and
    the display control means causes display of the auxiliary images on the same screen so as to compare them.

5. The ultrasonic diagnostic apparatus according to claim 1, wherein the auxiliary image creating means creates the auxiliary image by synthesizing the plural ultrasonic image markers and a locus marker of the ultrasonic transducer, which is created by sequentially connecting the ultrasonic image markers.

6. The ultrasonic diagnostic apparatus according to claim 1, wherein the auxiliary image creating means superimposes on the ultrasonic image marker a direction marker indicating a specific direction of a tomographic image corresponding to the ultrasonic image marker.

7. The ultrasonic diagnostic apparatus according to claim 1, further comprising input means instructing changing a mode of displaying The tomographic image,
   wherein the auxiliary image creating means creates an auxiliary image having the ultrasonic image marker displayed in a mode changed in connection with a change in mode of displaying the tomographic images.

8. The ultrasonic diagnostic apparatus according to claim 1, further comprising input means instructing selecting a tomographic image to be displayed among the plural tomographic images recorded in the recording means,
   wherein the auxiliary image creating means changes the ultrasonic image marker to be displayed in a different display form in connection with a selection of the tomographic image to be displayed.

9. The ultrasonic diagnostic apparatus according to claim 1, wherein the auxiliary image creating means creates the auxiliary image including a marker indicating a coordinates system, which is a reference for creating the ultrasonic image markers.

10. The ultrasonic diagnostic apparatus according to claim 9, further comprising input means instructing changing a direction of displaying the auxiliary image,
    wherein the auxiliary image creating means changes a direction of displaying the auxiliary image as well as the marker indicating the coordinates system based on the instruction from the input means.

11. The ultrasonic diagnostic apparatus according to claim 1, wherein the position information detecting means calculates the position information based on a coordinates system with reference to a body to be examined.

* * * * *